(12) United States Patent
Danho et al.

(10) Patent No.: US 7,410,949 B2
(45) Date of Patent: Aug. 12, 2008

(54) NEUROPEPTIDE-2 RECEPTOR (Y-2R) AGONISTS AND USES THEREOF

(75) Inventors: Waleed Danho, Wayne, NJ (US); George Ehrlich, New York, NY (US); David C Fry, Langhorne, PA (US); Wajiha Khan, East Hanover, NJ (US); Joseph Swistok, Nutley, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/328,743

(22) Filed: Jan. 10, 2006

(65) Prior Publication Data

US 2006/0160742 A1 Jul. 20, 2006

Related U.S. Application Data

(60) Provisional application No. 60/644,840, filed on Jan. 18, 2005.

(51) Int. Cl.
*A61K 38/10* (2006.01)
*C07K 7/08* (2006.01)
(52) U.S. Cl. .................................... 514/14; 530/327
(58) Field of Classification Search ................ None
See application file for complete search history.

(56) References Cited

U.S. PATENT DOCUMENTS 5,283,317 A 2/1994 Saifer et al.
5,468,478 A 11/1995 Saifer et al.

FOREIGN PATENT DOCUMENTS

WO WO 94/22467 A1 10/1994
WO WO 2005/080242 A2 * 9/2005

OTHER PUBLICATIONS

Poter, E.K., et. al. Eur. J. Pharmac. 267, 253-262 (1994).
Bloom, S., et. al., Nature vol. 418, Aug. 8, 2002, p. 650-654.
Krstenansky, et. al. in Peptides, Proceedings of the Twelfth American Peptide Symposium., J. Smith and J. Rivier Editors, ESCOM. Leiden p. 136-137 (not dated).
Somack, R., et. al. (1991) Free Rad Res Commun 12-13:553-562.
Saifer, MGP, et. al. (1997) Polym Preprints 38:576-577.
Sherman, M. R., et. al. (1997) in J M Harris, et. al., (Eds.), Poly(ethylene glycol) Chemistry and Biological Applications. ACS Symposium Series 680 p. 155-169, Washington, DC: American Chemical Society.

(Continued)

*Primary Examiner*—Jeffrey E Russel
(74) *Attorney, Agent, or Firm*—George W. Johnston; Dennis P. Tramaloni; Samuel H. Megerditchian

(57) ABSTRACT

Provided herein are neuropeptide-2 receptor agonists of the formula (I):

$$Y-R_1-R_2-X-R_3-R_4-R_5-R_6-R_7-R_8-R_9-R_{10}-R_{11}-R_{12}-R_{13}-R_{14}-NH_2, \quad (I)$$

as well as pharmaceutically acceptable salts, derivatives and fragments thereof, wherein the substituents are as those disclosed in the specification. These compounds, and the pharmaceutical compositions containing them, are useful for the treatment of diseases such as, for example, obesity.

17 Claims, 10 Drawing Sheets

OTHER PUBLICATIONS

Bloom, S., et. al., New England J. of Med. (2003) 349, 941-948.
Balasubramaniam, et. al., J. Med. Chem. (2000) 43, 3420-3427.
G. Beck-Sickinger, et. al., Regulatory peptides 75-76 (10998) p. 3-8.
A.G. Beck-Sickinger, et. al., FEBS Letters 394 (1996) 169-173.
G. Jung, et. al., Eur. J. Biochem. 225, (1994), p. 947-958.
A.G. Beck-Sickinger, et. al. Biopolymers (Peptide Science) vol. 27, p. 123-142 (1995).
J. R. Reeve, Jr., et. al., Biochemistry 2000, p. 9935-9942.
Beck-Sickinger, A.G., et al., European Journal Of Biochemistry, vol. 206, No. 3, pp. 957-964 (1992).
Beck A., et al., FEBS Letters, vol. 244, No. 1, pp. 119-122 (1989).
Beck-Sickinger, A.G., et al., European Journal of Biochemistry, vol. 194, No. 2, pp. 449-456 (1990).
Krstenansky, J.L., et al., Proceedings of the National Academy of Sciences of the United States of America, vol. 86, No. 12, pp. 4377-4381 (1989).
Boggiano, M.M., et al., Obesity Reviews, vol. 6, No. 4, pp. 307-322 (2005).

* cited by examiner

EFFECTS OF COMPOUND FROM EXAMPLE (5) ON FOOD INTAKE IN MALE C57BL/6J MICE BY THE IP ROUTE OF ADMINISTRATION

EFFECTS OF COMPOUND FROM EXAMPLE (73) ON FOOD INTAKE IN MALE C57BL/6J MICE BY THE SC ROUTE OF ADMINISTRATION

EFFECTS OF COMPOUND FROM EXAMPLE (74) ON FOOD INTAKE IN MALE C57BL/6J
MICE BY THE SC ROUTE OF ADMINISTRATION

NEUROPEPTIDE-2 RECEPTOR (Y-2R) AGONISTS AND USES THEREOF

PRIORITY TO RELATED APPLICATIONS

This application claims the benefit of U.S. Provisional Application No. 60/644,840, filed Jan. 18, 2005, which is hereby incorporated by reference in its entirety.

FIELD OF THE INVENTION

The invention relates to truncated analogs of $PYY_{3-36}$. The analogs are agonists of neuropeptide-2 receptor and are useful for the treatment of metabolic disorders, such as, for example, obesity.

All documents cited herein are hereby expressly incorporated herein by reference.

BACKGROUND OF THE INVENTION

Obesity is widely recognized as a serious health problem for developed countries, and has reached epidemic status in the United States. According to recent studies, more than 50% of the U.S. population is considered overweight, with more than 25% diagnosed as clinically obese and at considerable risk for heart disease, non-insulin dependent diabetes mellitus (NIDDM), hypertension, and certain cancers. This epidemic presents a significant burden on the health care system as projected obesity treatment costs of more than $70 billion annually are expected in the U.S. alone. Strategies for treating obesity include reduction of food intake and enhancing the expenditure of energy.

Neuropeptide Y (NPY), a 36 amino acid peptide neurotransmitter, is a member of the pancreatic polypeptide class of neurotransmitters/neurohormones which has been shown to be present in both the periphery and central nervous system. NPY is one of the most potent orexogenic agents known and has been shown to play a major role in the regulation of food intake in animals, including humans.

Five neuropeptide Y receptors (NPY), the Y1-, Y2-, Y3-, Y4, and Y5- and Y6-subtypes, have been cloned, which belong to the rhodopsin-like G-protein-coupled, 7-transmembrane helix-spanning receptors (GPCR). The NPY Y2 receptor (Y2R) is a 381 amino-acid which inhibits the activation of adenyl cyclase via $G_i$ while having low homology with other known NPY receptors. There is a high degree of conservation between rat and human Y2 receptor with 98% amino acid identity.

The Y2R receptor is widely distributed within the central nervous system in both rodents and humans. In the hypothalamus, Y2 mRNA is localized in the arcuate nucleus, preoptic nucleus, and dorsomedial nucleus. In the human brain, Y2R is the predominant Y receptor subtype. Within the arcuate nuclease, over 80% of the NPY neurons co-express Y2R mRNA. Application of a Y2-selective agonist has been shown to reduce the release of NPY from hypothalamic slices in vitro, whereas the Y2 non-peptide antagonist BIIE0246 increases NPY release. These findings support the role of Y2R as a presynaptic autoreceptor that regulates the NPY release and hence may be involved in the regulation of feeding. (Poter, E. K., et al. Eur. J. Pharmac. 267, 253-262 (1994)).

Peptide $YY_{3-36}$ ($PYY_{3-36}$) is a 33 amino acid linear peptide having specific neuropeptide Y2 (NPY2R) agonist activity. It has been demonstrated that Intra-arcuate (IC) or Intra-peritoneal (IP) injection of $PYY_{3-36}$ reduced feeding in rats and, as a chronic treatment, reduced body weight gain. Intra-venous (IV) infusion (0.8 pmol/kg/min) for 90 min of $PYY_{3-36}$ reduced food intake in obese and normal human subjects 33% over 24 hours. These finding suggest that the PYY system may be a therapeutic target for the treatment of obesity. (Bloom, S. et al, Nature Vol. 418, 8 Aug. 2002, P. 650-654). Further, a $Cys^2$-(D)$Cys^{27}$-cyclized version of PYY, in which residues 5-24 were replaced by a methylene-chain of 5 to 8 carbons in length, showed activation of the intestinal PYY receptor, as evidenced by reduced current across voltage-clamped mucosal preparations of rat jejunum. (Krstenansky, et al. in Peptides, Proceedings of the Twelfth American Peptide Symposium. J. Smith and J. Rivier Editors, ESCOM. Leiden Page 136-137).

Further, covalent modification of proteins with poly(ethylene glycol) or poly (ethylene oxide) (both referred to as PEG), was demonstrated with superoxide dismutase (Somack, R, et al., (1991) Free Rad Res Commun 12-13:553-562; U.S. Pat. Nos. 5,283,317 and 5,468,478) and for other types of proteins, e.g., cytokines (Saifer, M G P, et al., (1997) Polym Preprints 38:576-577; Sherman, M R, et al., (1997) in J M Harris, et al., (Eds.), Poly(ethylene glycol) Chemistry and Biological Applications. ACS Symposium Series 680 (pp. 155-169) Washington, D.C.: American Chemical Society).

A need exists, however, for novel engineered analogs of PYY having significantly lower molecular weight, while possessing equal or better potency, pharmacokinetic properties and pharmacological properties as existing Y2R agonists. A need also exists for pegylated analogs of PYY in order to, for example, increase peptide half-life and reduce immunogenicity in subjects in need of such agonists.

SUMMARY OF THE INVENTION

In an embodiment of the present invention, a neuropeptide-2 receptor agonist of the formula (I) is provided:

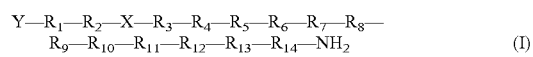

(I)

wherein X is selected from the group consisting of N-piperazin-1-yl-4(3H)-quinozolinone-3-acetic acid (Pqa), N-(5-O-carboxymethyl)-serotonin (Cms), 4-(2-aminomethyl)-6-dibenzofuranpropanoic acid, 4-(1-piperidin-4-yl)-butanoic acid and 4-(2-aminoethyl)-1-carboxymethyl piperazine, Y is H, a substituted or unsubstituted alkyl, a substituted or unsubstituted lower alkyl, a substituted or unsubstituted aryl, a substituted or unsubstituted alkoxy or a poly(ethylene) glycol moiety, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methylArg, Phe, 3,4,5-

TrifluoroPhe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr, N-methyl Tyr, Trp, Tic, Bip, Dip, (1)Nal, (2)Nal, 3,4,5-TrifluroPhe or 2,3,4,5,6-Pentafluoro Phe, $R_6$ is Leu, Ala, (D)Leu or N-methyl Leu, $R_7$ is Asn, Ala or (D)Asn, $R_8$ is Leu, Ala, (D)Leu or N-methyl Leu, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, and $R_{14}$ is Tyr, (D) Tyr or N-methyl Tyr, or a pharmaceutically acceptable salt thereof.

In another embodiment of the present invention, a neuropeptide-2 receptor agonist of the formula (II) is provided:

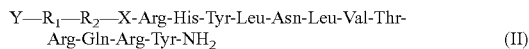

Y—$R_1$—$R_2$—X-Arg-His-Tyr-Leu-Asn-Leu-Val-Thr-Arg-Gln-Arg-Tyr-$NH_2$ (II)

(SEQ ID NO: 1)

wherein X is a moiety selected from the group consisting of N-piperazin-1-yl-4(3H)-quinozolinone-3-acetic acid (Pqa), N-(5-O-carboxymethyl)-serotonin (Cms), 4-(2-aminomethyl)-6-dibenzofuranpropanoic acid, 4-(1-piperidin-4-yl)-butanoic acid and 4-(2-aminoethyl)-1-carboxymethyl piperazine, Y is H, a substituted or unsubstituted alkyl, a substituted or unsubstituted lower alkyl, a substituted or unsubstituted aryl, a substituted or unsubstituted alkoxy or a poly(ethylene) glycol moiety, $R_1$ is Ile, Ala, (D) Ile, N-methyl Ile, Aib, 1-1Aic, 2-2 Aic, Ach or Acp, and $R_2$ is Lys, Ala, (D) Lys, NMelys, Nle or (Lys-Gly), or a pharmaceutically acceptable salt thereof.

In yet another embodiment of the present invention, a neuropeptide-2 receptor agonist of the formula (III) is provided:

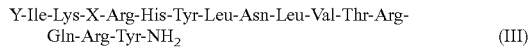

Y-Ile-Lys-X-Arg-His-Tyr-Leu-Asn-Leu-Val-Thr-Arg-Gln-Arg-Tyr-$NH_2$ (III)

(SEQ ID NO: 2)

wherein X is selected from the group consisting of N-piperazin-1-yl-4(3H)-quinozolinone-3-acetic acid (Pqa), N-(5-O-carboxymethyl)-serotonin (Cms), 4-(2-aminomethyl)-6-dibenzofuranpropanoic acid, 4-(1-piperidin-4-yl)-butanoic acid and 4-(2-aminoethyl)-1-carboxymethyl piperazine, and Y is H, a substituted or unsubstituted alkyl, a substituted or unsubstituted lower alkyl, a substituted or unsubstituted aryl, a substituted or unsubstituted alkoxy or a poly(ethylene) glycol moiety, or a pharmaceutically acceptable salt thereof.

In a further embodiment of the present invention, a method of treating obesity in a patient in need thereof is provided, the method having the steps of administering to said patient a therapeutically effective amount of a neuropeptide-2 receptor agonist of the formula (I):

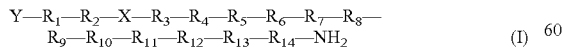

Y—$R_1$—$R_2$—X—$R_3$—$R_4$—$R_5$—$R_6$—$R_7$—$R_8$—$R_9$—$R_{10}$—$R_{11}$—$R_{12}$—$R_{13}$—$R_{14}$—$NH_2$ (I)

wherein X is selected from the group consisting of N-piperazin-1-yl-4(3H)-quinozolinone-3-acetic acid (Pqa), N-(5-O-carboxymethyl)-serotonin (Cms), 4-(2-aminomethyl)-6-dibenzofuranpropanoic acid, 4-(1-piperidin-4-yl)-butanoic acid and 4-(2-aminoethyl)-1-carboxymethyl piperazine, Y is H, a substituted or unsubstituted alkyl, a substituted or unsubstituted lower alkyl, a substituted or unsubstituted aryl, a substituted or unsubstituted alkoxy or a poly(ethylene) glycol moiety, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methylArg, Phe, 3,4,5-TrifluoroPhe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr, N-methyl Tyr, Trp, Tic, Bip, Dip, (1)Nal, (2)Nal, 3,4,5-TrifluroPhe or 2,3,4,5,6-Pentafluoro Phe, $R_6$ is Leu, Ala, (D)Leu or N-methyl Leu, $R_7$ is Asn, Ala or (D)Asn, $R_8$ is Leu, Ala, (D)Leu or N-methyl Leu, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, and $R_{14}$ is Tyr, (D) Tyr or N-methyl Tyr, or a pharmaceutically acceptable salt thereof.

In a yet further embodiment of the present invention, a neuropeptide-2 receptor agonist is provided having a $PYY_{3-36}$ derivative with amino acid residues 5-24 are replaced by a moiety of about 8 to about 11 Angstroms in length.

The invention is now further illustrated by the following detailed description and the accompanying figures from which further embodiments, features and advantages may be taken.

DETAILED DESCRIPTION OF THE INVENTION

Figure 1:
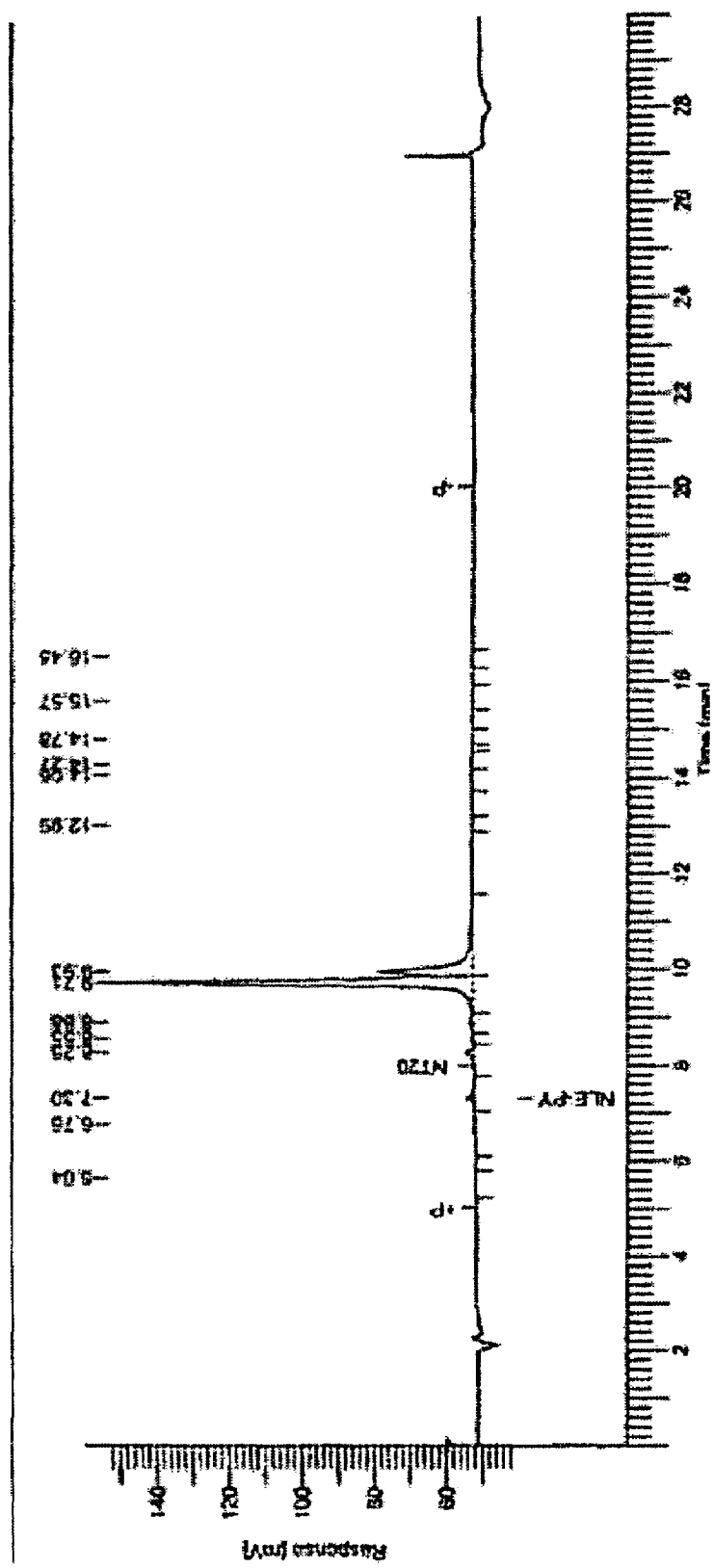
FIG. 1 shows a HPLC chromatogram of a compound of the present invention.

The present invention pertains to analogs of $PYY_{3-36}$, wherein amino acid residues 5-24 are replaced by a moiety such as, for example, Pqa or Cms. For example, the invention provides compounds of the formula $PYY_{3-4}$-Pqa-$PYY_{25-36}$:

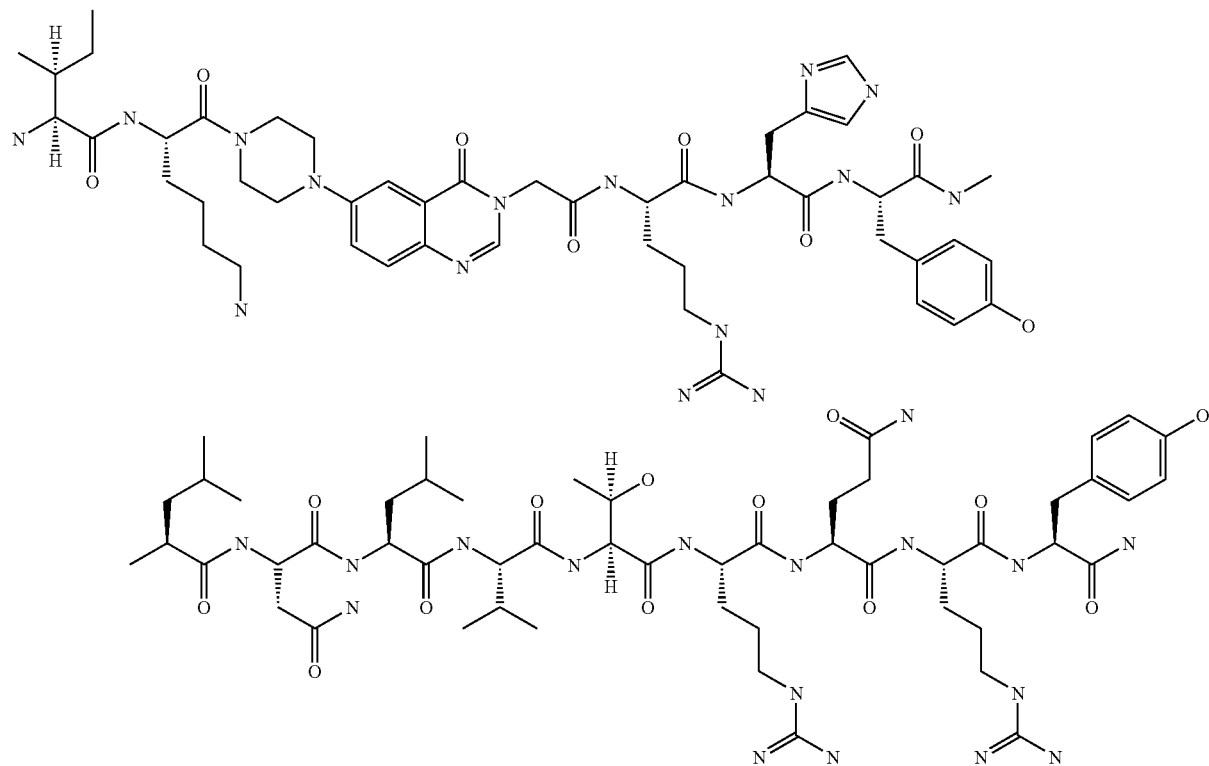
and the formula PYY$_{3\text{-}4}$-Cms-PYY$_{25\text{-}36}$:
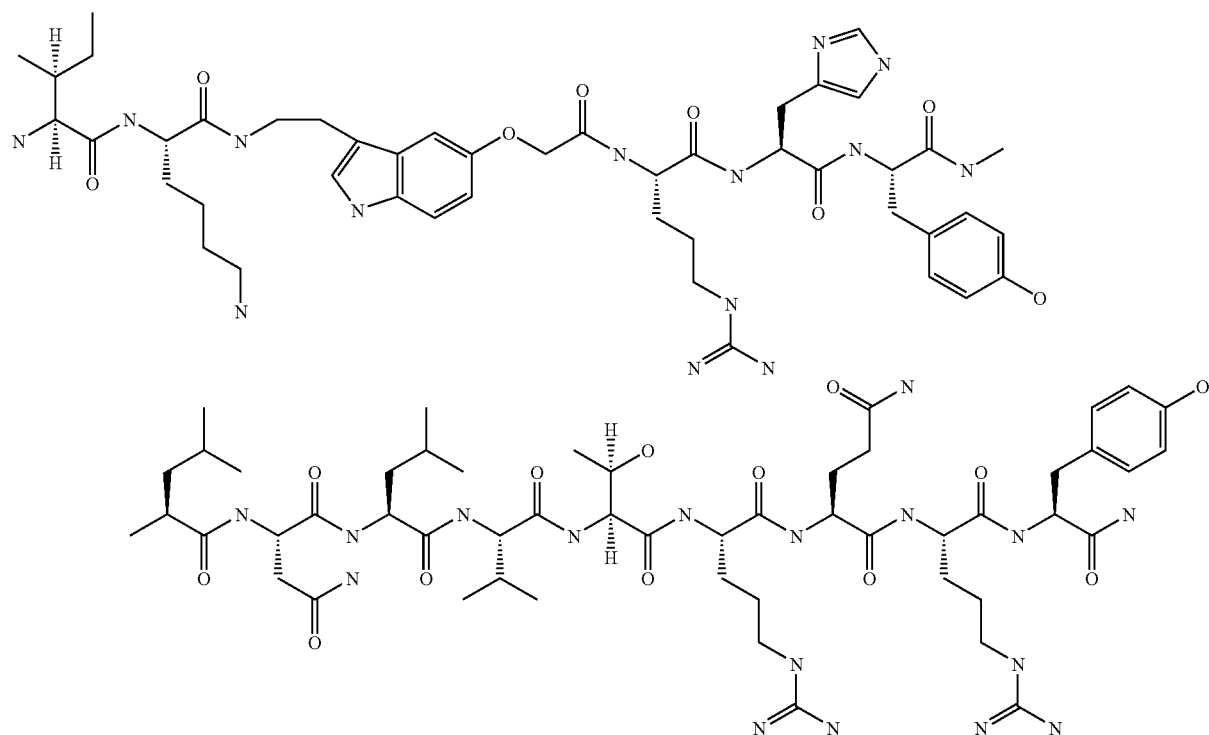

The invention further provides compounds of the formula:

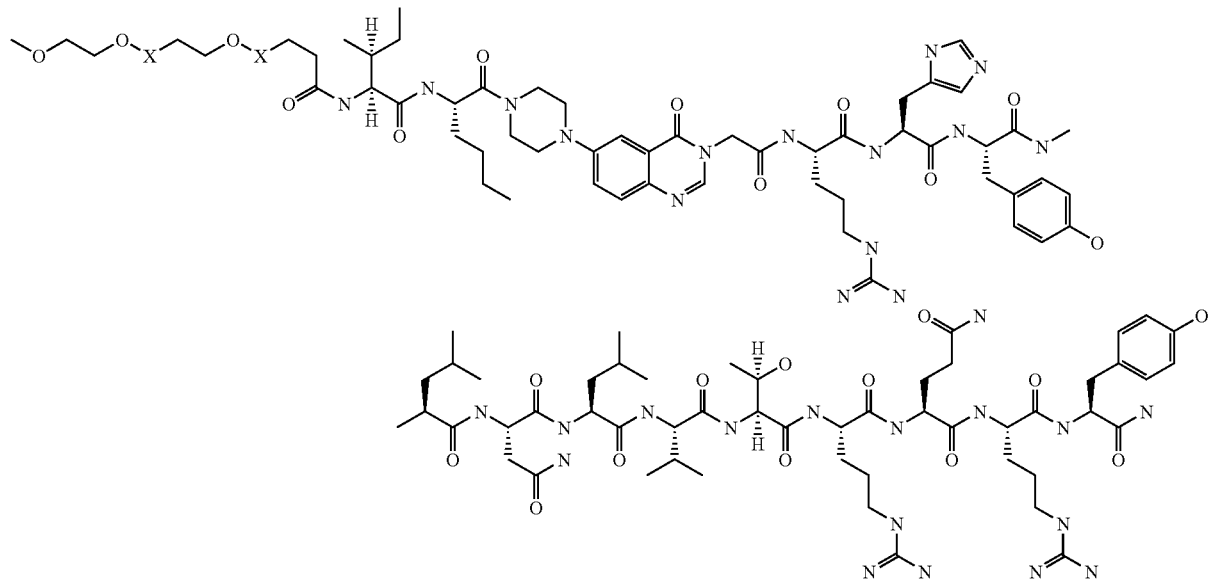

Using the NMR-derived structure of native $PYY_{3-36}$ as a guide, analogs are herein presented having a moiety replace amino acid residues 5-24 of $PYY_{3-36}$. Examples of such moieties include N-piperazin-1-yl-4-(3H)-quinazolinone-3-acetic acid (Pqa) and N-(5-O-carboxymethyl)-seratonin (Cms). The moiety is typically rigid and advantageously stabilizes the molecule's tertiary structure, thereby yielding truncated analogs with the desired potency and pharmacokinetic and pharmacological properties. The moiety is typically about 8 to about 11 Angstroms in length, preferably about 9 to about 11 Angstroms in length, more preferably about 9 to about 10 Angstroms in length, even more preferably about 8 to about 10 Angstroms in length, still more preferably about 8 to about 9 Angstroms in length.

The compounds of the invention are also advantageous because they are truncated versions of the $PYY_{3-36}$. Thus, the shorter peptides not only facilitate easier synthesis and purification of the compounds, but also improve and reduce manufacturing procedures and expenses. Moreover, the compounds of the invention will interact preferably with PYY receptors and not with homologous receptors such as NPY Y1, Y4 and Y5. Unwanted agonist or antagonist side reactions are, thereby, minimized.

It is to be understood that the invention is not limited to the particular embodiments of the invention described herein, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

Although any methods, devices and materials similar or equivalent to those described herein can be used in the practice or testing of the invention, the preferred methods, devices and materials are now described.

All peptide sequences mentioned herein are written according to the usual convention whereby the N-terminal amino acid is on the left and the C-terminal amino acid is on the right, unless noted otherwise. A short line between two amino acid residues indicates a peptide bond. Where the amino acid has isomeric forms, it is the L form of the amino acid that is represented unless otherwise expressly indicated. For convenience in describing this invention, the conventional and nonconventional abbreviations for the various amino acids are used. These abbreviations are familiar to those skilled in the art, but for clarity are listed below:

Asp=D=Aspartic Acid; Ala=A=Alanine; Arg=R=Arginine; Asn=N=Asparagine; Gly=G=Glycine; Glu=E=Glutamic Acid; Gln=Q=Glutamine; His=H=Histidine; Ile=I=Isoleucine; Leu=L=Leucine; Lys=K=Lysine; Met=M=Methionine; Phe=F=Phenylalanine; Pro=P=Proline; Ser=S=Serine; Thr=T=Threonine; Trp=W=Tryptophan; Tyr=Y=Tyrosine; and Val=V=Valine.

Also for convenience, and readily known to one skilled in the art, the following abbreviations or symbols are used to represent the moieties, reagents and the like used in this invention:

| | |
|---|---|
| Pqa | N-piperazin-1-yl-4-(3H)-quanazolinone-3-acetic -acid; |
| Cms | N-(5-O-carboxymethyl)-seratonin; |
| 3,4,5, F3-Phe | 3,4,5-Trifluoro phenylalanine; |
| 2,3,4,5,6, F5-Phe | 2,3,4,5,6-Pentafluoro phenylalanine; |
| 4-MeO-Apc | 4-Methoxy-1-amino 4-phenylcyclohexane carboxylic acid; |
| 3-Pal | 3-Pyridyl alanine; |
| 4-Pal | 4-Pyridyl Alanine; |
| Aib | Amino isobutyric acid; |
| 1-1-Aic | 1 Amino-indane 1-carboxylic acid; |
| 2-2-Aic | 2 Amino-indane 2-carboxylic acid; |
| Ach | 1-Amino cyclohexyl carboxylic acid; |
| Acp | 1-Amino cyclopentyl carboxylic acid; |
| Fmoc | 9-Fluorenylmethyloxycarbonyl; |
| Allyl | Allyl ester; |
| Aloc | Allyloxycarbonyl; |
| Mtt | 4-Methyltrityl; |
| 2Pip | 2-Phenylisopropyl ester; |
| Pmc | 2,2,5,7,8-Pentamethylchroman-6-sulfonyl; |
| $CH_2Cl_2$ | Methylene chloride; |
| A2O | Acetic anhydride; |
| $CH_3CN$ | Acetonitrile; |

| | -continued |
|---|---|
| DMAc | Dimethylacetamide; |
| DMF | Dimethylformamide; |
| DIPEA | N,N-Diisopropylethylamine; |
| TFA | Trifluoroacetic acid; |
| HOBT | N-Hydroxybenzotriazole; |
| DIC | N,N'-Diisopropylcarbodiimide; |
| BOP | Benzotriazol-1-yloxy-tris-(dimethylamino) phosphonium-Hexafluorophosphate; |
| HBTU | 2-(1H-Benzotriazole-1-yl)-1,1,3,3-tetramethyluronium-Hexafluorophosphate; |
| NMP | 1-methyl 2-Pyrolidenone; |
| Bip | Biphenylalanin or 4-Phenyl-phentylalanine; |
| Dip | Diphenylalanine; |
| Tic | 1,2,3,4,-tetrahydroisoquinoline-3 carboxylic acid; |
| FAB-MS | Fast atom bombardment mass spectrometry; and |
| ES-MS | Electro spray mass spectrometry. |

As used herein, the term "alkyl" means a branched or unbranched, cyclic or acyclic, saturated or unsaturated (e.g. alkenyl or alkynyl) hydrocarbyl radical which may be substituted or unsubstituted. Where cyclic, the alkyl group is preferably $C_3$ to $C_{12}$, more preferably $C_5$ to $C_{10}$, more preferably $C_5$ to $C_7$. Where acyclic, the alkyl group is preferably $C_1$ to $C_{10}$, more preferably $C_1$ to $C_6$, more preferably methyl, ethyl, propyl (n-propyl or isopropyl), butyl (n-butyl, isobutyl or tertiary-butyl) or pentyl (including n-pentyl and isopentyl), more preferably methyl. It will be appreciated therefore that the term "alkyl" as used herein includes alkyl (branched or unbranched), substituted alkyl (branched or unbranched), alkenyl (branched or unbranched), substituted alkenyl (branched or unbranched), alkynyl (branched or unbranched), substituted alkynyl (branched or unbranched), cycloalkyl, substituted cycloalkyl, cycloalkenyl, substituted cycloalkenyl, cycloalkynyl and substituted cycloalkynyl.

As used herein, the term "lower alkyl" means a branched or unbranched, cyclic or acyclic, saturated or unsaturated (e.g. alkenyl or alkynyl) hydrocarbyl radical wherein said cyclic lower alkyl group is $C_5$, $C_6$ or $C_7$, and wherein said acyclic lower alkyl group is $C_1$, $C_2$, $C_3$ or $C_4$, and is preferably selected from methyl, ethyl, propyl (n-propyl or isopropyl) or butyl (n-butyl, isobutyl or tertiary-butyl). It will be appreciated therefore that the term "lower alkyl" as used herein includes lower alkyl (branched or unbranched), lower alkenyl (branched or unbranched), lower alkynyl (branched or unbranched), cycloloweralkyl, cycloloweralkenyl and cycloloweralkynyl.

As used herein, the term "acyl" means an optionally substituted alkyl, cycloalkyl, heterocyclic, aryl or heteroaryl group bound via a carbonyl group and includes groups such as acetyl, propionyl, benzoyl, 3-pyridinylcarbonyl, 2-morpholinocarbonyl, 4-hydroxybutanoyl, 4-fluorobenzoyl, 2-naphthoyl, 2-phenylacetyl, 2-methoxyacetyl and the like.

As used herein, the term "aryl" means a substituted or unsubstituted carbocyclic aromatic group, such as phenyl or naphthyl, or a substituted or unsubstituted heteroaromatic group containing one or more, preferably one, heteroatom, such as pyridyl, pyrrolyl, furanyl, thienyl, thiazolyl, isothiazolyl, oxazolyl, isoxazolyl, oxadiazolyl, thiadiazolyl pyrazolyl, imidazolyl, triazolyl, pyrimidinyl pyridazinyl, pyrazinyl, triazinyl, indolyl, indazolyl, quinolyl, quinazolyl, benzimidazolyl, benzothiazolyl, benzisoxazolyl and benzisothiazolyl.

The alkyl and aryl groups may be substituted or unsubstituted. Where substituted, there will generally be 1 to 3 substituents present, preferably 1 substituent. Substituents may include: carbon-containing groups such as alkyl, aryl, arylalkyl (e.g. substituted and unsubstituted phenyl, substituted and unsubstituted benzyl); halogen atoms and halogen-containing groups such as haloalkyl (e.g. trifluoromethyl); oxygen-containing groups such as alcohols (e.g. hydroxyl, hydroxyalkyl, aryl(hydroxyl)alkyl), ethers (e.g. alkoxy, aryloxy, alkoxyalkyl, aryloxyalkyl), aldehydes (e.g. carboxaldehyde), ketones (e.g. alkylcarbonyl, alkylcarbonylalkyl, arylcarbonyl, arylalkylcarbonyl, arycarbonylalkyl), acids (e.g. carboxy, carboxyalkyl), acid derivatives such as esters (e.g. alkoxycarbonyl, alkoxycarbonylalkyl, alkylcarbonyloxy, alkylcarbonyloxyalkyl), amides (e.g. aminocarbonyl, mono- or di-alkylaminocarbonyl, aminocarbonylalkyl, mono-or di-alkylaminocarbonylalkyl, arylaminocarbonyl), carbamates (e.g. alkoxycarbonylamino, arloxycarbonylamino, aminocarbonyloxy, mono-or di-alkylaminocarbonyloxy, arylminocarbonloxy) and ureas (e.g. mono- or di-alkylaminocarbonylamino or arylaminocarbonylamino); nitrogen-containing groups such as amines (e.g. amino, mono- or di-alkylamino, aminoalkyl, mono- or di-alkylaminoalkyl), azides, nitriles (e.g. cyano, cyanoalkyl), nitro; sulfur-containing groups such as thiols, thioethers, sulfoxides and sulfones (e.g. alkylthio, alkylsulfinyl, alkylsulfonyl, alkylthioalkyl, alkylsulfinylalkyl, alkylsulfonylalkyl, arylthio, arysulfinyl, arysulfonyl, arythioalkyl, arylsulfinylalkyl, arylsulfonylalkyl); and heterocyclic groups containing one or more, preferably one, heteroatom, (e.g. thienyl, furanyl, pyrrolyl, imidazolyl, pyrazolyl, thiazolyl, isothiazolyl, oxazolyl, oxadiazolyl, thiadiazolyl, aziridinyl, azetidinyl, pyrrolidinyl, pyrrolinyl, imidazolidinyl, imidazolinyl, pyrazolidinyl, tetrahydrofuranyl, pyranyl, pyronyl, pyridyl, pyrazinyl, pyridazinyl, piperidyl, hexahydroazepinyl, peperazinyl, morpholinyl, thianaphthyl, benzofuranyl, isobenzofuranyl, indolyl, oxyindolyl, isoindolyl, indazolyl, indolinyl, 7-azaindolyl, benzopyranyl, coumarinyl, isocoumarinyl, quinolinyl, isoquinolinyl, naphthridinyl, cinnolinyl, quinazolinyl, pyridopyridyl, benzoxazinyl, quinoxalinyl, chromenyl, chromanyl, isochromanyl, phthalazinyl and carbolinyl).

The lower alkyl groups may be substituted or unsubstituted, preferably unsubstituted. Where substituted, there will generally be 1 to 3 substitutents present, preferably 1 substituent. Substituents include the substituent groups listed above other than alkyl, aryl and arylalkyl.

As used herein, the term "alkoxy" means alkyl-O— and "alkoyl" means alkyl-CO—. Alkoxy substituent groups or alkoxy-containing substituent groups may be substituted by one or more alkyl groups.

As used herein, the term "halogen" means a fluorine, chlorine, bromine or iodine radical, preferably a fluorine, chlorine or bromine radical, and more preferably a fluorine or chlorine radical.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

The present representative compounds may be readily synthesized by any known conventional procedure for the formation of a peptide linkage between amino acids. Such conventional procedures include, for example, any solution phase procedure permitting a condensation between the free alpha amino group of an amino acid or residue thereof having its carboxyl group and other reactive groups protected and the free primary carboxyl group of another amino acid or residue thereof having its amino group or other reactive groups protected.

Such conventional procedures for synthesizing the novel compounds of the present invention include for example any solid phase peptide synthesis method. In such a method the synthesis of the novel compounds can be carried out by sequentially incorporating the desired amino acid residues one at a time into the growing peptide chain according to the general principles of solid phase methods. Such methods are disclosed in, for example, Merrifield, R. B., J. Amer. Chem. Soc. 85, 2149-2154 (1963); Barany et al., The Peptides, Analysis, Synthesis and Biology, Vol. 2, Gross, E. and Meienhofer, J., Eds. Academic Press 1-284 (1980), which are incorporated herein by reference.

Common to chemical syntheses of peptides is the protection of reactive side chain groups of the various amino acid moieties with suitable protecting groups, which will prevent a chemical reaction from occurring at that site until the protecting group is ultimately removed. Usually also common is the protection of the alpha amino group on an amino acid or fragment while that entity reacts at the carboxyl group, followed by the selective removal of the alpha amino protecting group at allow a subsequent reaction to take place at that site. While specific protecting groups have been disclosed in regard to the solid phase synthesis method, it should be noted that each amino acid can be protected by a protective group conventionally used for the respective amino acid in solution phase synthesis.

Alpha amino groups may be protected by a suitable protecting group selected from aromatic urethane-type protecting groups, such as allyloxycarbony, benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropyloxycarbonyl, 9-fluorenylmethyloxycarbonyl (Fmoc) and p-methoxybenzyloxycarbonyl (Moz); aliphatic urethane-type protecting groups, such as t-butyloxycarbonyl (Boc), diisopropylmethyloxycarbonyl, isopropyloxycarbonyl, and allyloxycarbonyl. Herein, Fmoc is most preferred for alpha amino protection.

Guanidino groups may be protected by a suitable protecting group selected from nitro, p-toluenesulfonyl (Tos), (Z,) pentamethylchromanesulfonyl (Pmc), 4-Methoxy-2,3,6,-trimethylbenzzenesulfonyl (Mtr), (Pmc), and (Mtr) are most preferred for arginine (Arg).

The ε-amino groups may be protected by a suitable protecting group selected from 2-chloro benzyloxycarbonyl (2-Cl-Z), 2-Bromo benztloxycarbonyl (2-Br-Z)- and t-butyloxycarbonyl (Boc). Boc is the most preferred for (Lys).

Hydroxyl groups (OH) may be protected by a suitable protecting group selected from benzyl (Bzl), 2,6 dichlorobenztl (2,6 diCl-Bzl), and tert. Butyl (t-Bu), (tBu) is most preferred for (Tyr), (Ser) and (Thr).

The β- and γ-amide groups may be protected by a suitable protecting group selected from 4-methyltrityl (Mtt), 2,4,6-trimethoxybenzyl (Tmob), 4,4-DimethoxydityIBis-(4-methoxyphenyl)-methyl (Dod) and Trityl (Trt). Trt is the most preferred for (Asn) and (Gln).

The indole group may be protected by a suitable protecting group selected from formyl (For), Mesityl-2-sulfonyl (Mts) and t-butyloxycarbonyl (Boc). Boc is the most preferred for (Trp).

The imidazol group may be protected by a suitable protecting group selected from Benzyl (Bzl), -t-butyloxycarbonyl (Boc), and Trityl (Trt). Trt is the most preferred for (His).

All solvents, isopropanol (iPrOH), methylene chloride $(CH_2Cl_2)$, dimethylformamide (DMF) and N-methylpyrrolinone (NMP) were purchased from Fisher or Burdick & Jackson and were used without additional distillation. Trifluoroacetic acid was purchased from Halocarbon or Fluka and used without further purification.

Diisopropylcarbodiimide (DIC) and diisopropylethylamine (DIPEA) was purchased from Fluka or Aldrich and used without further purification. Hydroxybenzotriazole (HOBT) dimethylsulfide (DMS) and 1,2-ethanedithiol (EDT) were purchased from Sigma Chemical Co. and used without further purification. Protected amino acids were generally of the L configuration and were obtained commercially from Bachem, or Neosystem. Purity of these reagents was confirmed by thin layer chromatography, NMR and melting point prior to use. Benzhydrylamine resin (BHA) was a copolymer of styrene-1% divinylbenzene (100-200 or 200-400 mesh) obtained from Bachem or Advanced Chemtech. Total nitrogen content of these resins were generally between 0.3-1.2 meq/g.

High performance liquid chromatography (HPLC) was conducted on a LDC apparatus consisting of Constametric I and III pumps, a Gradient Master solvent programmer and mixer, and a Spectromonitor III variable wavelength UV detector. Analytical HPLC was performed in reversed phase mode using Vydac $C_{18}$ columns (0.4×30 cm). Preparative HPLC separations were run on Vaydac columns (2×25 cm).

In a preferred embodiment, peptides were prepared using solid phase synthesis by the method generally described by Merrifield, (J. Amer. Chem. Soc., 85, 2149 (1963)), although other equivalent chemical synthesis known in the art could be used as previously mentioned. Solid phase synthesis is commenced from the C-terminal end of the peptide by coupling a protected alpha-amino acid to a suitable resin. Such a starting material can be prepared by attaching an alpha-amino-protected amino acid by an ester linkage to a p-benzyloxybenzyl alcohol (Wang) resin, or by an amide bond between an Fmoc-Linker, such as p-((R,S)-α-(1-(9H-fluoren-9-yl)-methoxyformamido)-2,4-dimethoxybenzyl)-phenoxyacetic acid (Rink linker) to a benzhydrylamine (BHA) resin. Preparation of the hydroxymethyl resin is well known in the art. Fmoc-Linker-BHA resin supports are commercially available and generally used when the desired peptide being synthesized has an unsubstituted amide at the C-terminus.

Typically, the amino acids or mimetic are coupled onto the Fmoc-Linker-BHA resin using the Fmoc protected form of amino acid or mimetic, with 2-5 equivalents of amino acid and a suitable coupling reagent. After couplings, the resin may be washed and dried under vacuum. Loading of the amino acid onto the resin may be determined by amino acid analysis of an aliquot of Fmoc-amino acid resin or by determination of Fmoc groups by UV analysis. Any unreacted amino groups may be capped by reacting the resin with acetic anhydride and diisopropylethylamine in methylene chloride.

The resins are carried through several repetitive cycles to add amino acids sequentially. The alpha amino Fmoc protecting groups are removed under basic conditions. Piperidine, piperazine or morpholine (20-40% v/v) in DMF may be used for this purpose. Preferably 40% piperidine in DMF is utilized Following the removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. For example, appropriate reagents for such syntheses are benzotriazol-1-yloxy-tri-(dimethylamino) phosphonium hexafluorophosphate (BOP), Bromo-tris-pyrrolidino-phosphonium hexafluorophosphate (PyBroP) 2-(1H-Benzotriazole-1-yl)-1,1,3,3-tetramethyluronium hexafluorophosphate (HBTU), and diisopropylcarbodiimide (DIC). Preferred here are HBTU and DIC. Other activating agents are described by Barany and Merrifield (in The Peptides, Vol. 2, J. Meienhofer, ed., Academic Press, 1979, pp 1-284) may be utilized. Various reagents such as 1 hydroxybenzotriazole (HOBT), N-hydroxysuccinimide (HOSu) and 3,4-dihydro-3-hydroxy-4-oxo-1,2,3-benzotriazine (HOOBT) may be added to the coupling mixtures in order to optimize the synthetic cycles. Preferred here is HOBT.

The protocol for a typical synthetic cycle is as follows:

Protocol 1

| Step | Reagent | Time |
| --- | --- | --- |
| 1 | DMF | 2 × 30 sec |
| 2 | 20% piperidine/DMF | 1 min |
| 3 | 20% piperidine/DMF | 15 min |
| 4 | DMF | 2 × 30 sec |
| 5 | iPrOH | 2 × 30 sec |
| 6 | DMF | 3 × 30 sec |
| 7 | coupling | 60 min–18 hours |
| 8 | DMF | 2 × 30 sec |
| 9 | iPrOH | 1 × 30 sec |
| 10 | DMF | 1 × 30 sec |
| 11 | $CH_2Cl_2$ | 2 × 30 sec |

Solvents for all washings and couplings were measured to volumes of 10-20 ml/g resins. Coupling reactions throughout the synthesis were monitored by the Kaiser Ninhydrin test to determine extent of completion (Kaiser et at. Anal. Biochem. 34, 595-598 (1970)). Slow reaction kinetics was observed for Fmoc-Arg (Pmc) and for couplings to secondary amines by sterically hindered acids. Any incomplete coupling reactions were either recoupled with freshly prepared activated amino acid or capped by treating the peptide resin with acetic anhydride as described above. The fully assembled peptide-resins were dried in vacuum for several hours.

For each compound, the blocking groups were removed and the peptide cleaved from the resin. For example, the peptide-resins were treated with 100 μL ethanedithiol, 100 μl dimethylsulfide, 300 μL anisole, and 9.5 mL trifluoroacetic acid, per gram of resin, at room temperature for 180 min. Or alternately the peptide-resins were treated with 1.0 mL triisopropyl silane and 9.5 mL trifluoroacetic acid, per gram of resin, at room temperature for 180 min. The resin is filtered off and the filtrates are precipitated in chilled ethyl ether. The precipitates are centrifuged and the ether layer is decanted. The residue was washed with two or three volumes of $Et_2O$ and recentrifuged. The crude products were dried under vacuum.

Purification of the crude peptides were performed on Shimadzu LC-8A system by high performance liquid chromatography (HPLC) on a reverse phase Vydac C-18 Column (50×250 mm. 300 A, 10-15 μm). The peptides were injected to the columns in a minimum volume of either 0.1 AcOH/$H_2O$ or CH3CH/$H_2O$. Gradient elution was generally started at 2% B buffer, 2% -70% B over 70 minutes, (buffer A: 0.1% TFA/$H_2O$, buffer B: 0.1% TFA/$CH_3CN$) at a flow rate of 50 ml/min. UV detection was made at 220/280 nm. The fractions containing the products were separated and their purity was judged on Shimadzu LC-10AT analytical system using reverse phase Ace C18 column (4.6×50 mm) at a flow rate of 2 ml/min., gradient (2-70%) over 10 min. (buffer A: 0.1% TFA/$H_2O$, buffer B: 0.1% TFA/$CH_3CN$)). Fractions judged to be of high purity were pooled and lyophilized.

Purity of the final products was checked by analytical HPLC on a reversed phase column as stated above. Purity of all products was judged to be approximately 95-99%. All final products were also subjected to fast atom bombardment mass spectrometry (FAB-MS) or electrospray mass spectrometry (ES-MS). All products yielded the expected parent M+H ions within acceptable limits.

Agonists of Y2R cause reduction of food intake in mouse models of human obesity. Therefore, administration of these compounds agonize Y2 receptor activity, which is important for the reduction of food intake and regulation of body weight. According to the in vivo activity experiments in Example 78, reduction of food intake was demonstrated for selected analogs of the invention (those of Examples 5, 44, 73 and 74) and the results summarized in FIGS. 7, 8, 9 and 10.

The compounds of the present invention can be provided in the form of pharmaceutically acceptable salts. Examples of preferred salts are those formed with pharmaceutically acceptable organic acids, e.g., acetic, lactic, maleic, citric, malic, ascorbic, succinic, benzoic, salicylic, methanesulfonic, toluenesulfonic, trifluoroacetic, or pamoic acid, as well as polymeric acids such as tannic acid or carboxymethyl cellulose, and salts with inorganic acids, such as hydrohalic acids (e.g., hydrochloric acid), sulfuric acid, or phosphoric acid and the like. Any procedure for obtaining a pharmaceutically acceptable salt known to a skilled artisan can be used.

In the practice of the method of the present invention, an effective amount of any one of the peptides of this invention or a combination of any of the peptides of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Thus, the method of the present invention is practiced when relief of symptoms is specifically required or perhaps imminent. Alternatively, the method of the present invention is effectively practiced as continuous or prophylactic treatment.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as an "effective amount". For example, the dose for intranasal administration is typically in the range of about 1 to about 100 mg/kg body weight; and the dose for subcutaneous administration is typically in the range of about 0.001 to about 50 mg/kg body weight.

Preferably, the dose of a compound of the present invention is from about 2.5 to about 10 mg/kg. Most preferably, the dosages are about 2.5, about 5 and about 10 mg/kg.

The invention will now be further described in the Examples which follow, which are intended as an illustration only and do not limit the scope of the invention.

EXAMPLES

Example 1

Preparation of Fmoc-Linker-BHA Resin

Benzhydrylamine copolystyrene-1% divinylbenzene cross-linked resin (10.0 g, 9.3 mequiv, 100-200 ASTM mesh, Advanced ChemTech) was swelled in 100 mL CH2Cl2, filtered and washed successively with 100 ml each of $CH_2Cl_2$, 6% $DIPEA/CH_2Cl_2$ (two times), $CH_2Cl_2$ (two times). The resin was treated with p-((R,S)-α-(1-(9H-fluoren-9-yl)-methoxyformamido)-2,4-dimethoxybenzyl)-phenoxyacetic acid (Fmoc-Linker) (7.01 g, 13.0 mmole), N-hydroxybenzotriazole (2.16 g, 16.0 mmole), and diisopropyl-carbodiimide (2.04 ml, 13.0 mmol) in 100 mL 25% $DMF/CH_2Cl_2$ for 24 hours at room temperature. The resin was filtered and washed successively with 100 ml each of $CH_2Cl_2$ (two times), isopropanol (two times), DMF, and $CH_2Cl_2$ (three times). A Kaiser Ninhydrin analysis was negative. The resin was dried under vacuum to yield 16.12 g of Fmoc-Linker-BHA resin. A portion of this resin (3.5 mg) was subjected to Fmoc deprotection and quantitative UV analysis which indicated a loading of 0.56 mmol/g.

Example 2

Protocol for the Synthesis of Peptides by Applied Biosystem 433A Synthesizer Using Fluorenylmethyloxycarbonyl (Fmoc) Chemistry For a 0.25 mmol scale peptide synthesis by Applied Biosystem 433A synthesizer (Foster City, Calif.), the FastMoc 0.25 mmole cycles were used with either the resin sampling or non resin sampling, 41 mL reaction vessel. The Fmoc-amino acid resin was dissolved with 2.1 g NMP, 2 g of 0.45M HOBT/HBTU in DMF and 2M DIEA, then transferred to the reaction vessel.

The basic FastMoc coupling cycle was represented by the module "BADEIFD," wherein each letter represents a module. For example:

B represents the module for Fmoc deprotection using 20% Piperidine/NMP and related washes and readings for 30 min (either UV monitoring or conductivity);

A represents the module for activation of amino acid in cartridges with 0.45 M HBTU/HOBt and 2.0 M DIEA and mixing with $N_2$ bubbling;

D represents the module for NMP washing of resin in the reaction vessel;

E represents the module for transfer of the activated amino acid to the reaction vessel for coupling;

I represents the module for a 10 minute waiting period with vortexing on and off of the reaction vessel; and F represents the module for cleaning cartridge, coupling for approximately 10 minutes and draining the reaction vessel.

Couplings were typically extended by addition of module "I" once or multiple times. For example, double couplings were run by performing the procedure "BADEIIADEIFD." Other modules were available such as c for methylene chloride washes and "C" for capping with acetic anhydride. Individual modules were also modifiable by, for example, changing the timing of various functions, such as transfer time, in order to alter the amount of solvent or reagents transferred.

The cycles above were typically used for coupling one amino acid. For synthesizing tetra peptides, however, the cycles were repeated and strung together. For example, BADEIIADEIFD was used to couple the first amino acid, followed by BADEIIADEIFD to couple the second amino acid, followed by BADEIIADEIFD to couple the third amino acid, followed by BADEIIADEIFD to couple the fourth amino acid, followed by BIDDcc for final deprotection and washing.

Example 3
Preparation of H-Tyr-Pro-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-NH$_2$ (PPY$_{1-36}$) (SEQ ID NO: 3)
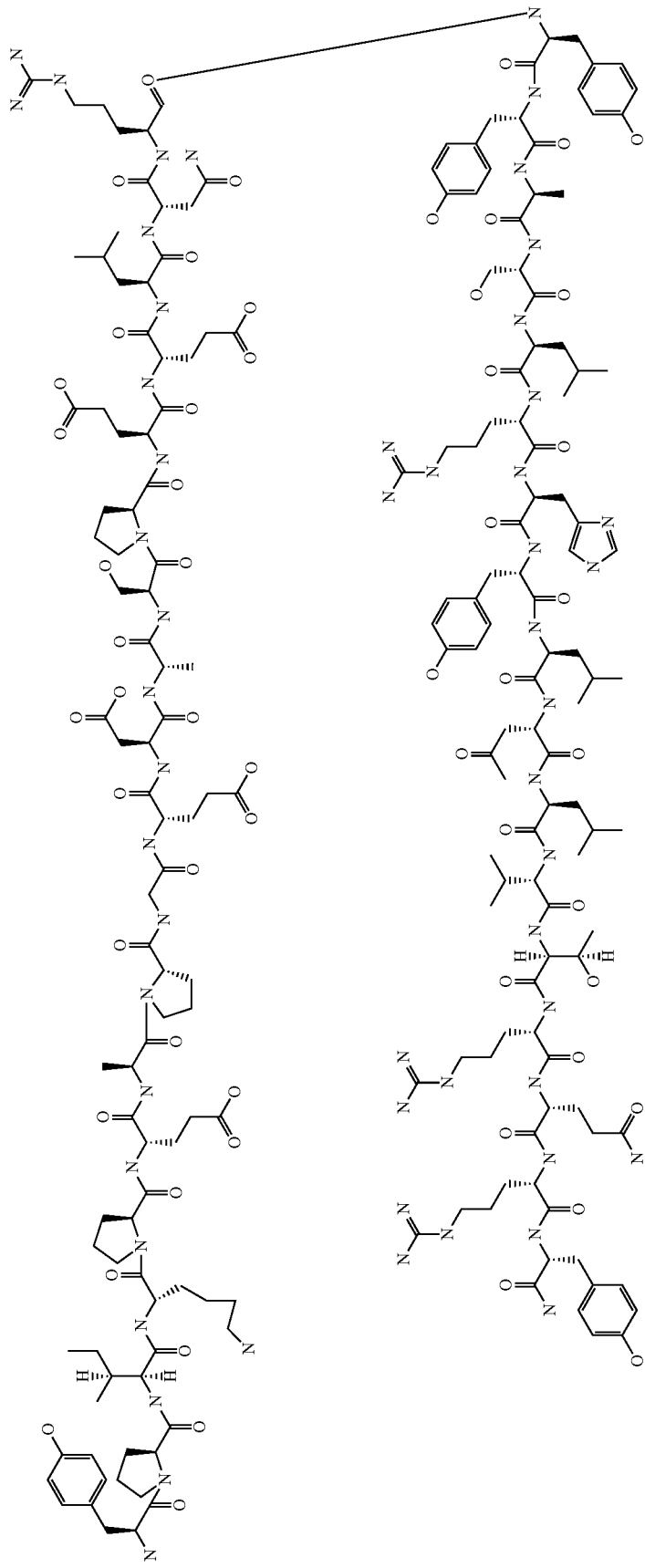

The above peptide was synthesized using Fmoc chemistry on an Applied Biosystem 433A synthesizer. The synthesizer was programmed for double coupling using the modules described in Example 2. The synthesis was carried out on a 0.25 mmol scale using the Fmoc-Linker-BHA resin (450 mg, 0.25 mmol) from Example 1. At the end of the synthesis, the resin was transferred to a reaction vessel on a shaker for cleavage. The peptide was cleaved from the resin using 13.5 mL 97% TFA/3% H2O and 1.5 mL triisopropylsilane for 180 minutes at room temperature. The deprotection solution was added to 100 mL cold $ET_2O$, and washed with 1 mL TFA and 30 mL cold $ET_2O$ to precipitate the peptide. The peptide was centrifuged 2×50 mL polypropylene tubes. The precipitates from the individual tubes were combined in a single tube and washed 3 times with cold $ET_2O$ and dried in a desiccator under house vacuum.

The crude material was purified by preparative HPLC on a Pursuit C18-Column (250×50 mm, 10 μm particle size) and eluted with a linear gradient of 2-70% B (buffer A: 0.1% TFA/H2O; buffer B: 0.1% TFA/CH3CN) in 90 min., flow rate 60 mL/min, and detection 220/280 nm. The fractions were collected and were checked by analytical HPLC. Fractions containing pure product were combined and lyophilized to yield 65 mg (6%) of a white amorphous powder. (ES)+- LCMS m/e calculated ("calcd") for $C_{194}H_{295}N_{55}O_{57}$ 4309.85, found 4309.15.

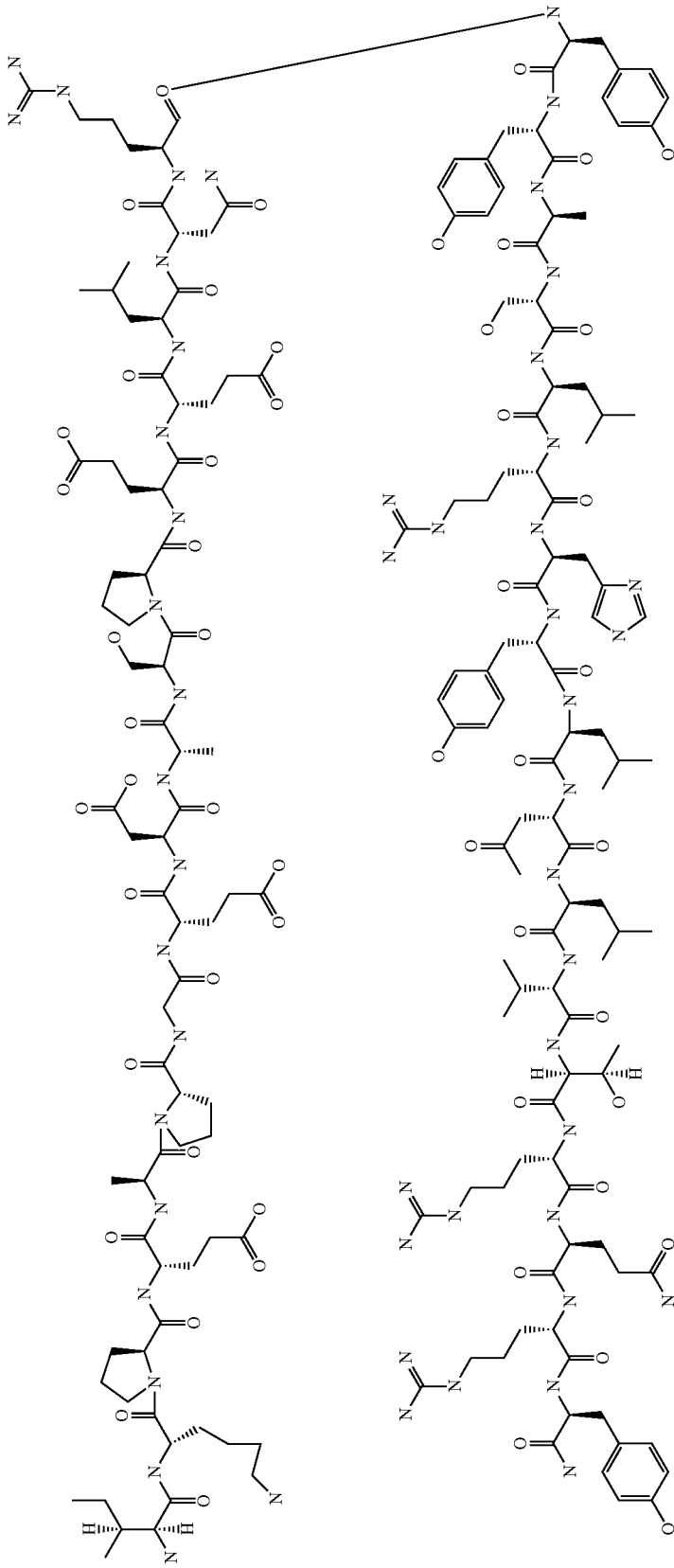
Example 4
Preparation of H-Ile-Lys-Pro-Glu-Ala-Pro-Gly-Glu-Asp-Ala-Ser-Pro-Glu-Glu-Leu-Asn-Arg-Tyr-Tyr-Ala-Ser-Leu-Arg-His-Tyr-Leu-Asn-Leu-Val-Thr-Arg-Gln-Arg-Tyr-NH2 (PYY3-36) (SEQ ID NO: 4)

Fmoc-Linker-BHA resin (450 mg, 0.25 mmol) from Example 1 was subjected to solid phase synthesis and purification by following the procedure in Example 3 to yield 151 mg (15%) of white amorphous powder. (ES)+-LCMS m/e calcd for $C_{180}H_{279}N_{53}O_{54}$ 4049.55 found 4050.40.
Example 5
Preparation of H-Ile-Lys-Pqa-Arg-His-Tyr-Leu-Asn-Leu-Val-Thr-Arg-Gln-Arg-Tyr-NH$_2$ (SEQ ID NO: 5)
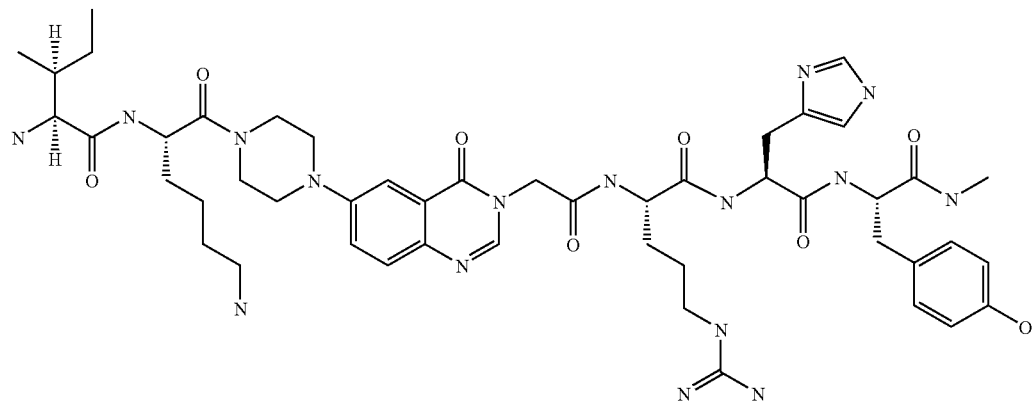
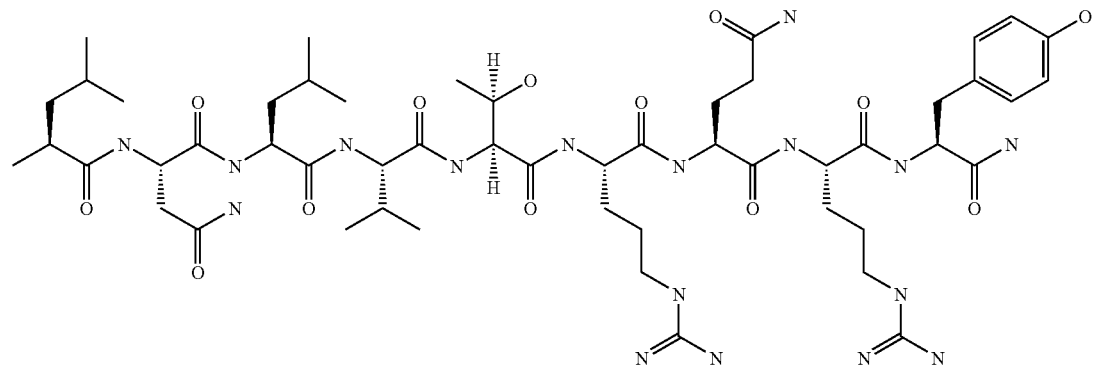

Fmoc-Linker-BHA resin (450 mg, 0.25 mmol) from Example 1 was subjected to solid phase synthesis and purification by following the procedure in Example 3 to yield 148 mg (9%) of white amorphous powder. (ES)+-LCMS m/e calcd for $C_{98}H_{155}N_{33}O_{21}$ 2131.53 found 2130.56.
Example 6
Preparation of Ac-Ile-Lys-Pqa-Arg-His-Tyr-Leu-Asn-Leu-Val-Thr-Arg-Gln-Arg-Tyr-NH$_2$ (SEQ ID NO: 5)
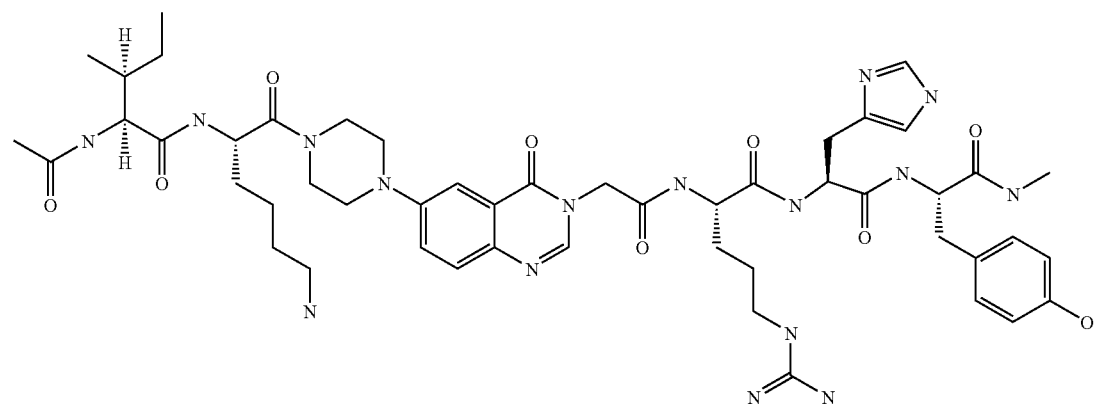
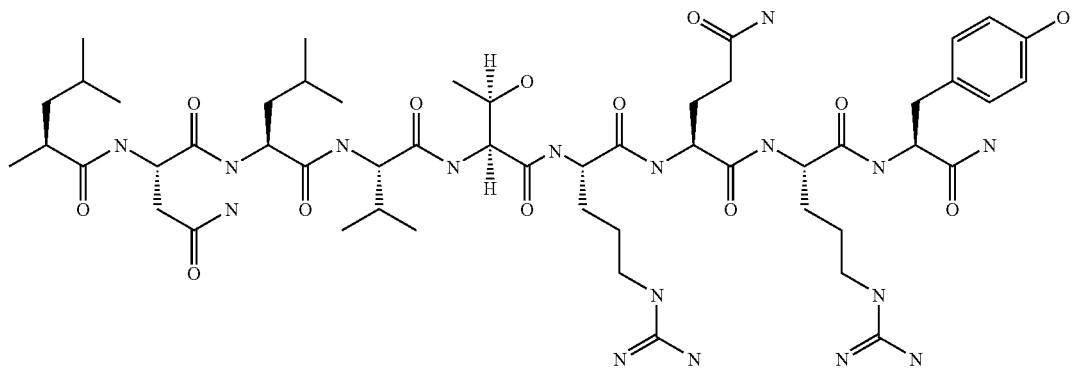

Fmoc-Linker-BHA resin (450 mg, 0.25 mmol) from Example 1 was subjected to solid phase synthesis (actylation cycle was added to the ABI-protocol) and the purification by following the procedure in Example 3 to yield 150 mg (27%) of white amorphous powder. (ES)+-LCMS m/e calcd for $C_{100}H_{157}N_{33}O_{22}$ 2171.57 found 2171.4.
Example 7
Preparation of H-Ile-Lys-Pqa-Arg-His-Tyr-Leu-Asn-Leu-Val-Thr-Arg-Ala-Arg-Tyr-NH$_2$ (SEQ ID NO: 6)
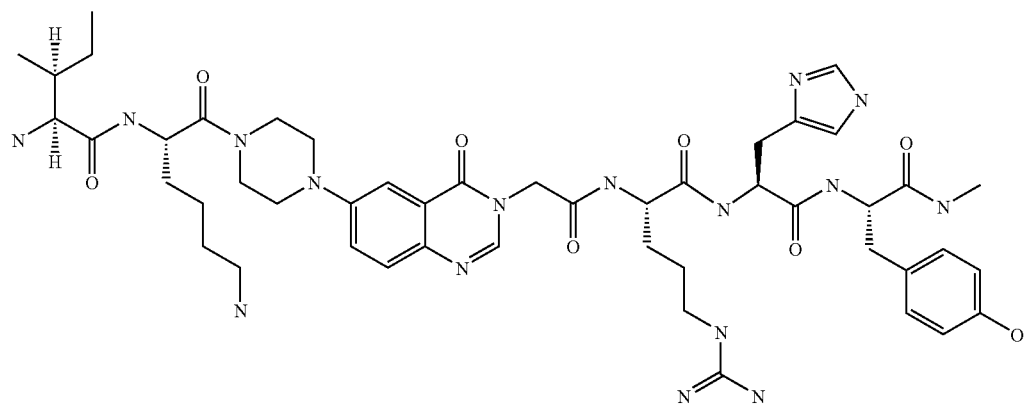
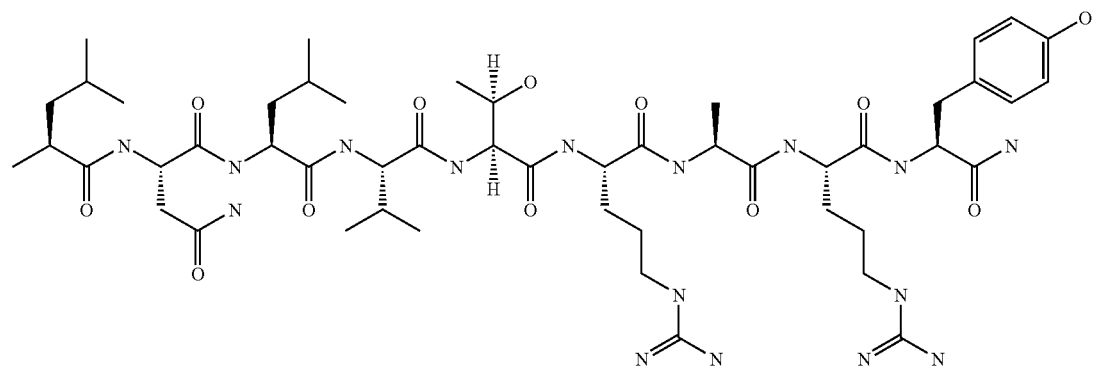

Fmoc-Linker-BHA resin (450 mg, 0.25 mmol) from Example 1 was subjected to solid phase synthesis (Ala was inserted in position 34 of the sequence) and purification by following the procedure in Example 3 to yield 142 mg (27%) of white amorphous powder. (ES)+-LCMS m/e calcd for $C_{96}H_{150}N_{32}O_{20}$ 2072.47 found 2072.4
Example 8
Preparation of H-Ile-Lys-Pqa-Arg-His-Tyr-Leu-Asn-Leu-Val-Ala-Arg-Gln-Arg-Tyr-NH$_2$ (SEQ ID NO: 7)
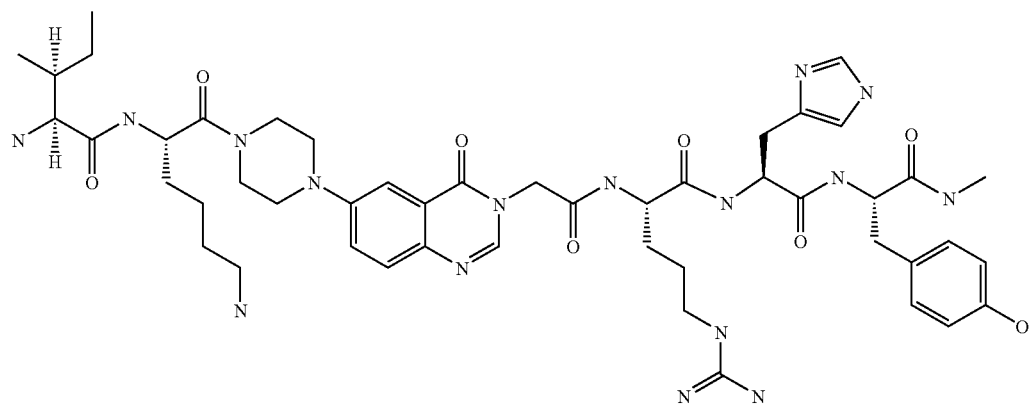
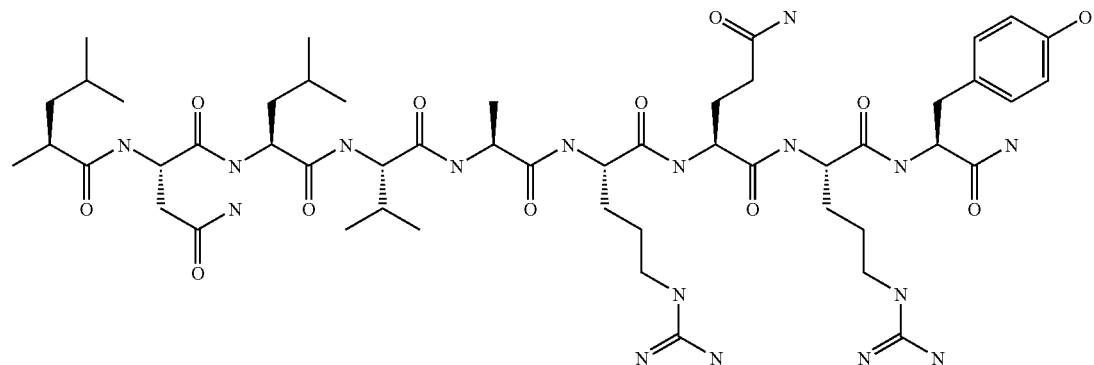

Fmoc-Linker-BHA resin (450 mg, 0.25 mmol) from Example 1 was subjected to solid phase synthesis (Ala was inserted in position 32 of the sequence) and purification by following the procedure in Example 3 to yield 167 mg (32%) of white amorphous powder. (ES)+-LCMS m/e calcd for $C_{97}H_{151}N_{33}O_{20}$ 2099.49 found 2100.3
Example 9
Preparation of H-Ile-Lys-Pqa-Arg-His-Tyr-Leu-Asn-Leu-Ala-Thr-Arg-Gln-Arg-Tyr-NH$_2$ (SEQ ID NO: 8)
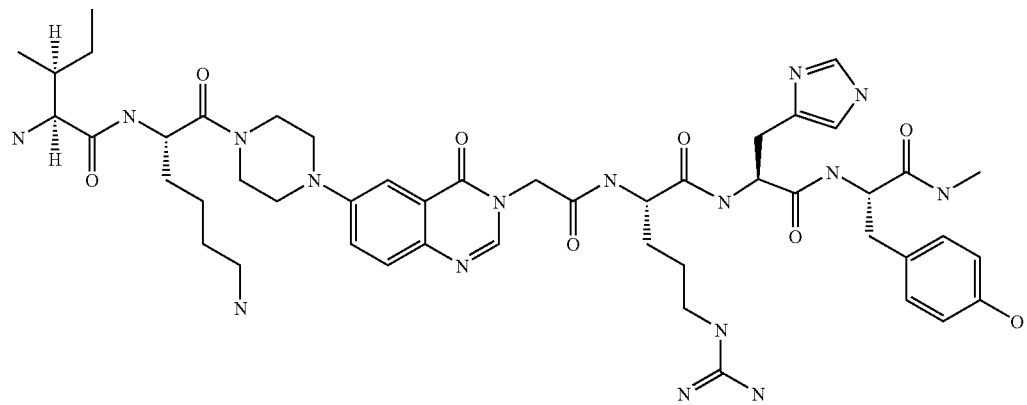
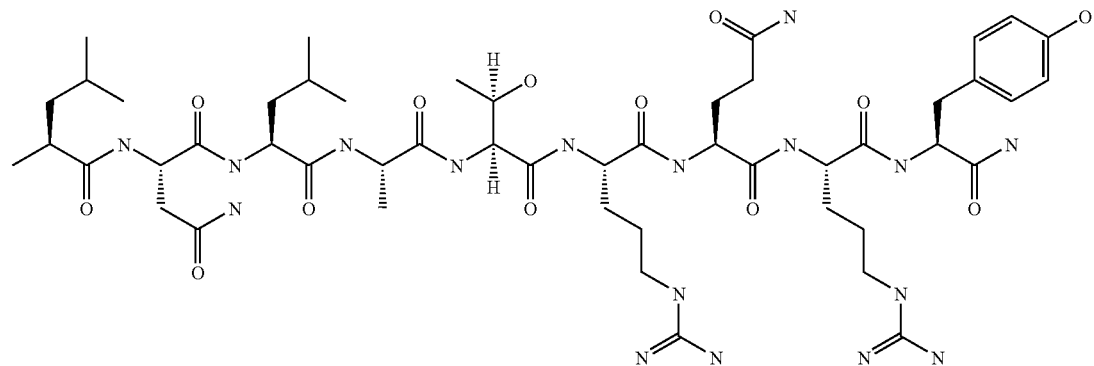

Fmoc-Linker-BHA resin (450 mg, 0.25 mmol) from Example 1 was subjected to solid phase synthesis (Ala was inserted in position 31 of the sequence) and purification by following the procedure in Example 3 to yield 105 mg (20%) of white amorphous powder. (ES)+-LCMS m/e calcd for $C_{96}H_{149}N_{33}O_{21}$ 2101.47 found 2102.1
Example 10
Preparation of H-Ile-Lys-Pqa-Arg-His-Tyr-Leu-Asn-Ala-Val-Thr-Arg-Gln-Arg-Tyr-NH$_2$ (SEQ ID NO: 9)
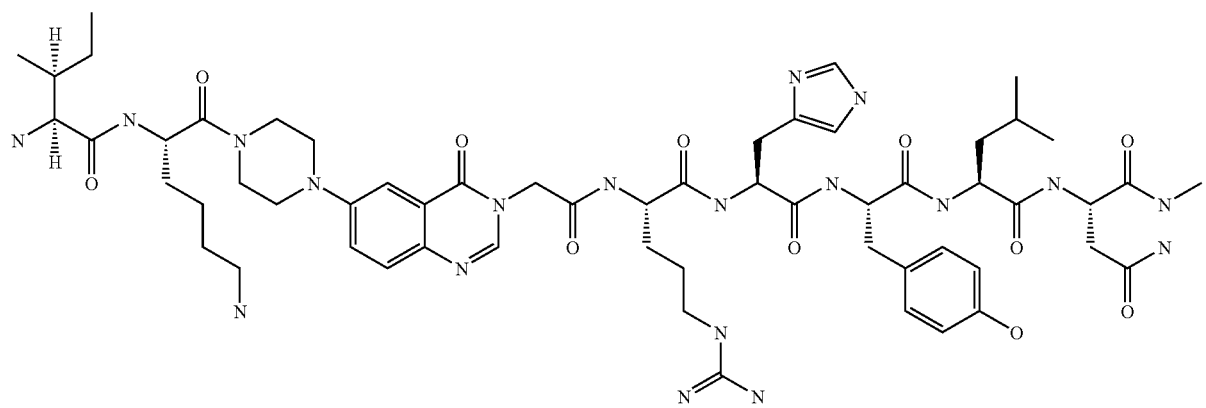
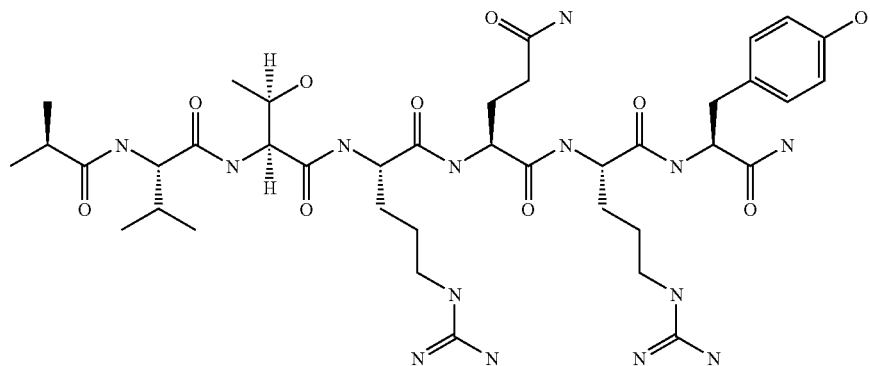

Fmoc-Linker-BHA resin (450 mg, 0.25 mmol) from Example 1 was subjected to solid phase synthesis (Ala was inserted in position 30 of the sequence) and purification by following the procedure in Example 3 to yield 167 mg (27%) of white amorphous powder. (ES)+-LCMS m/e calcd for $C_{95}H_{147}N_{33}O_{21}$ 2087.44 found 2087.7
Example 11
Preparation of H-Ile-Lys-Pqa-Arg-His-Tyr-Leu-Ala-Leu-Val-Thr-Arg-Gln-Arg-Tyr-NH$_2$ (SEQ ID NO: 10)
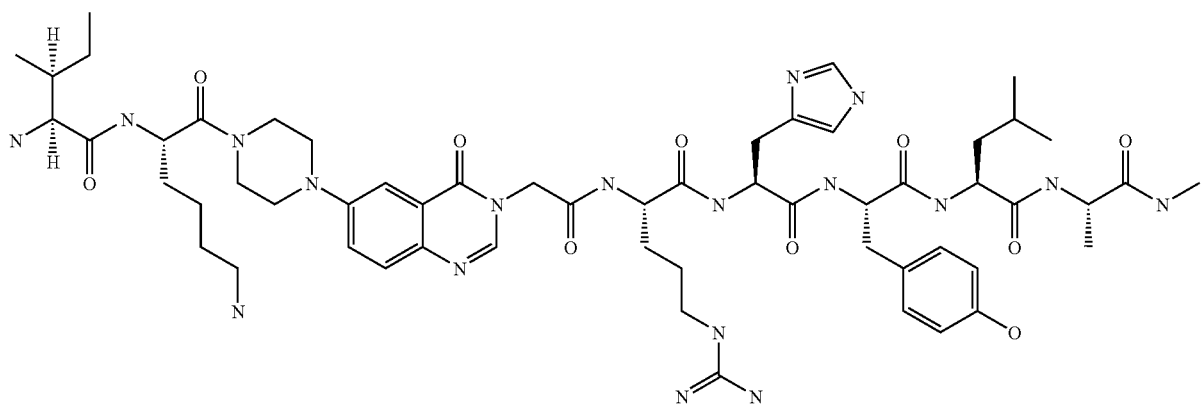
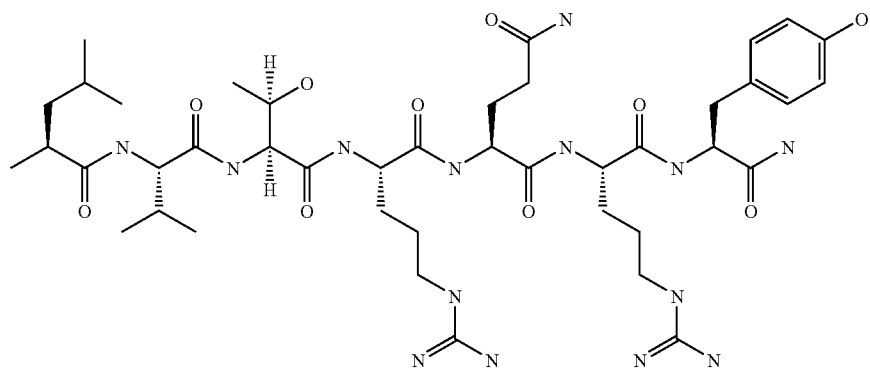

Fmoc-Linker-BHA resin (450 mg, 0.25 mmol) from Example 1 was subjected to solid phase synthesis (Ala was inserted in position 29 of the sequence) and purification by following the procedure in Example 3 to yield 142 mg (27%) of white amorphous powder. (ES)+-LCMS m/e calcd for $C_{97}H_{152}N_{32}O_{20}$ 2086.50 found 2086.50.
Example 12
Preparation of H-Ile-Lys-Pqa-Arg-His-Tyr-Ala-Asn-Leu-Val-Thr-Arg-Gln-Arg-Tyr-NH$_2$ (SEQ ID NO: 11)
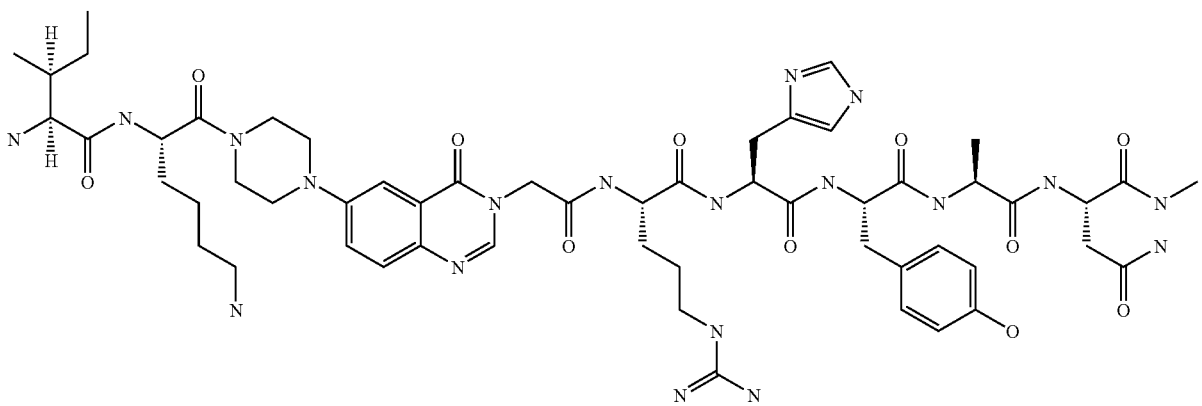
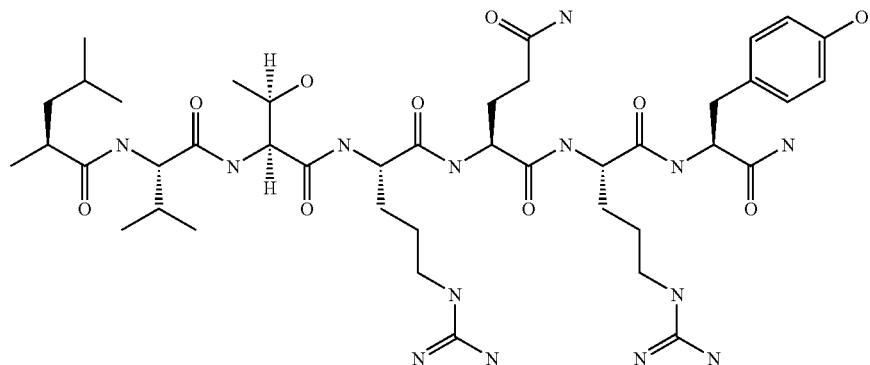

Fmoc-Linker-BHA resin (450 mg, 0.25 mmol) from Example 1 was subjected to solid phase synthesis (Ala was inserted in position 28 of the sequence) and purification by following the procedure in Example 3 to yield 164 mg (31%) of white amorphous powder. (ES)+-LCMS m/e calcd for $C_{95}H_{147}N_{33}O_{21}$ 2087.44 found 2087.40.
Example 13
Preparation of H-Ile-Lys-Pqa-Arg-His-Ala-Leu-Asn-Leu-Val-Thr-Arg-Gln-Arg-Tyr-NH$_2$ (SEQ ID NO: 12)
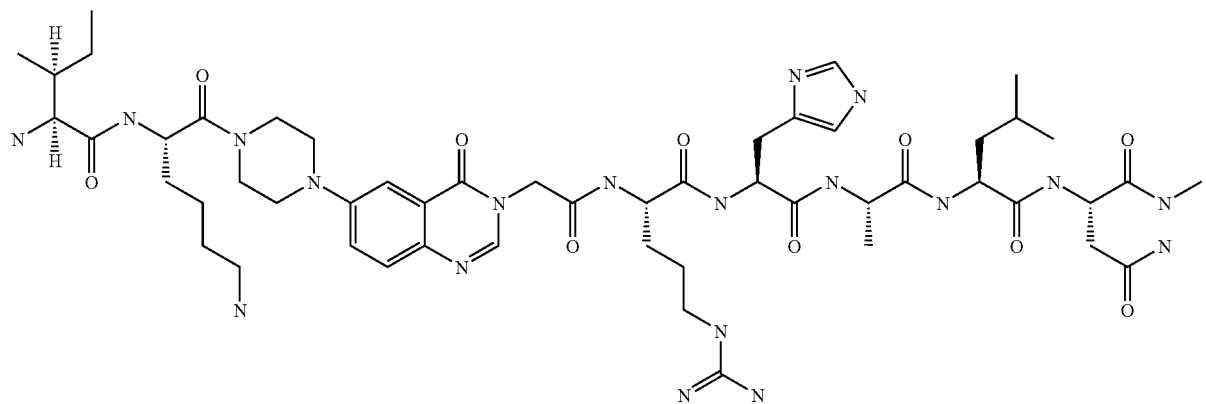
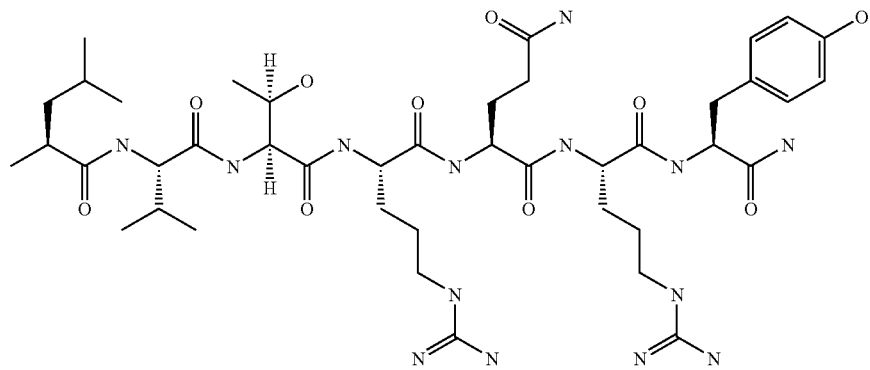

Fmoc-Linker-BHA resin (450 mg, 0.25 mmol) from Example 1 was subjected to solid phase synthesis (Ala was inserted in position 27 of the sequence) and purification by following the procedure in Example 3 to yield 132 mg (26%) of white amorphous powder. (ES)+-LCMS m/e calcd for $C_{92}H_{149}N_{33}O_{20}$ 2037.42 found 2037.60.

Example 14

Preparation of H-Ile-Lys-Pqa-Arg-Ala-Tyr-Leu-Asn-Leu-Val-Thr-Arg-Gln-Arg-Tyr-NH$_2$ (SEQ ID NO: 13)

Fmoc-Linker-BHA resin (450 mg, 0.25 mmol) from Example 1 was subjected to solid phase synthesis (Ala was inserted in position 26 of the sequence) and purification by following the procedure in Example 3 to yield 76 mg (15%) of white amorphous powder. (ES)+-LCMS m/e calcd for $C_{95}H_{151}N_{31}O_{21}$ 2063.46 found 2064.0

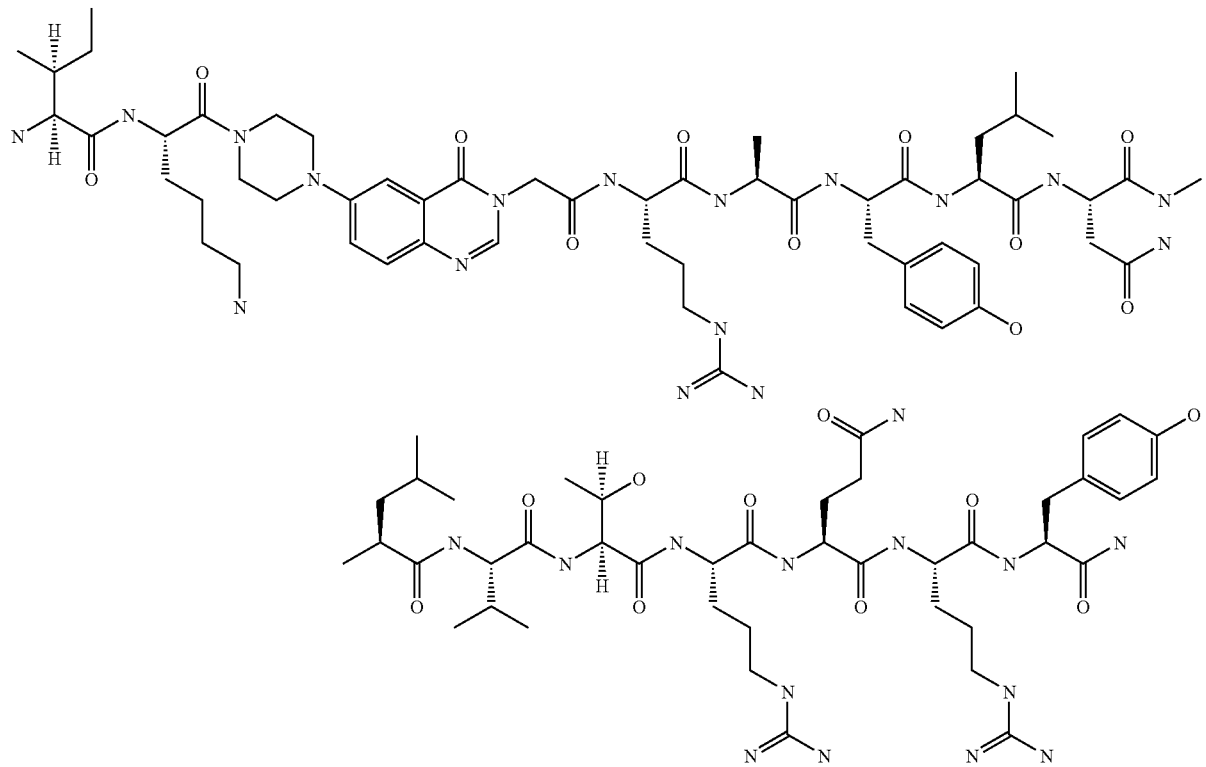

Example 15

Preparation of H-Ile-Lys-Pqa-Ala-His-Tyr-Leu-Asn-Leu-Val-Thr-Arg-Gln-Arg-Tyr-NH$_2$ (SEQ ID NO: 14)

-continued
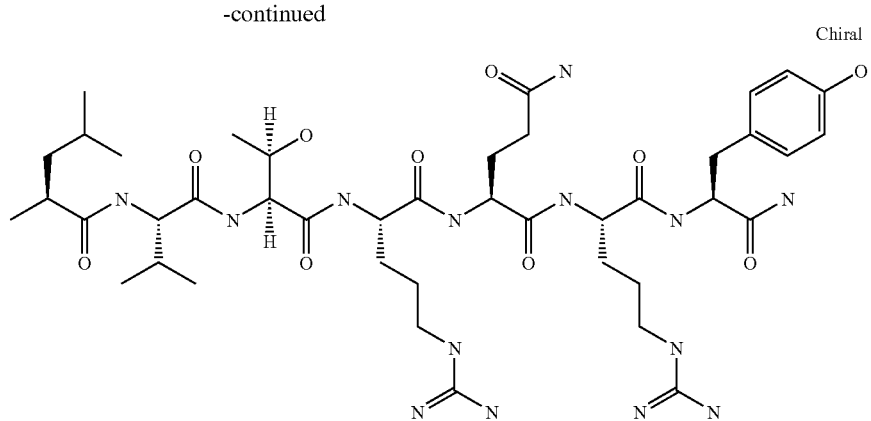
Fmoc-Linker-BHA resin (450 mg, 0.25 mmol) from Example 1 was subjected to solid phase synthesis (Ala was inserted in position 25 of the sequence) and purification by following the procedure in Example 3 to yield 152 mg (30%) of white amorphous powder. (ES)+-LCMS m/e calcd for $C_{95}H_{146}N_{30}O_{21}$ 2043.13 found 2043.4.
Example 16
Preparation of H-Ile-Ala-Pqa-Arg-His-Tyr-Leu-Asn-Leu-Val-Thr-Arg-Gln-Arg-Tyr-NH$_2$ (SEQ ID NO: 5)
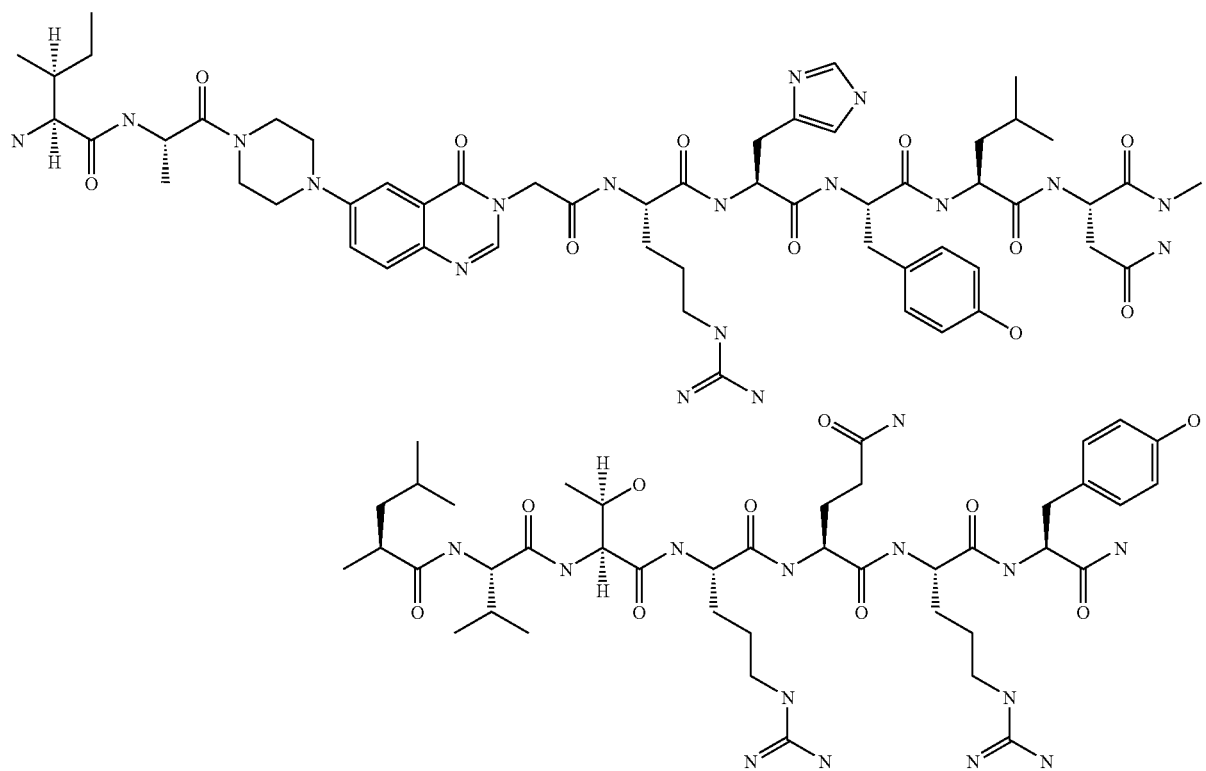

Fmoc-Linker-BHA resin (450 mg, 0.25 mmol) from Example 1 was subjected to solid phase synthesis (Ala was inserted in position 4 of the sequence) and purification by following the procedure in Example 3 to yield 72 mg (14%) of white amorphous powder. (ES)+-LCMS m/e calcd for $C_{95}H_{146}N_{32}O_{21}$ 2072.44 found 2071.2

Fmoc-Linker-BHA resin (450 mg, 0.25 mmol) from Example 16 was subjected to solid phase synthesis, wherein an acylation cycle was added to the protocol, and purification by following the procedure in Example 3 to yield 234 mg (44%) of white amorphous powder. (ES)+-LCMS m/e calcd for $C_{97}H_{148}N_{32}O_{22}$ 2114.46 found 2114.7.

Example 17

Preparation of Ac-Ile-Ala-Pqa-Arg-His-Tyr-Leu-Asn-Leu-Val-Thr-Arg-Gln-Arg-Tyr-NH$_2$ (SEQ ID NO: 5)

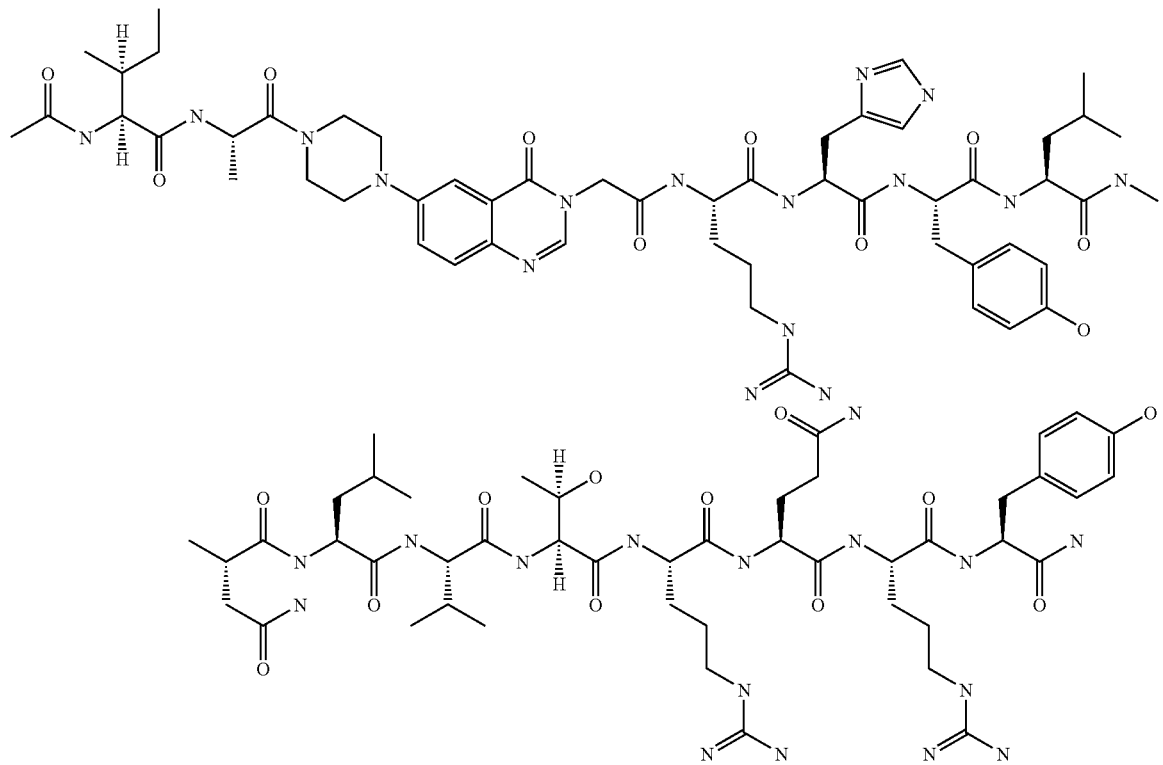

Example 18

Preparation of H-Ala-Lys-Pqa-Arg-His-Tyr-Leu-Asn-Leu-Val-Thr-Arg-Gln-Arg-Tyr-NH$_2$ (SEQ ID NO: 5)

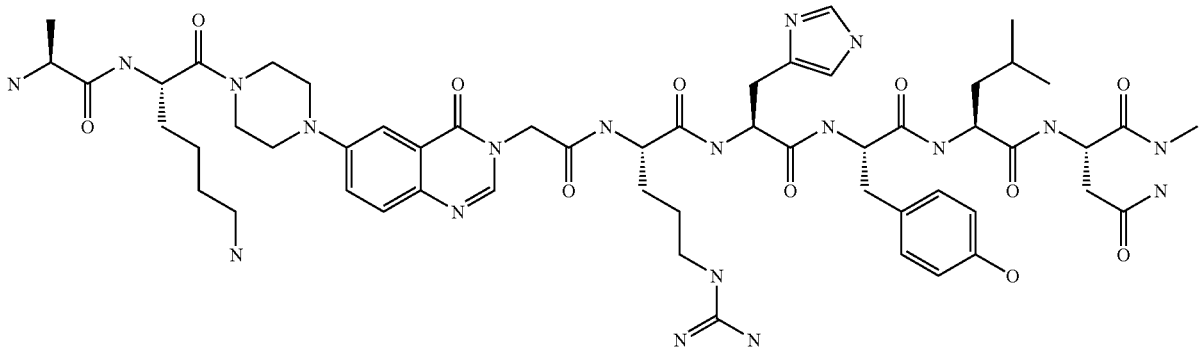

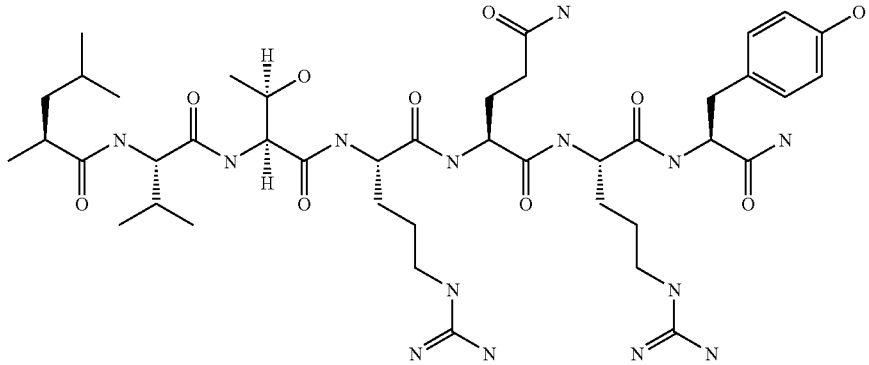

Fmoc-Linker-BHA resin (450 mg, 0.25 mmol) from Example 1 was subjected to solid phase synthesis (Ala was inserted in position 3 of the sequence) and purification by following the procedure in Example 3 to yield 196 mg (38%) of white amorphous powder. (ES)+-LCMS m/e calcd for $C_{95}H_{147}N_{33}O_{21}$ 2087.45 found 2086.5.

Fmoc-Linker-BHA resin (450 mg, 0.25 mmol) from Example 1 was subjected to solid phase synthesis ((D) Tyr was inserted in position 36 of the sequence) and purification by following the procedure in Example 3 to yield 114 mg (21%) of white amorphous powder. (ES)+-LCMS m/e calcd for $C_{98}H_{153}N_{33}O_{21}$ 2129.52 found 2129.10.

Example 19

Preparation of H-Ile-Lys-Pqa-Arg-His-Tyr-Leu-Asn-Leu-Val-Thr-Arg-Gln-Arg-(D)Tyr-NH$_2$

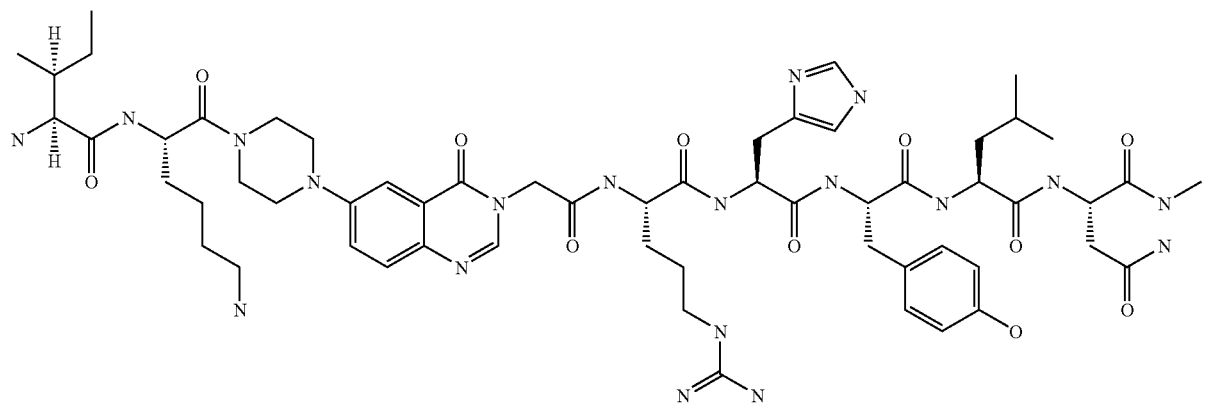

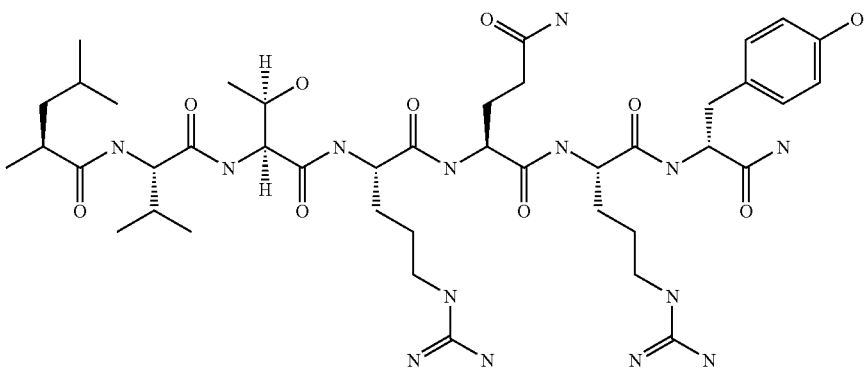

Example 20

Preparation of H-Ile-Lys-Pqa-Arg-His-Tyr-Leu-Asn-Leu-Val-Thr-Arg-Gln-(D)Arg-Tyr-NH$_2$

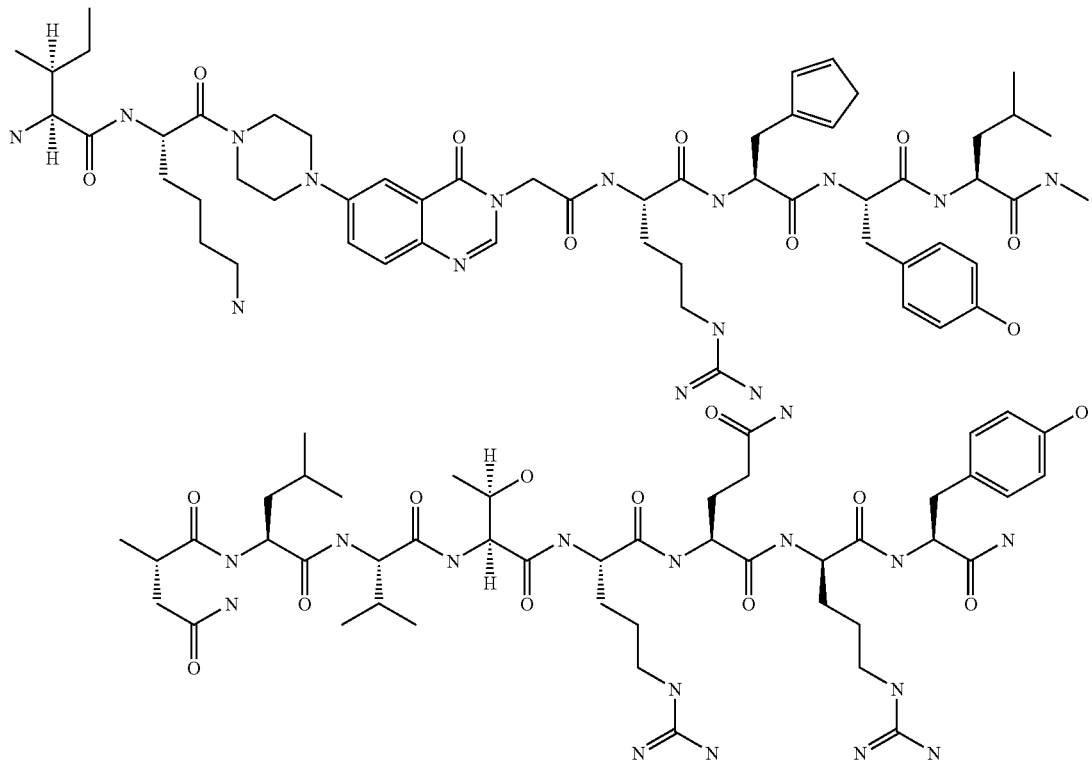

Fmoc-Linker-BHA resin (450 mg, 0.25 mmol) from Example 1 was subjected to solid phase synthesis ((D) Arg was inserted in position 35 of the sequence) and purification by following the procedure in Example 3 to yield 221 mg (42%) of white amorphous powder. (ES)+-LCMS m/e calcd for C$_{98}$H$_{153}$N$_{33}$O$_{21}$ 2129.52 found 2129.10.

Example 21

Preparation of H-Ile-Lys-Pqa-Arg-His-Tyr-Leu-Asn-Leu-Val-Thr-(D)Arg-Gln-Arg-Tyr-NH$_2$

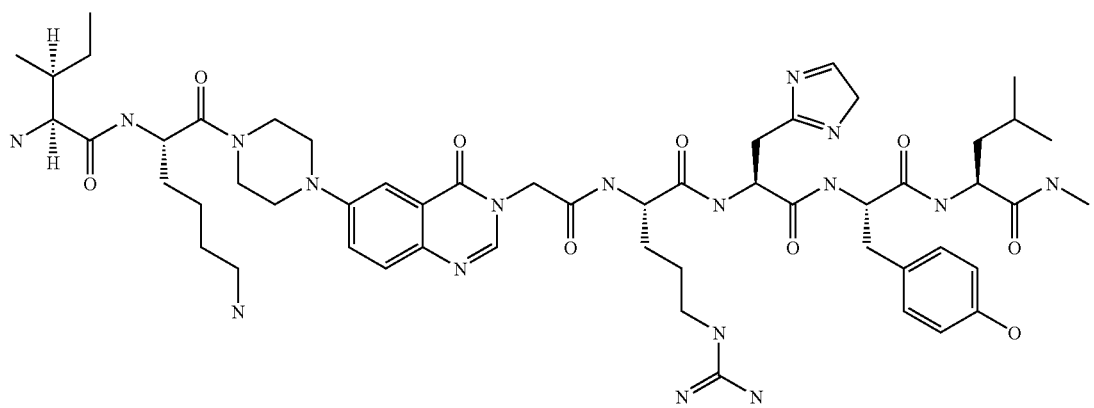

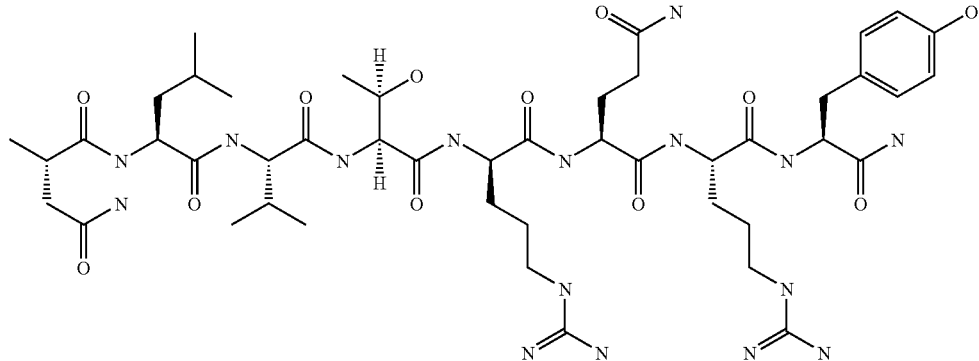

Fmoc-Linker-BHA resin (450 mg, 0.25 mmol) from Example 1 was subjected to solid phase synthesis ((D) Arg was inserted in position 33) of the sequence and purification by following the procedure in Example 3 to yield 174 mg (32%) of white amorphous powder. (ES)+-LCMS m/e calcd for $C_{98}H_{153}N_{33}O_{21}$ 2129.52 found 2128.4.

Fmoc-Linker-BHA resin (450 mg, 0.25 mmol) from Example 1 was subjected to solid phase synthesis ((D) Val was inserted in position 31 of the sequence) and purification by following the procedure in Example 3 to yield 67 mg (12%) of white amorphous powder. (ES)+-LCMS m/e calcd for $C_{98}H_{153}N_{33}O_{21}$ 2129.52 found 2129.10.

Example 22

Preparation of H-Ile-Lys-Pqa-Arg-His-Tyr-Leu-Asn-Leu-(D)Val-Thr-Arg-Gln-Arg-Tyr-NH$_2$

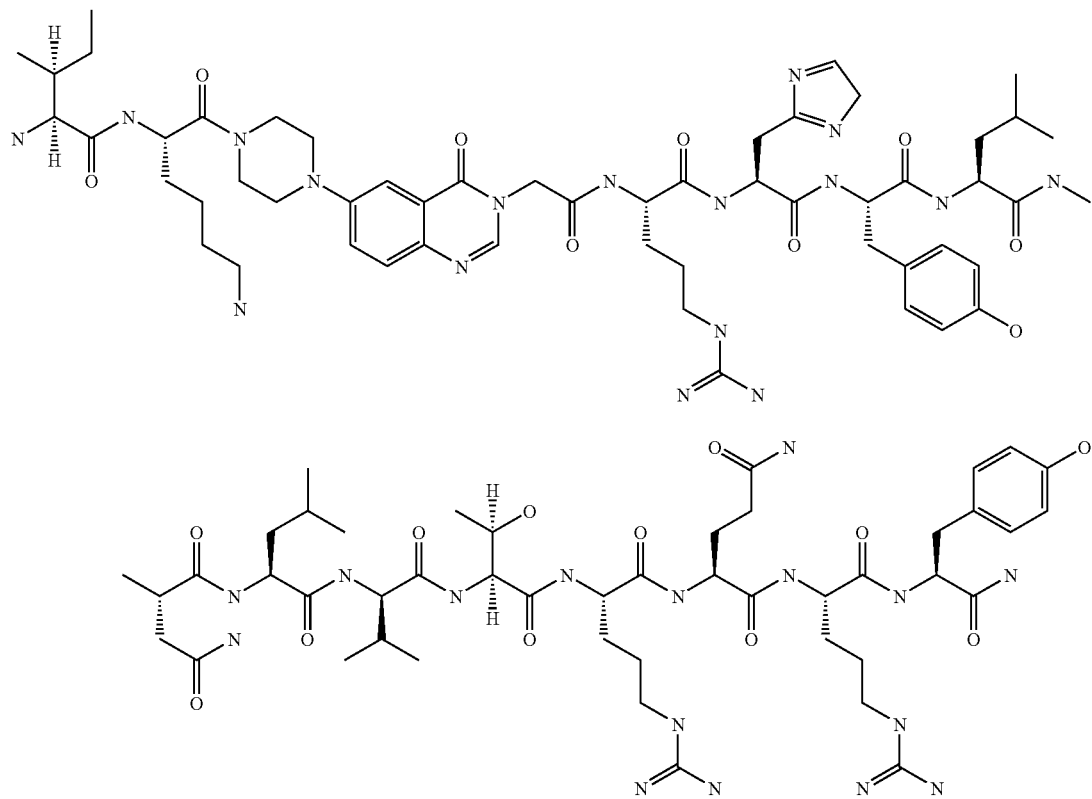

Example 23

Preparation of H-Ile-Lys-Pqa-Arg-His-Tyr-Leu-Asn-(D)Leu-Val-Thr-Arg-Gln-Arg-Tyr-NH$_2$

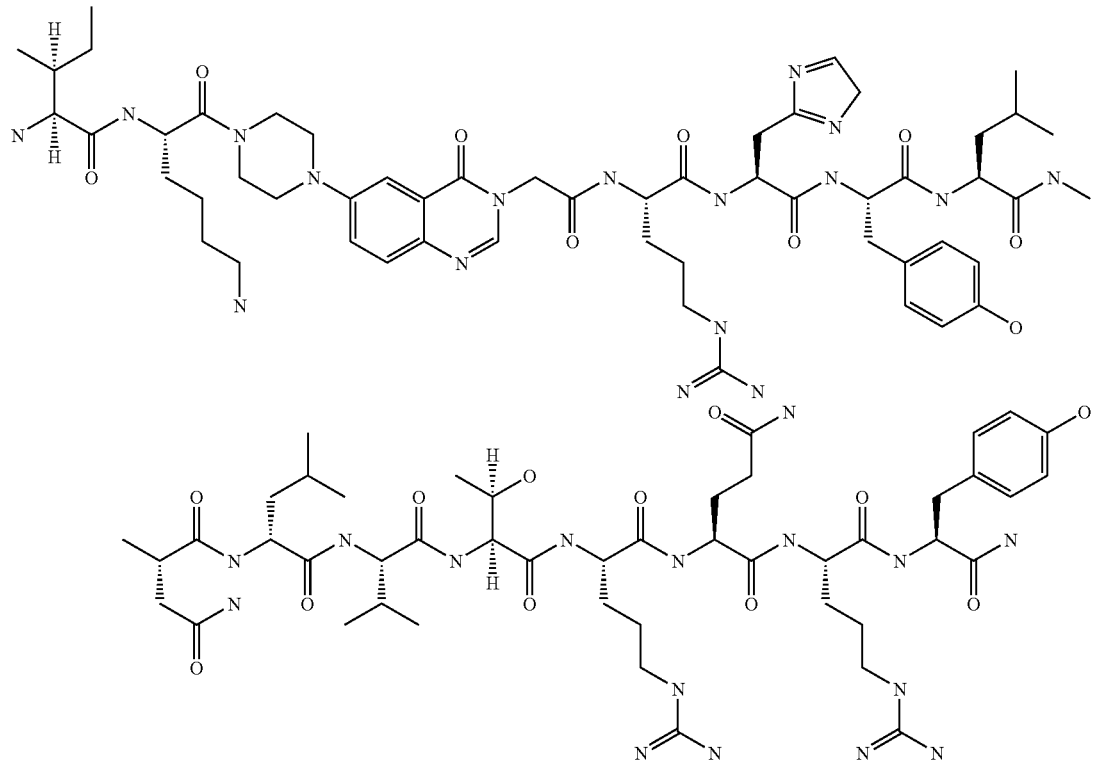

Fmoc-Linker-BHA resin (450 mg, 0.25 mmol) from Example 1 was subjected to solid phase synthesis ((D) Leu was inserted in position 30 of the sequence) and purification by following the procedure in Example 3 to yield 190 mg (36%) of white amorphous powder. (ES)+-LCMS m/e calcd for $C_{98}H_{153}N_{33}O_{21}$ 2129.52 found 2129.10.

Example 24

Preparation of H-Ile-Lys-Pqa-Arg-His-Tyr-Leu-(D))Asn-Leu-Val-Thr-Arg-Gln-Arg-Tyr-NH$_2$

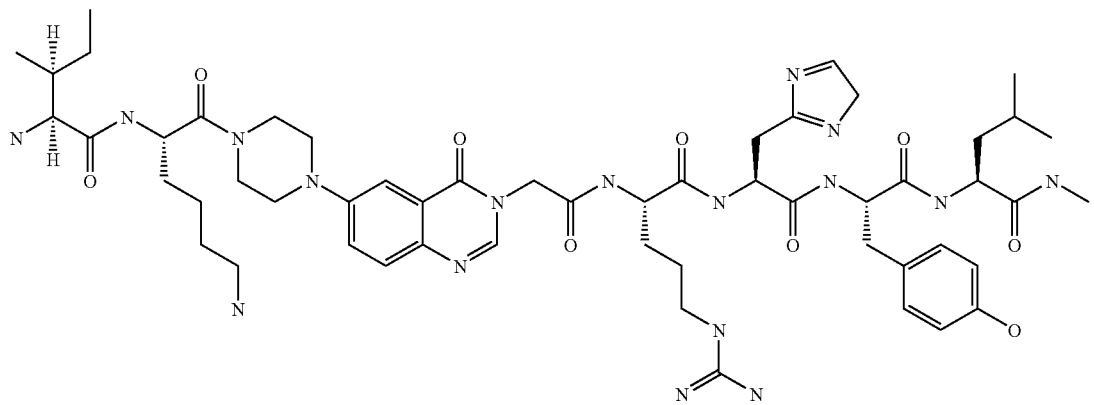

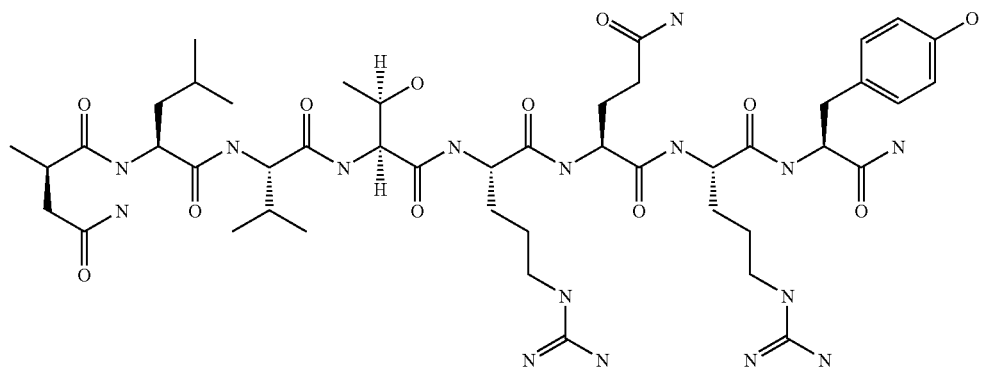
Fmoc-Linker-BHA resin (450 mg, 0.25 mmol) from Example 1 was subjected to solid phase synthesis ((D) Asn was inserted in position 29 of the sequence) and purification by following the procedure in Example 3 to yield 50 mg (10%) of white amorphous powder. (ES)+-LCMS m/e calcd for $C_{98}H_{153}N_{33}O_{21}$ 2129.53 found 2128.80.
Example 25
Preparation of H-Ile-Lys-Pqa-Arg-His-Tyr-(D)Leu-Asn-Leu-Val-Thr-Arg-Gln-Arg-Tyr-NH$_2$
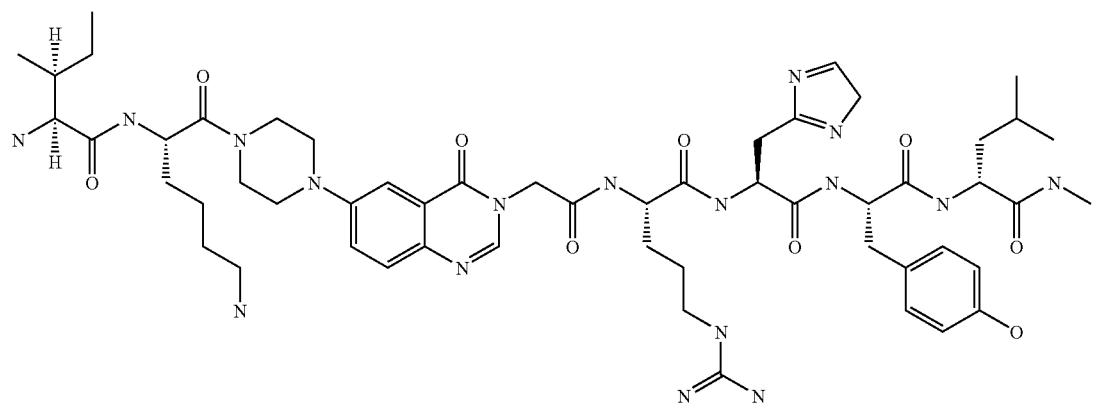
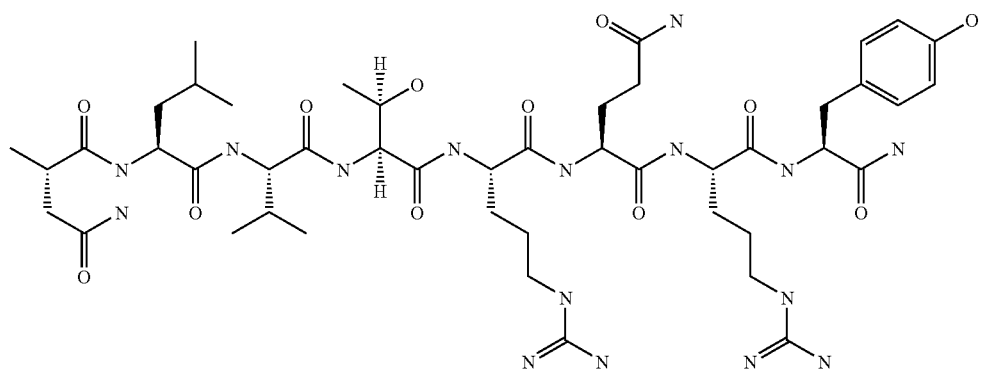

Fmoc-Linker-BHA resin (450 mg, 0.25 mmol) from Example 1 was subjected to solid phase synthesis ((D) Leu was inserted in position 28 of the sequence) and purification by following the procedure in Example 3 to yield 188 mg (35%) of white amorphous powder. (ES)+-LCMS m/e calcd for $C_{98}H_{153}N_{33}O_{21}$ 2129.53 found 2129.40.

Example 26

Preparation of H-Ile-Lys-Pqa-Arg-His-(D)Tyr-Leu-Asn-Leu-Val-Thr-Arg-Gln-Arg-Tyr-$NH_2$

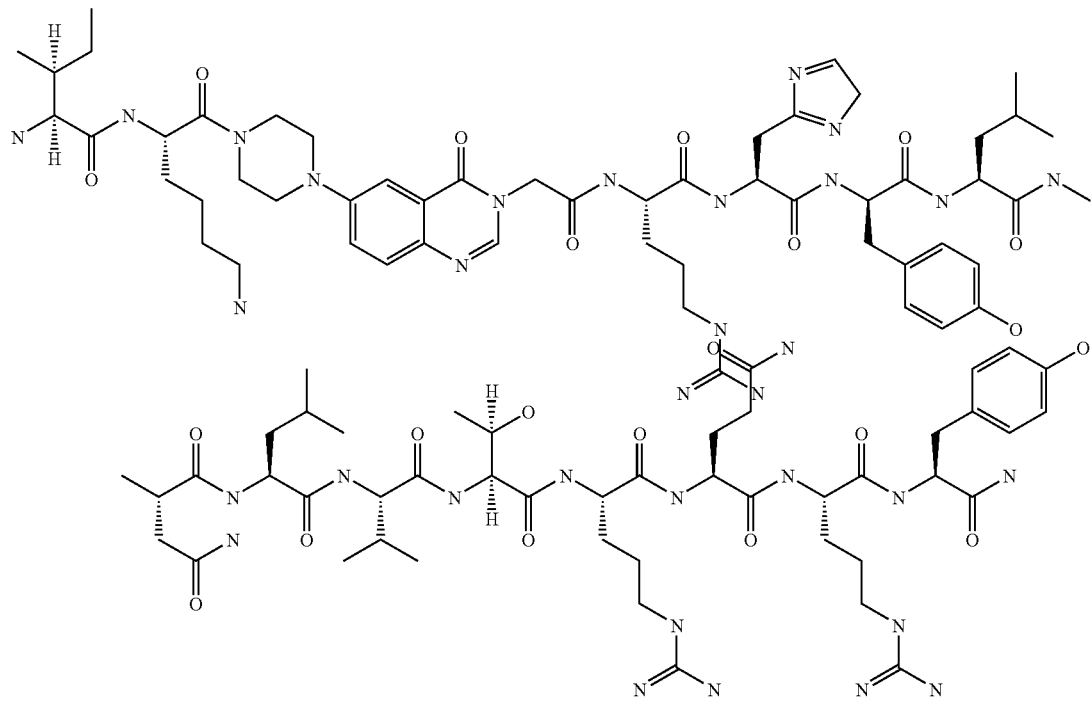

Fmoc-Linker-BHA resin (450 mg, 0.25 mmol) from Example 1 was subjected to solid phase synthesis ((D) Tyr was inserted in position 27 of the sequence) and purification by following the procedure in Example 3 to yield 119 mg (22%) of white amorphous powder. (ES)+-LCMS m/e calcd for $C_{98}H_{153}N_{33}O_{21}$ 2129.53 found 2129.70.

Example 27

Preparation of H-Ile-Lys-Pqa-Arg-(D)His-Tyr-Leu-Asn-Leu-Val-Thr-Arg-Gln-Arg-Tyr-$NH_2$

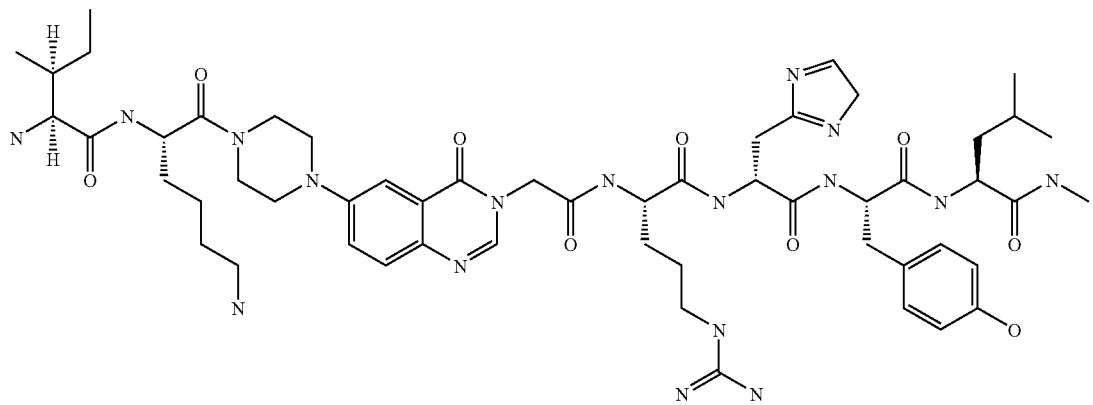

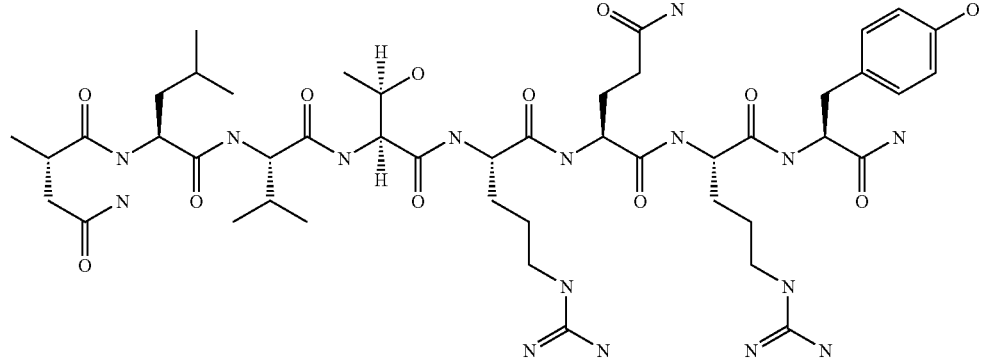

Fmoc-Linker-BHA resin (450 mg, 0.25 mmol) from Example 1 was subjected to solid phase synthesis ((D) His was inserted in position 26 of the sequence) and purification by following the procedure in Example 3 to yield 84 mg (16%) of white amorphous powder. (ES)+-LCMS m/e calcd for $C_{98}H_{153}N_{33}O_{21}$ 2129.53 found 2128.80.

Fmoc-Linker-BHA resin (450 mg, 0.25 mmol) from Example 1 was subjected to solid phase synthesis ((D) Arg was inserted in position 25 of the sequence) and purification by following the procedure in Example 3 to yield 85 mg (16%) of white amorphous powder. (ES)+-LCMS m/e calcd for $C_{98}H_{153}N_{33}O_{21}$ 2129.53 found 2128.80.

Example 28

Preparation of H-Ile-Lys-Pqa-(D)Arg-His-Tyr-Leu-Asn-Leu-Val-Thr-Arg-Gln-Arg-Tyr-NH$_2$

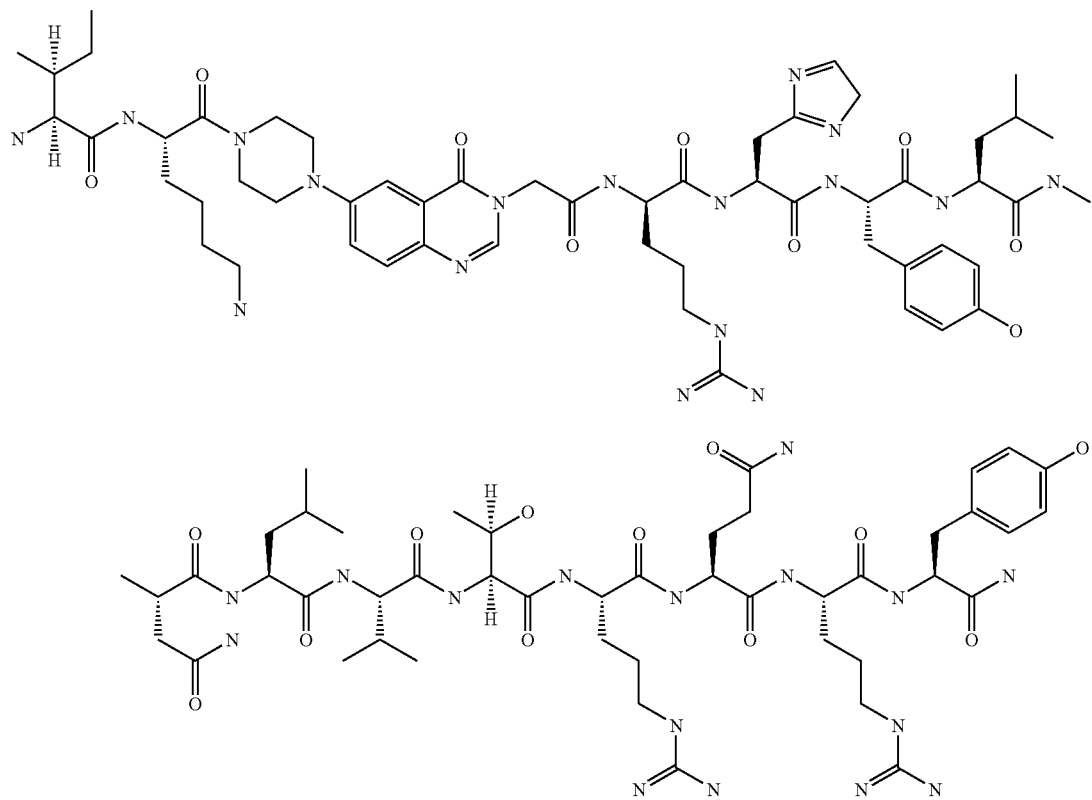

Example 29

Preparation of H-Ile-(D)Lys-Pqa-Arg-His-Tyr-Leu-Asn-Leu-Val-Thr-Arg-Gln-Arg-Tyr-NH$_2$ (SEQ ID NO: 5)

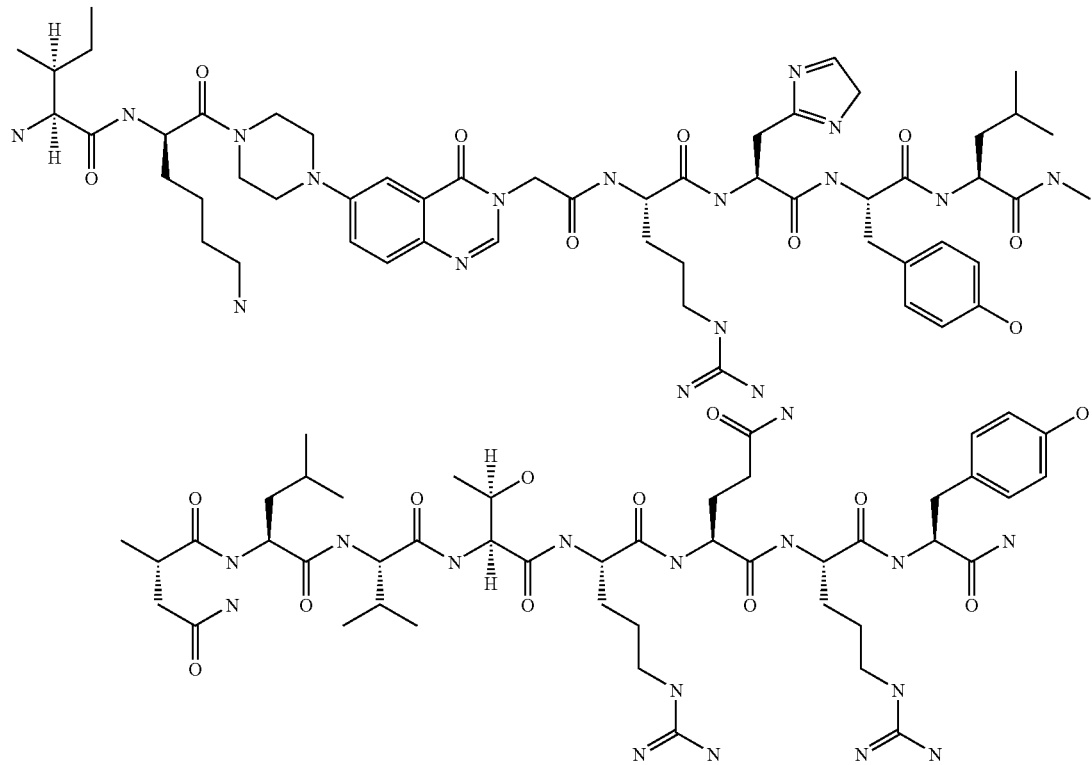

Fmoc-Linker-BHA resin (450 mg, 0.25 mmol) from Example 1 was subjected to solid phase synthesis ((D) Lys was inserted in position 4 of the sequence) and purification by following the procedure in Example 3 to yield 165 mg (31%) of white amorphous powder. (ES)+-LCMS m/e calcd for C$_{98}$H$_{153}$N$_{33}$O$_{21}$ 2129.53 found 2129.10.

Example 30

Preparation of H-(D) Ile-Lys-Pqa-Arg-His-Tyr-Leu-Asn-Leu-Val-Thr-Arg-Gln-Arg-Tyr-NH$_2$ (SEQ ID NO: 5)

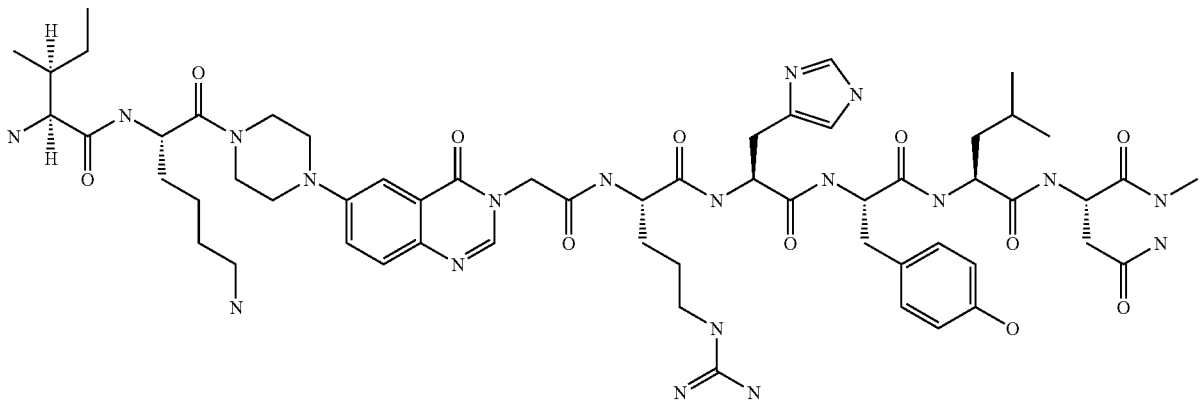

-continued

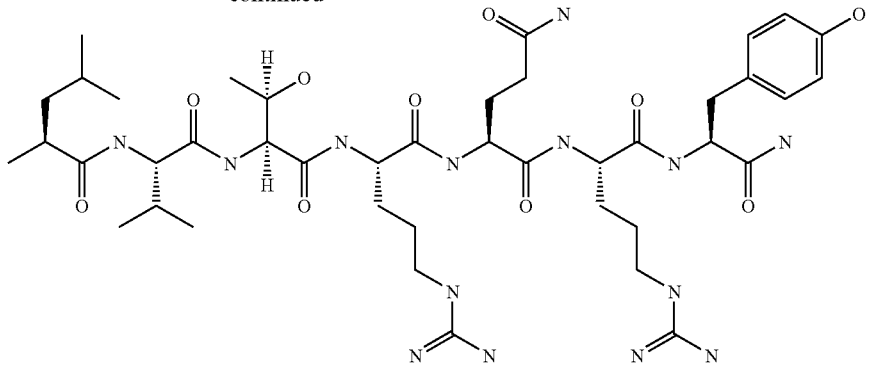

Fmoc-Linker-BHA resin (450 mg, 0.25 mmol) from Example 1 was subjected to solid phase synthesis ((D) Ile was inserted in position 3 of the sequence) and purification by following the procedure in Example 3 to yield 84 mg (8%) of white amorphous powder. (ES)+-LCMS m/e calcd for $C_{98}H_{153}N_{33}O_{21}$ 2129.53 found 2129.40.

Example 31

Preparation of H-Ile-Lys-Pqa-Arg-His-Tyr-Leu-Asn-Leu-Val-Thr-Arg-Gln-Arg-(NMe)Tyr-NH$_2$ (SEQ ID NO: 15)

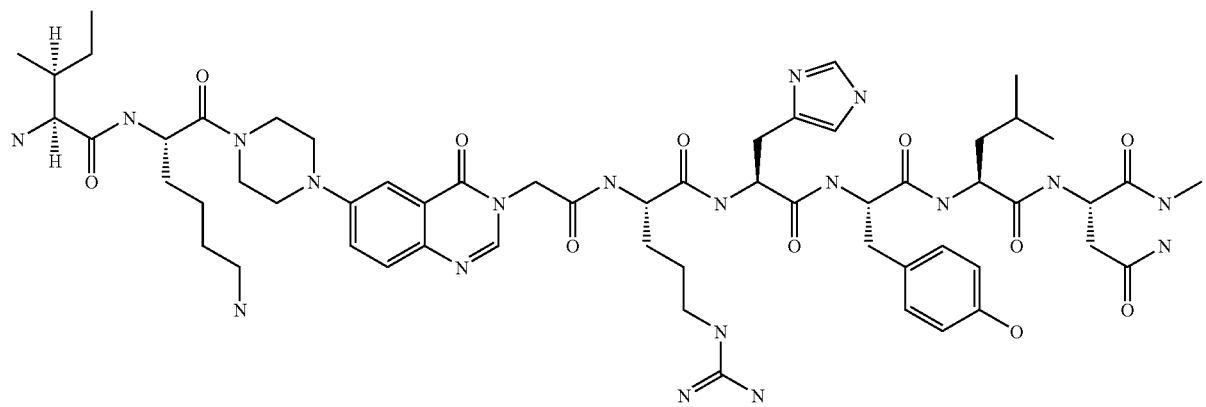

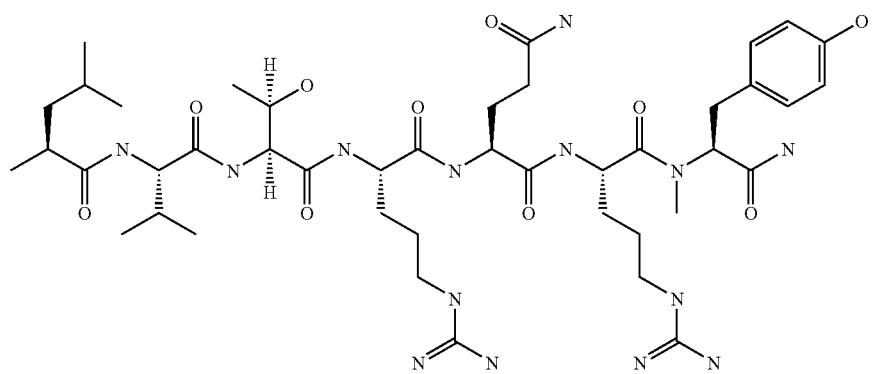

Fmoc-Linker-BHA resin (450 mg, 0.25 mmol) from Example 1 was subjected to solid phase synthesis (N-methyl Tyr was inserted in position 36 of the sequence) and purification by following the procedure in Example 3 to yield 90 mg (17%) of white amorphous powder. (ES)+-LCMS m/e calcd for $C_{99}H_{157}N_{33}O_{21}$ 2143.56 found 2143.50.

Example 32

Preparation of H-Ile-Lys-Pqa-Arg-His-Tyr-Leu-Asn-Leu-Val-Thr-Arg-Gln-(NMe)Arg-Tyr-NH$_2$ (SEQ ID NO: 16)

Fmoc-Linker-BHA resin (450 mg, 0.25 mmol) from Example 1 was subjected to solid phase synthesis (N-methyl Arg was inserted in position 35 of the sequence) and purification by following the procedure in Example 3 to yield 32 mg (6%) of white amorphous powder. (ES)+-LCMS m/e calcd for $C_{99}H_{155}N_{33}O_{21}$ 2143.56 found 2143.50.

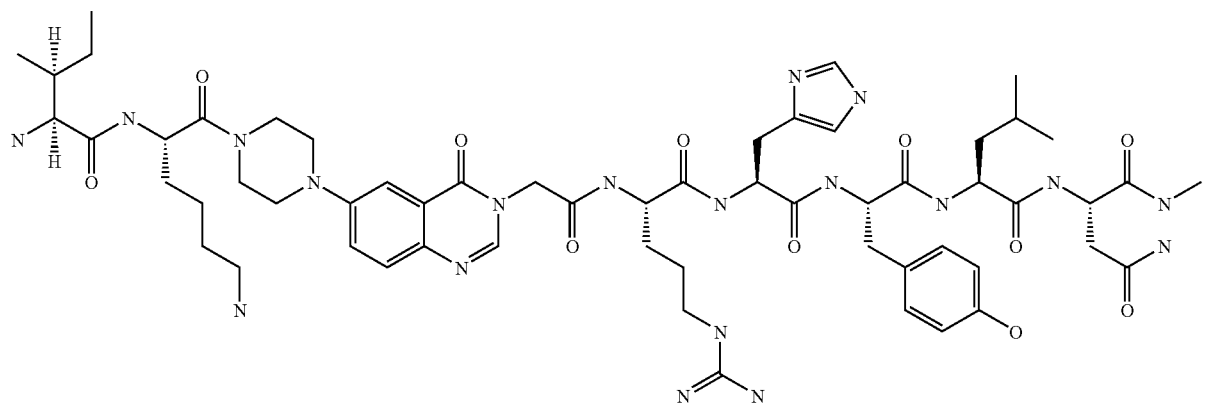

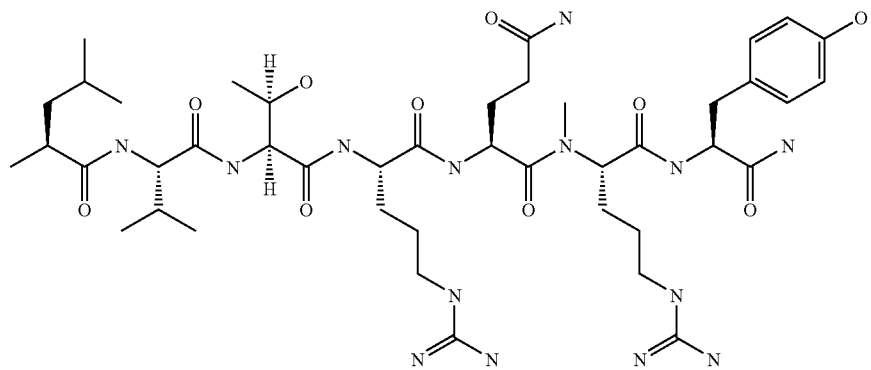

Example 33

Preparation of H-Ile-Lys-Pqa-Arg-His-Tyr-Leu-Asn-Leu-Val-Thr-(NMe)Arg-Gln-Arg-Tyr-NH$_2$ (SEQ ID NO: 17)

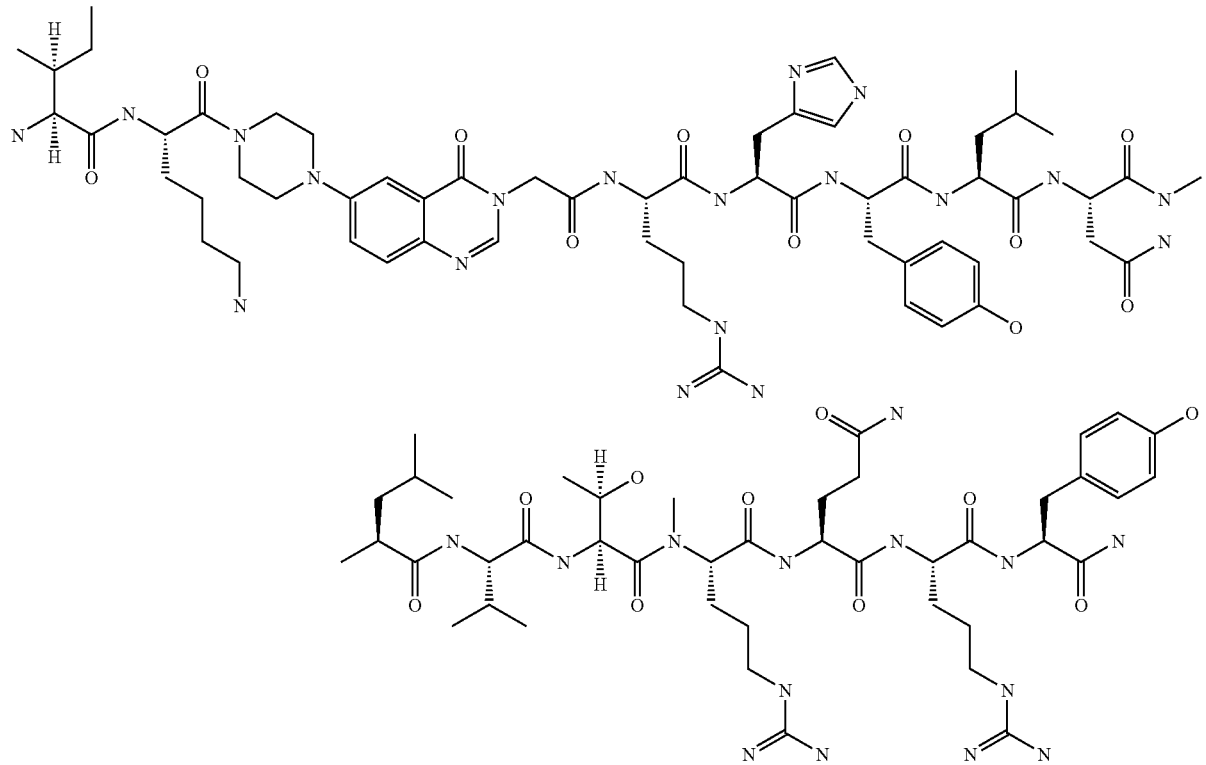

Fmoc-Linker-BHA resin (450 mg, 0.25 mmol) from Example 1 was subjected to solid phase synthesis (N-methyl Arg was inserted in position 33 of the sequence) and purification by following the procedure in Example 3 to yield 40 mg (7%) of white amorphous powder. (ES)+-LCMS m/e calcd for $C_{99}H_{155}N_{33}O_{21}$ 2143.56 found 2143.20.

Example 34

Preparation of H-Ile-Lys-Pqa-Arg-His-Tyr-Leu-Asn-Leu-Val-(NMe)Thr-Arg-Gln-Arg-Tyr-NH$_2$ (SEQ ID NO: 18)

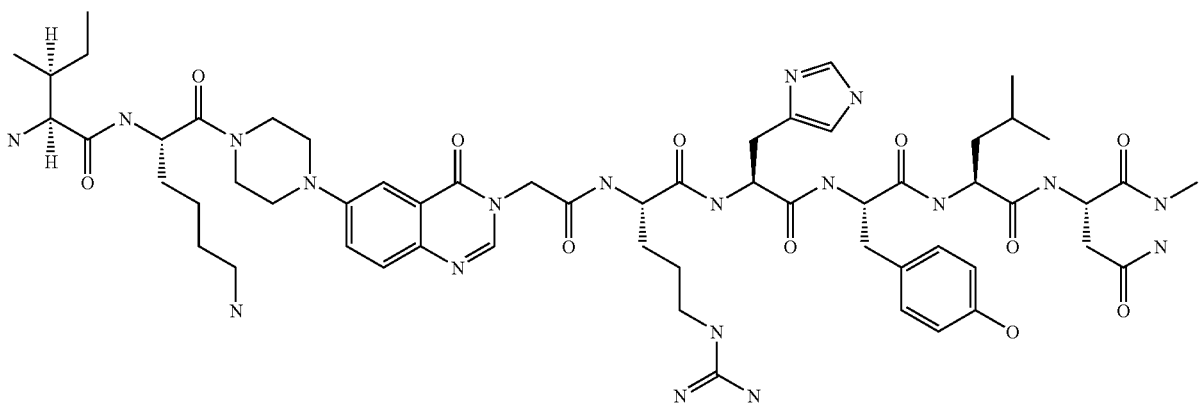

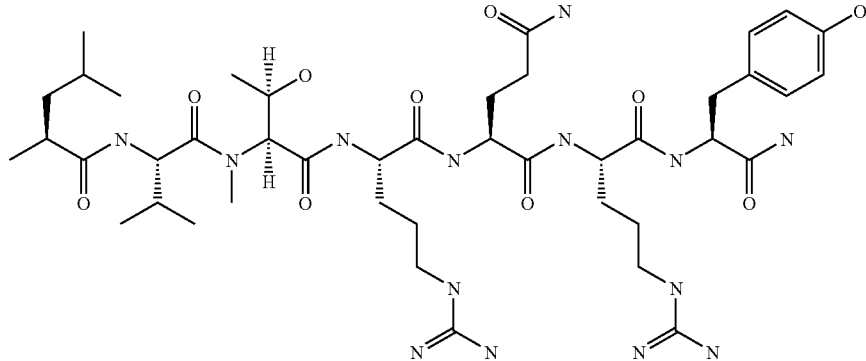

Fmoc-Linker-BHA resin (450 mg, 0.25 mmol) from Example 1 was subjected to solid phase synthesis (N-methyl Thr was inserted in position 32 of the sequence) and purification by following the procedure in Example 3 to yield 115 mg (21%) of white amorphous powder. (ES)+-LCMS m/e calcd for $C_{99}H_{155}N_{33}O_{21}$ 2143.56 found 2143.20.

Example 35

Preparation of H-Ile-Lys-Pqa-Arg-His-Tyr-Leu-Asn-Leu-(NMe)Val-Thr-Arg-Gln-Arg-Tyr-NH$_2$ (SEQ ID NO: 19)

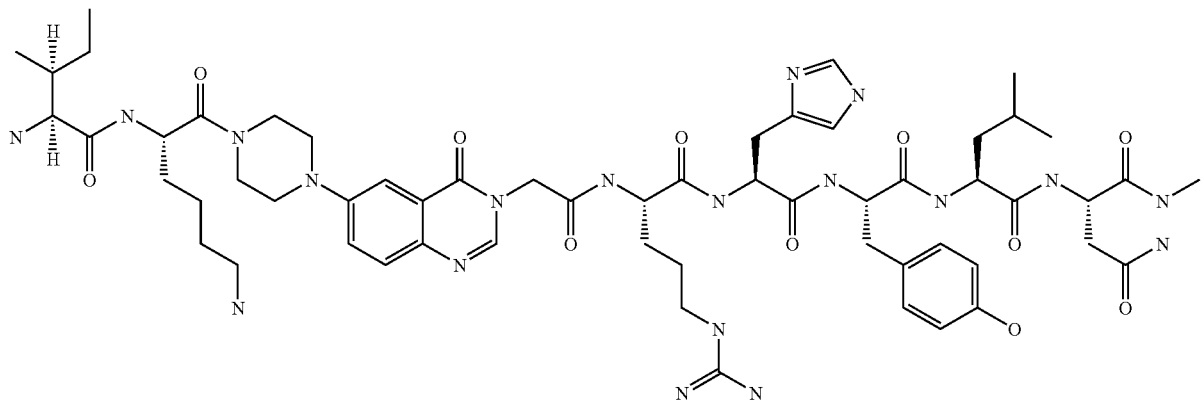

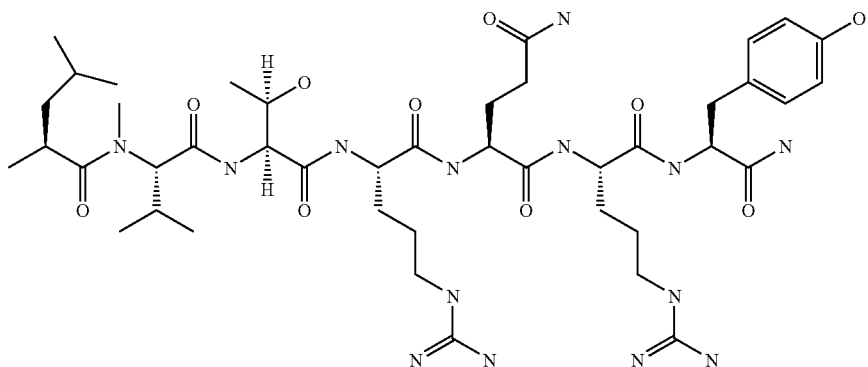

Fmoc-Linker-BHA resin (450 mg, 0.25 mmol) from Example 1 was subjected to solid phase synthesis (N-methyl Val was inserted in position 31 of the sequence) and purification by following the procedure in Example 3 to yield 60 mg (11%) of white amorphous powder. (ES)+-LCMS m/e calcd for $C_{99}H_{155}N_{33}O_{21}$ 2143.56 found 2143.20.

Example 36

Preparation of H-Ile-Lys-Pqa-Arg-His-Tyr-Leu-Asn-(NMe)Leu-Val-Thr-Arg-Gln-Arg-Tyr-NH$_2$ (SEQ ID NO: 20)

Fmoc-Linker-BHA resin (450 mg, 0.25 mmol) from Example 1 was subjected to solid phase synthesis (N-methyl leu was inserted in position 30 of the sequence) and purification by following the procedure in Example 3 to yield 91 mg (17%) of white amorphous powder. (ES)+-LCMS m/e calcd for C99H155N33O21 2143.56 found 2142.90.

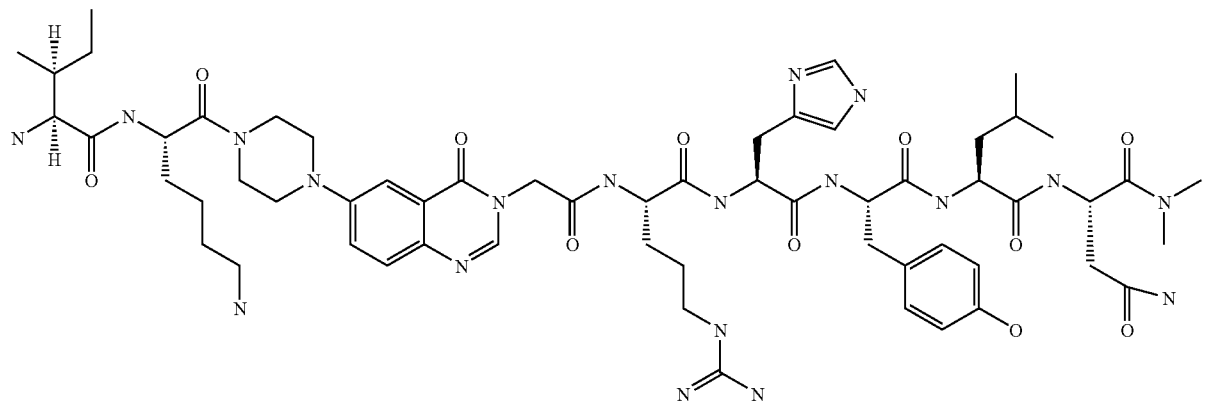

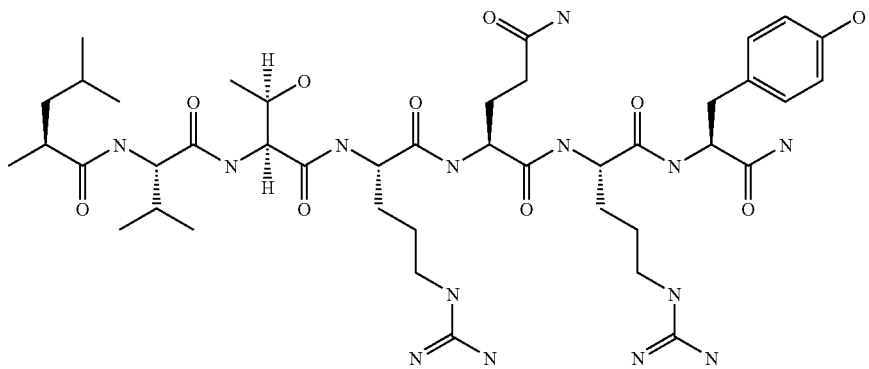

Example 37

Preparation of H-Ile-Lys-Pqa-Arg-His-Tyr-(NMe)Leu-Asn-Leu-Val-Thr-Arg-Gln-Arg-Tyr-NH$_2$ (SEQ ID NO: 21)

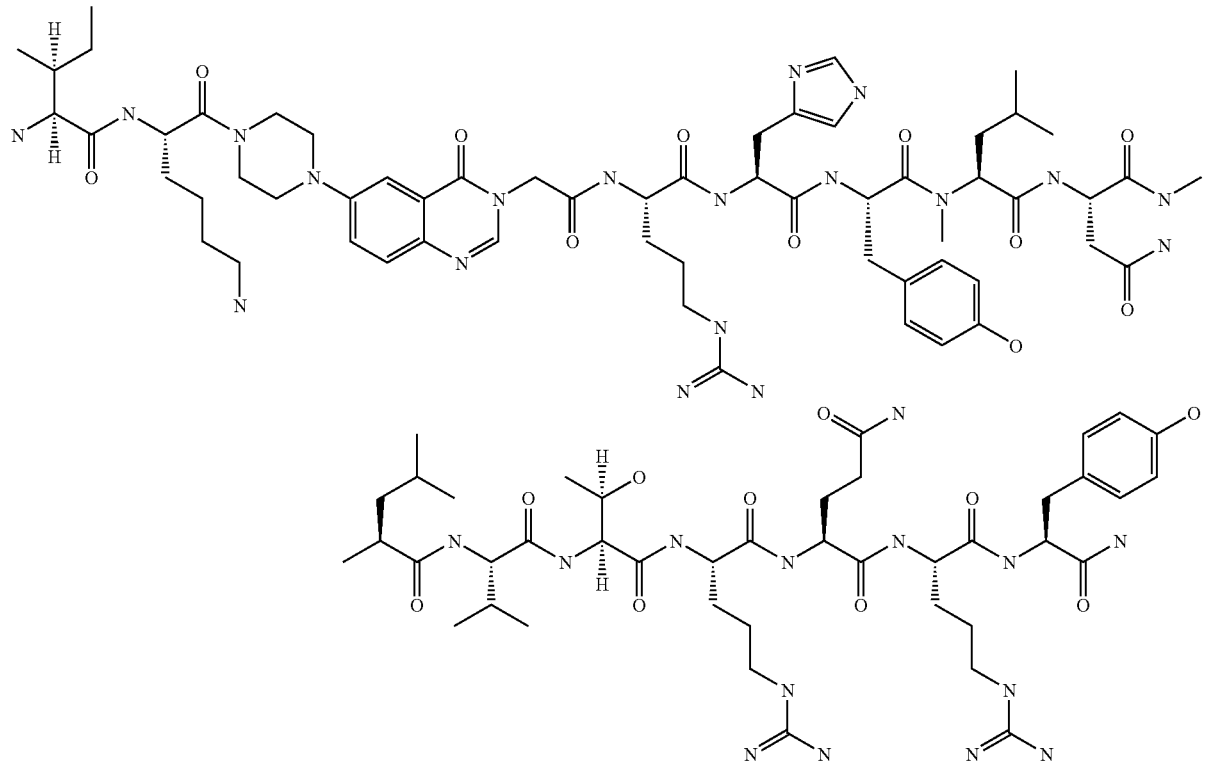

Fmoc-Linker-BHA resin (450 mg, 0.25 mmol) from Example 1 was subjected to solid phase synthesis (N-methyl leu was inserted into position 28 of the sequence) and purification by following the procedure in Example 3 to yield 153 mg (28%) of white amorphous powder. (ES)+-LCMS m/e calcd for C$_{99}$H$_{155}$N$_{33}$O$_{21}$ 2143.56 found 2142.90.

Example 38

Preparation of H-Ile-Lys-Pqa-Arg-His-(NMe)Tyr-Leu-Asn-Leu-Val-Thr-Arg-Gln-Arg-Tyr-NH$_2$ (SEQ ID NO: 22)

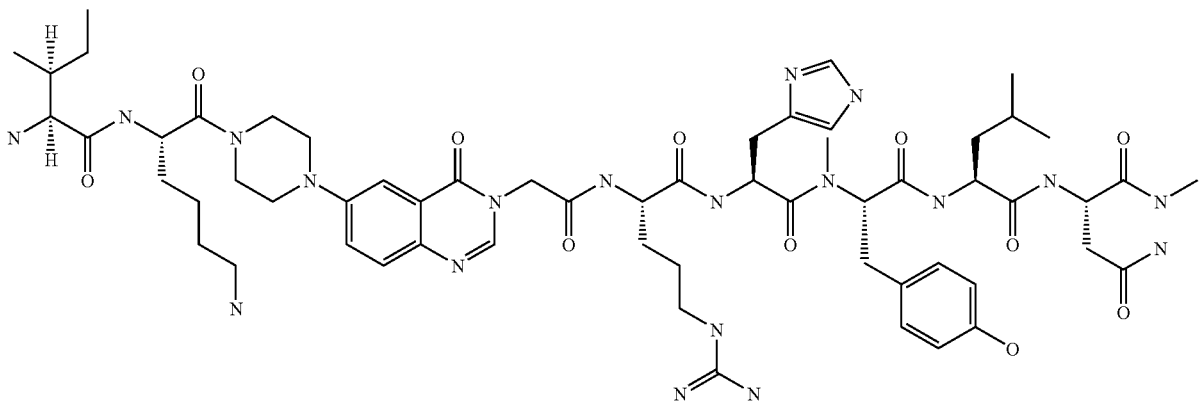

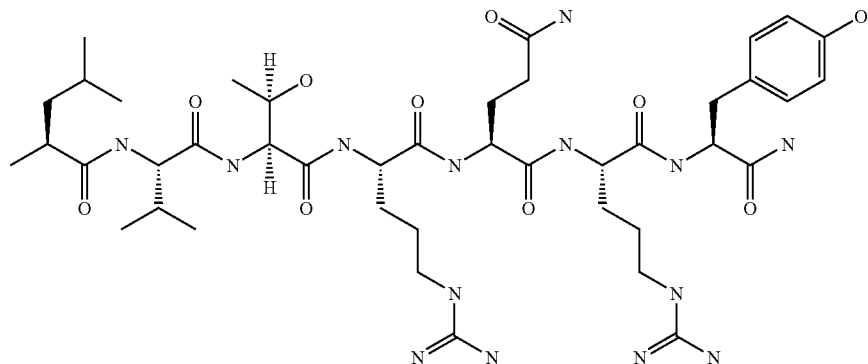

Fmoc-Linker-BHA resin (450 mg, 0.25 mmol) from Example 1 was subjected to solid phase synthesis (N-methyl Tyr was inserted in position 27 of the sequence) and purification by following the procedure in Example 3 to yield 76 mg (14%) of white amorphous powder. (ES)+-LCMS m/e calcd for $C_{99}H_{155}N_{33}O_{21}$ 2143.56 found 2142.90.

Example 39

Preparation of H-Ile-Lys-Pqa-Arg-(NMe)His-Tyr-Leu-Asn-Leu-Val-Thr-Arg-Gln-Arg-Tyr-NH$_2$ (SEQ ID NO: 23)

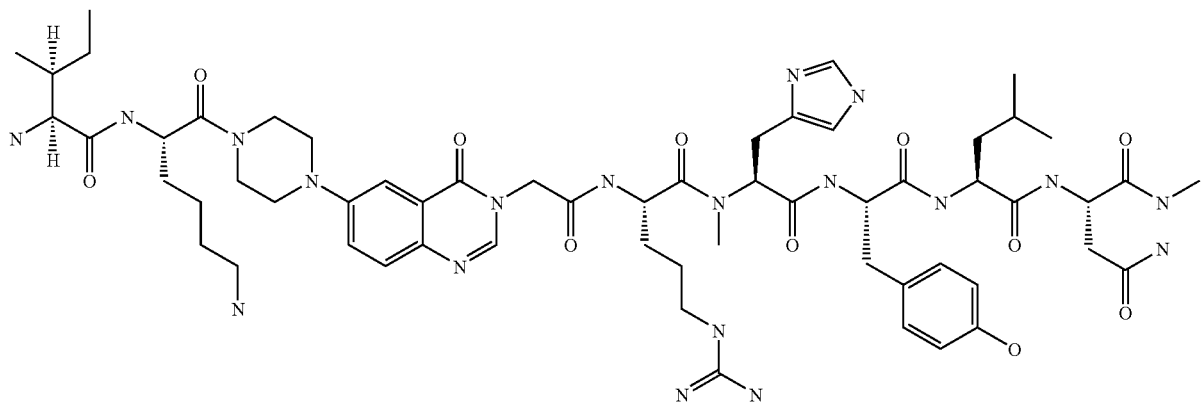

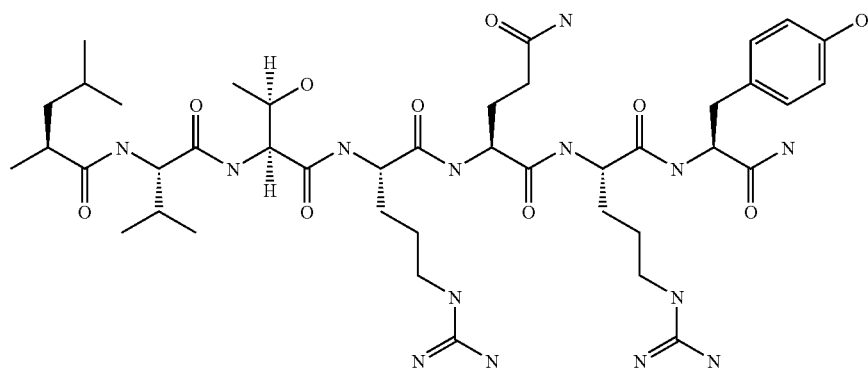

Fmoc-Linker-BHA resin (450 mg, 0.25 mmol) from Example 1 was subjected to solid phase synthesis (N-methyl His was inserted in position 26 of the sequence) and purification by following the procedure in Example 3 to yield 93 mg (7%) of white amorphous powder. (ES)+-LCMS m/e calcd for $C_{99}H_{155}N_{33}O_{21}$ 2143.53 found 2143.50.

Example 40

Preparation of H-Ile-Lys-Pqa-(NMe)Arg-His-Tyr-Leu-Asn-Leu-Val-Thr-Arg-Gln-Arg-Tyr-NH$_2$ (SEQ ID NO: 24)

Fmoc-Linker-BHA resin (450 mg, 0.25 mmol) from Example 1 was subjected to solid phase synthesis (N-methyl Arg was inserted in position 25 of the sequence) and purification by following the procedure in Example 3 to yield 33 mg (6%) of white amorphous powder. (ES)+-LCMS m/e calcd for $C_{99}H_{155}N_{33}O_{21}$ 2143.56 found 2143.50.

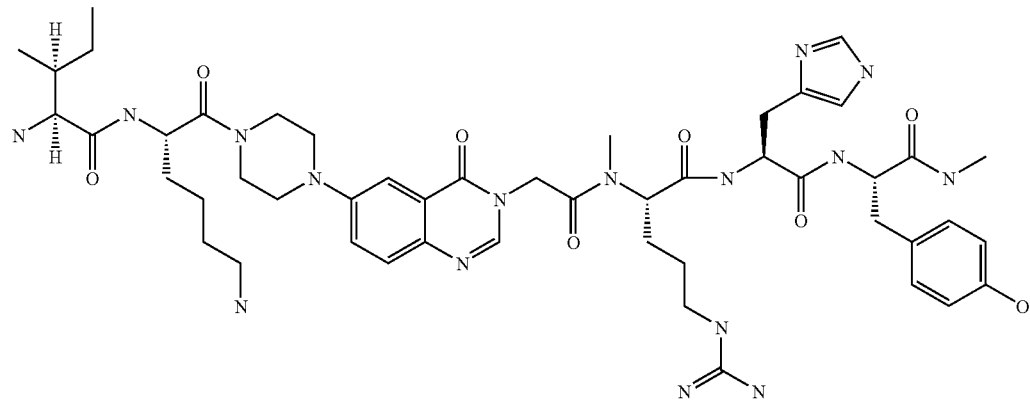

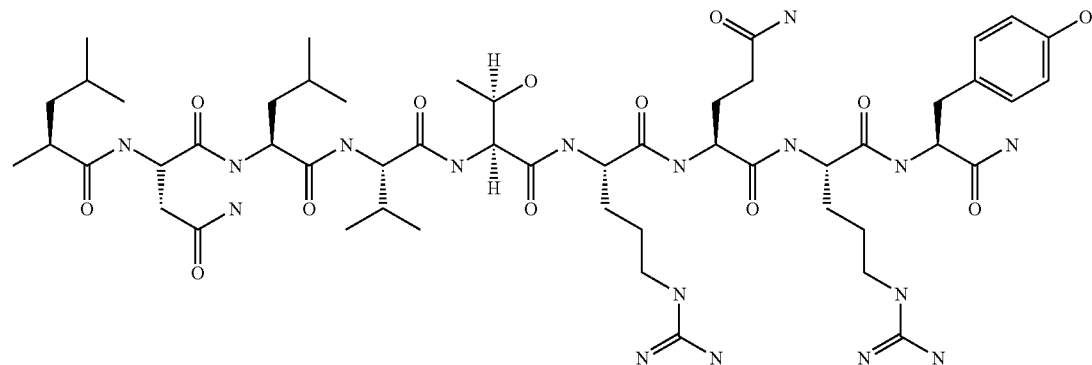

Example 41

Preparation of H-Ile-NMeLys-Pqa-Arg-His-Tyr-Leu-Asn-Leu-Val-Thr-Arg-Gln-Arg-Tyr-NH$_2$ (SEQ ID NO: 5)

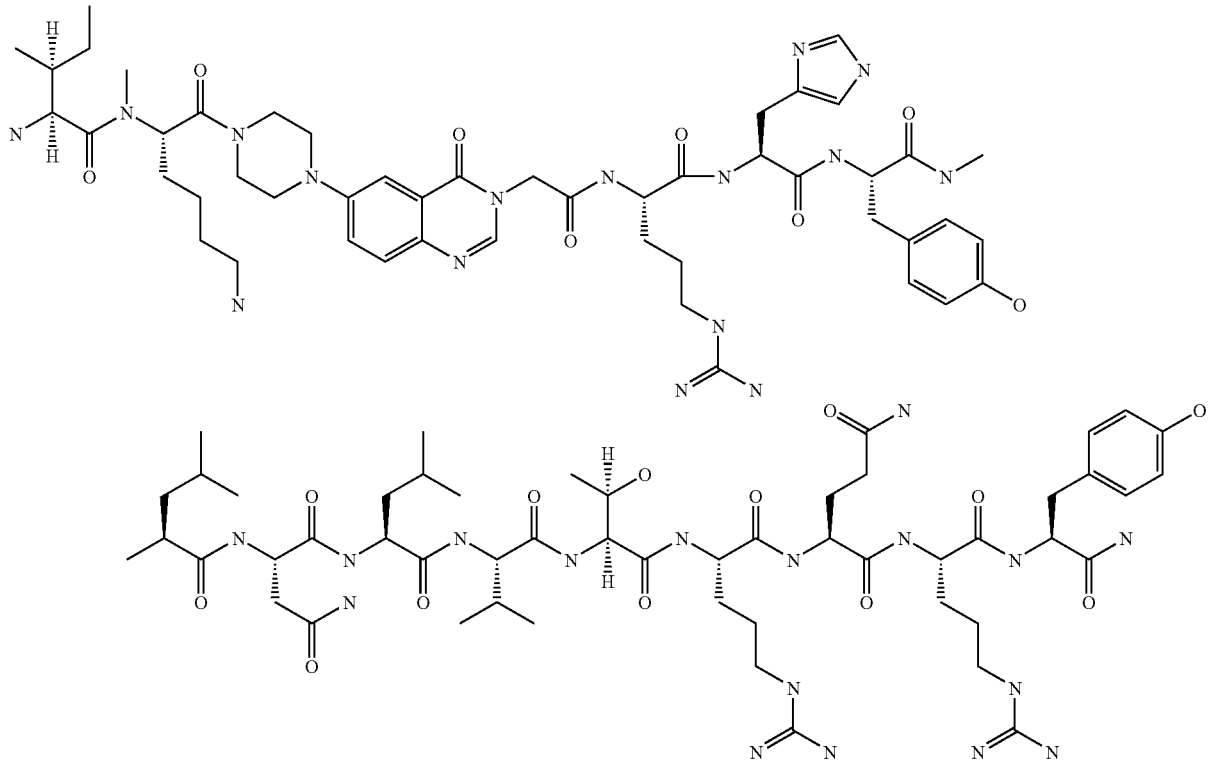

Fmoc-Linker-BHA resin (450 mg, 0.25 mmol) from Example 1 was subjected to solid phase synthesis (N-methyl Lys was inserted in position 4 of the sequence) and purification by following the procedure in Example 3 to yield 156 mg (29%) of white amorphous powder. (ES)+-LCMS m/e calcd for $C_{99}H_{155}N_{33}O_{21}$ 2143.56 found 2143.20.

Example 42

Preparation of H-NMeIle-Lys-Pqa-Arg-His-Tyr-Leu-Asn-Leu-Val-Thr-Arg-Gln-Arg-Tyr-NH$_2$ (SEQ ID NO: 5)

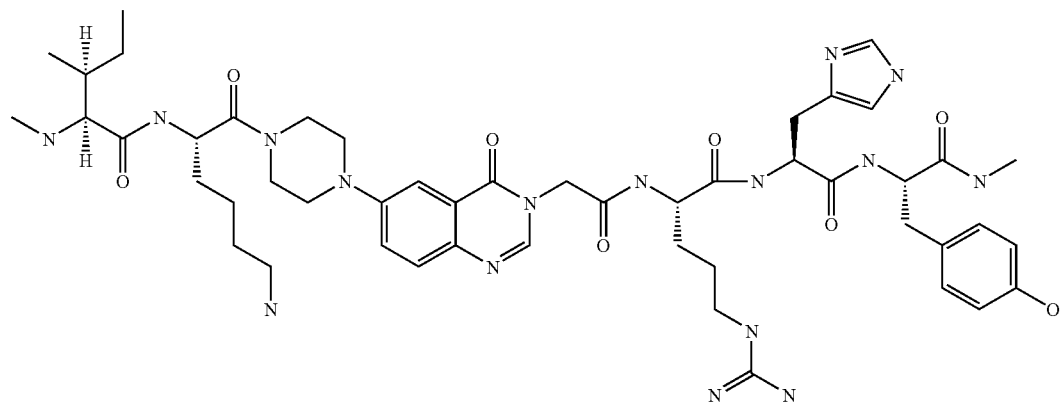

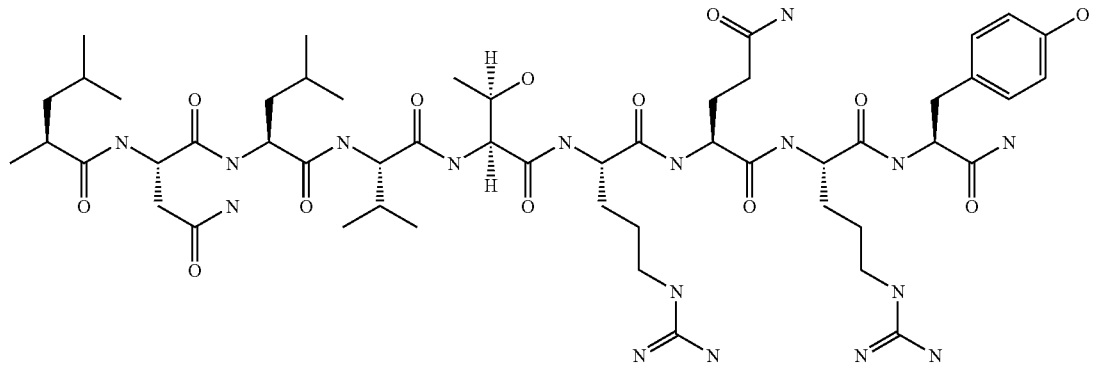
Fmoc-Linker-BHA resin (450 mg, 0.25 mmol) from Example 1 was subjected to solid phase synthesis (N-methyl Ile was inserted in position 3 of the sequence) and purification by following the procedure in Example 3 to yield 203 mg (38%) of white amorphous powder. (ES)+-LCMS m/e calcd for $C_{99}H_{155}N_{33}O_{21}$ 2143.56 found 2143.20.
Example 43
Preparation of H-Ile-Nle-Pqa-Arg-His-Tyr-Leu-Asn-Leu-Val-Thr-Arg-Gln-Arg-Tyr-NH$_2$ (SEQ ID NO: 5)
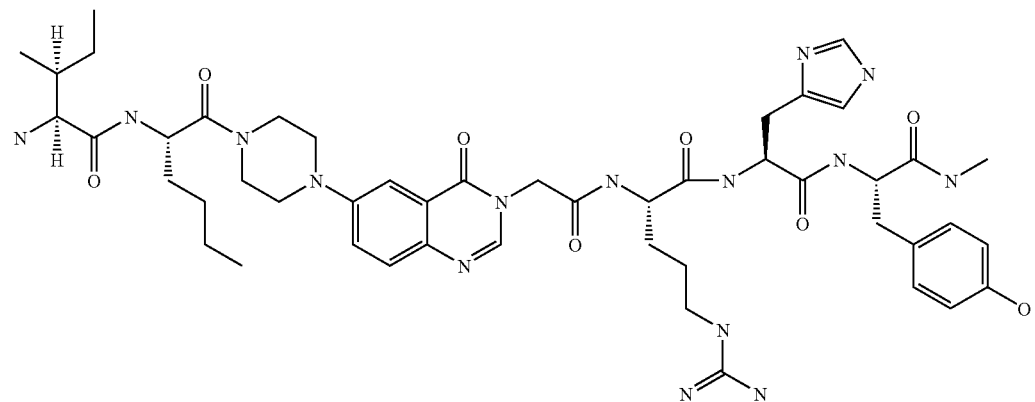
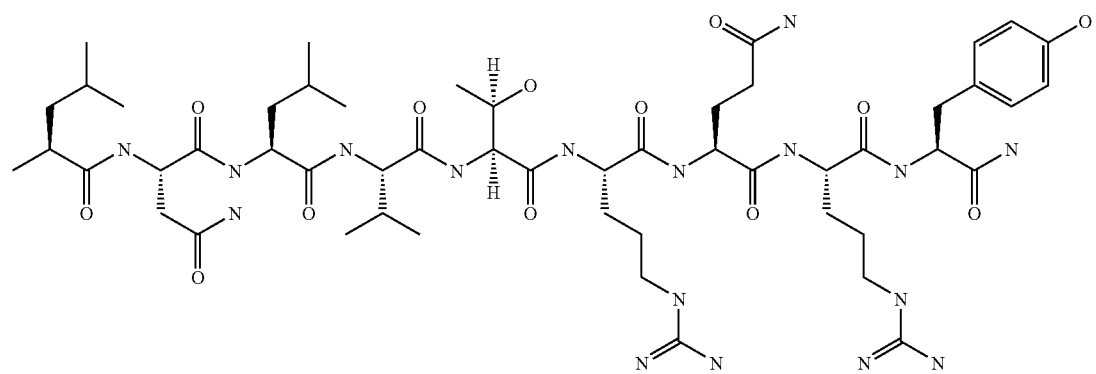

Fmoc-Linker-BHA resin (450 mg, 0.25 mmol) from Example 1 was subjected to solid phase synthesis (Nle was inserted in position 4 of the sequence) and purification by following the procedure in Example 3 to yield 60 mg (11%) of white amorphous powder. (ES)+-LCMS m/e calcd for $C_{98}H_{153}N_{32}O_{21}$ 2114.52 found 2113.80.
Example 44
Preparation of Ac-Ile-Nle-Pqa-Arg-His-Tyr-Leu-Asn-Leu-Val-Thr-Arg-Gln-Arg-Tyr-NH$_2$ (SEQ ID NO: 5)
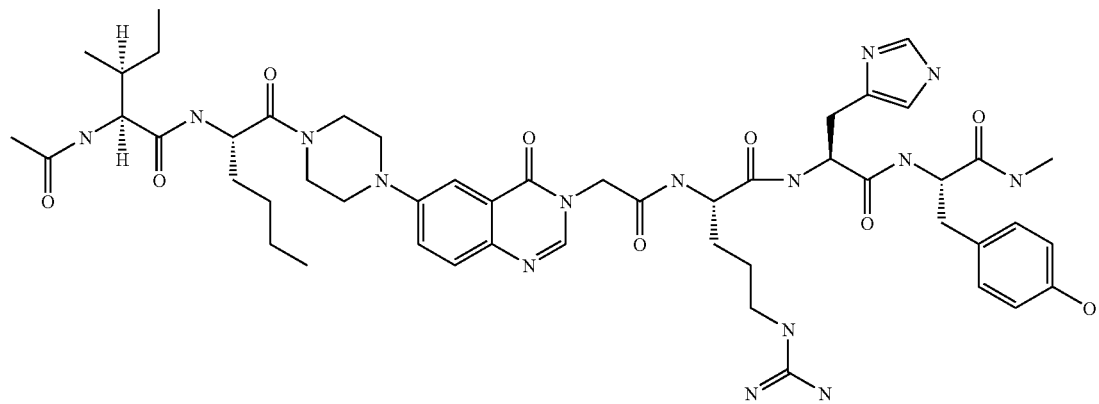
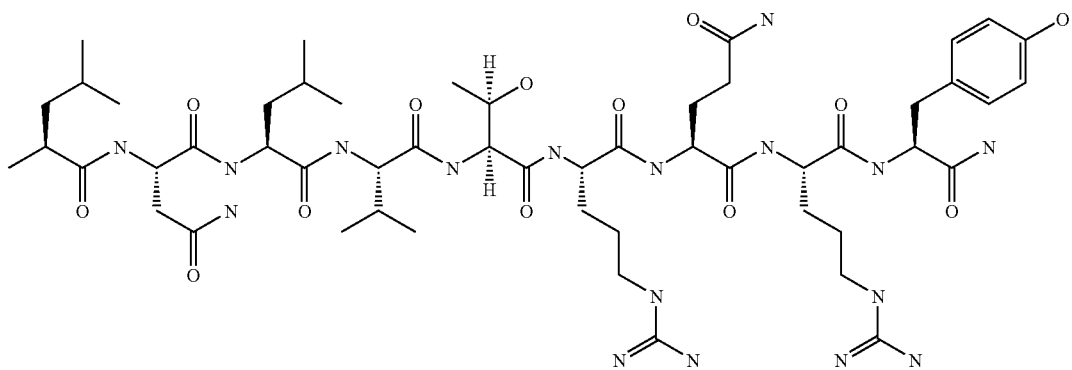

Fmoc-Linker-BHA resin (450 mg, 0.25 mmol) from Example 1 was subjected to solid phase synthesis (actylation cycle was added to the protocol) and purification by following the procedure in Example 3 to yield 41 mg (8%) of white amorphous powder. (ES)+-LCMS m/e calcd for $C_{100}H_{154}N_{32}O_{22}$ 2156.56 found 2156.10.

Example 45

Preparation of Ac-Ile-Nle-Pqa-Phe-His-Tyr-Leu-Asn-Leu-Val-Thr-Arg-Gln-Arg-Tyr-NH$_2$ (SEQ ID NO: 25)

Fmoc-Linker-BHA resin (450 mg, 0.25 mmol) from Example 1 was subjected to solid phase synthesis (Phe was inserted in position 25 of the sequence) and purification by following the procedure in Example 3 to yield 92 mg (7%) of white amorphous powder. (ES)+-LCMS m/e calcd for $C_{103}H_{151}N_{29}O_{22}$ 2147.53 found 2148.00.

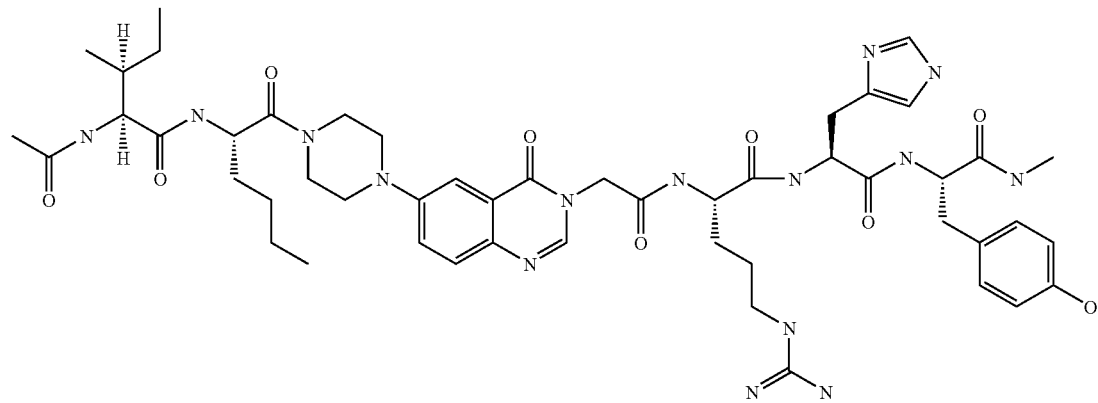

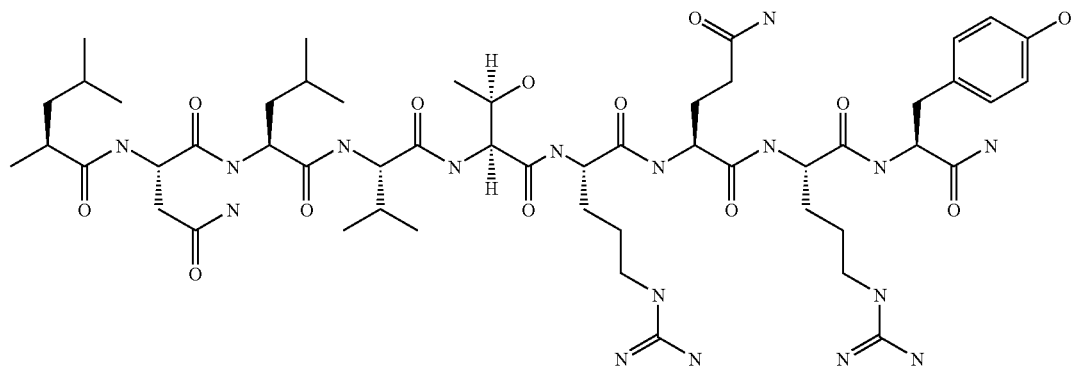

Example 46

Preparation of H-Ile-Lys-Pqa-Arg-His-Trp-Leu-Asn-Leu-Val-Thr-Arg-Gln-Arg-Tyr-NH$_2$ (SEQ ID NO: 26)

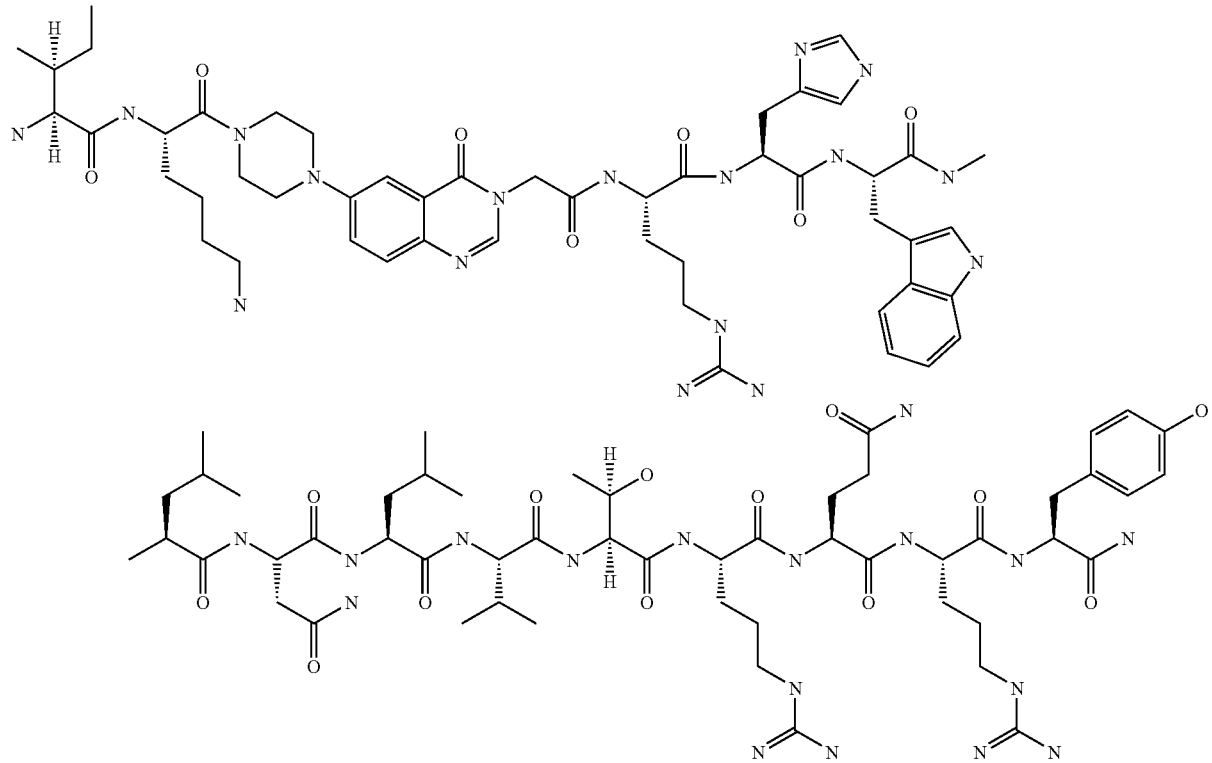

Fmoc-Linker-BHA resin (450 mg, 0.25 mmol) from Example 1 was subjected to solid phase synthesis (Trp was inserted in position 27 of the sequence) and purification by following the procedure in Example 3 to yield 30 mg (6%) of white amorphous powder. (ES)+-LCMS m/e calcd for C$_{100}$H$_{154}$N$_{34}$O$_{20}$ 2153.56 found 2152.20

Example 47

Preparation of H-Ile-Lys-Pqa-Ala-His-Trp-Leu-Asn-Leu-Val-Thr-Arg-Gln-Arg-Tyr-NH$_2$ (SEQ ID NO: 27)

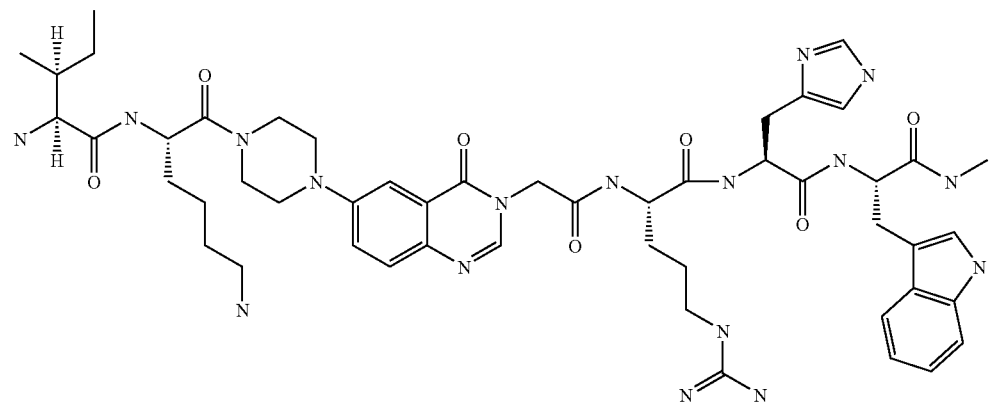

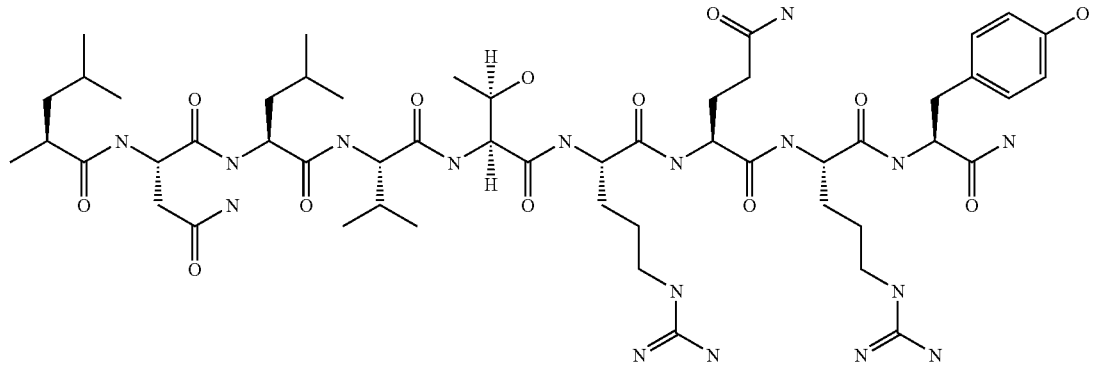

Fmoc-Linker-BHA resin (450 mg, 0.25 mmol) from Example 1 was subjected to solid phase synthesis (Ala 25 and Trp 27 were inserted in the sequence) and purification by following the procedure in Example 3 to yield 50 mg (9%) of white amorphous powder. (ES)+-LCMS m/e calcd for $C_{97}H_{147}N_{31}O_{20}$ 2067.46 found 2067.30.

Fmoc-Linker-BHA resin (450 mg, 0.25 mmol) from Example 1 was subjected to solid phase synthesis ((D)Tyr was inserted in position 36 of the sequence) and purification by following the procedure in Example 3 to yield 104 mg (19%) of white amorphous powder. (ES)+-LCMS m/e calcd for $C_{100}H_{154}N_{32}O_{22}$ 2156.54 found 2157.00.

Example 48

Preparation of Ac-Ile-Nle-Pqa-Arg-His-Tyr-Leu-Asn-Leu-Val-Thr-Arg-Gln-Arg-(D)Tyr-NH$_2$

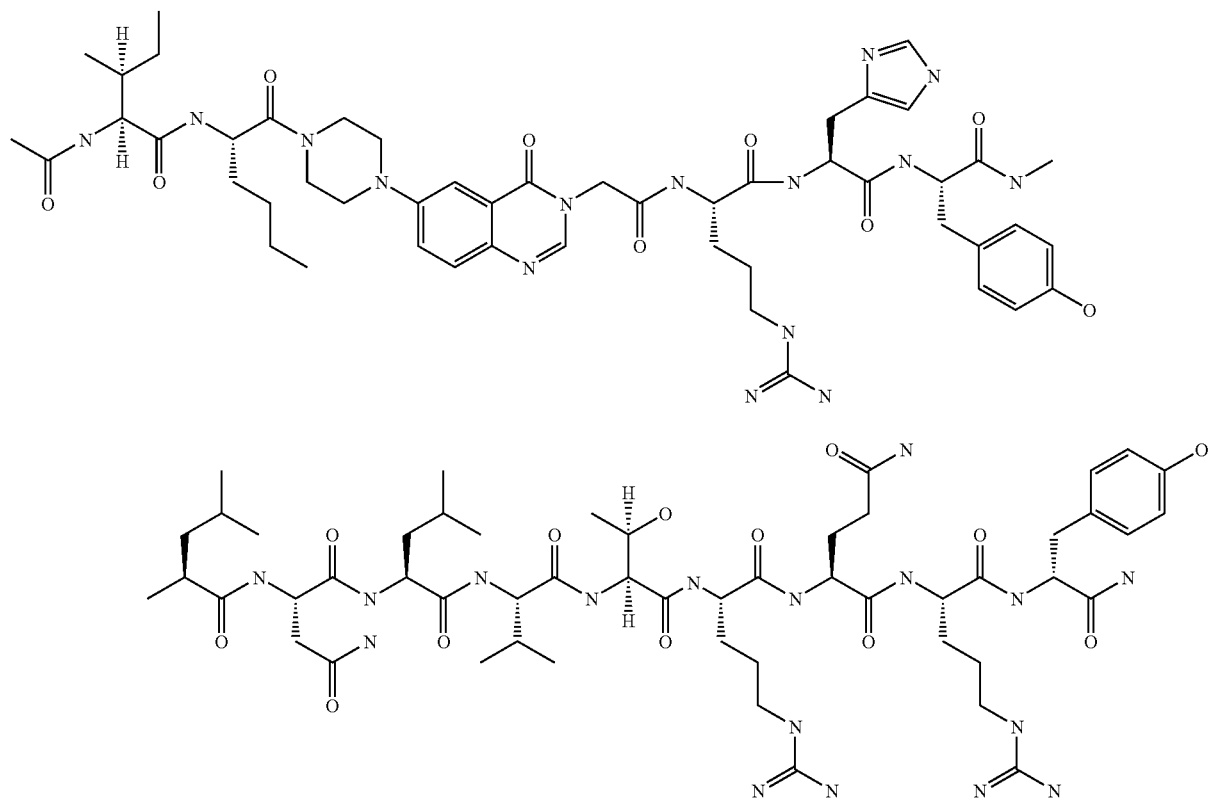

Example 49

Preparation of Ac-Ile-Nle-Pqa-Arg-His-Tyr-Leu-Asn-Leu-Val-Thr-Arg-Gln-Arg-N-methylTyr-NH$_2$ (SEQ ID NO: 15)

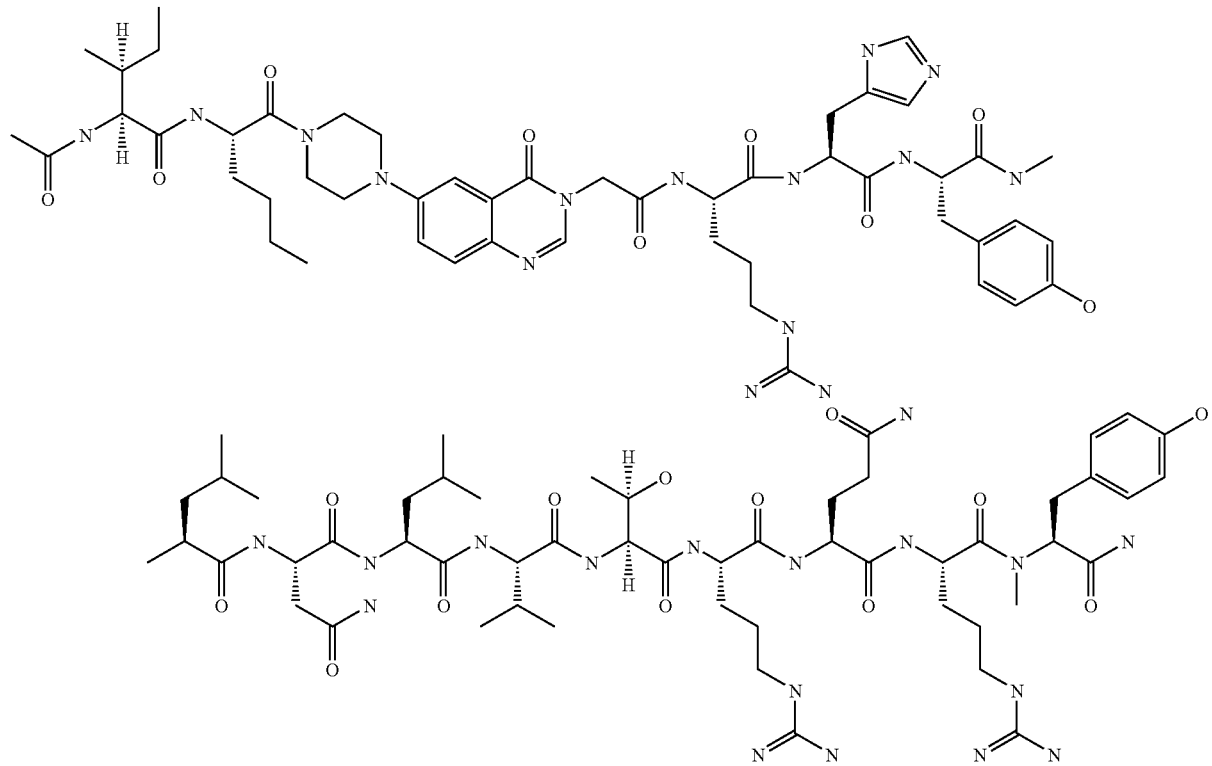

Fmoc-Linker-BHA resin (450 mg, 0.25 mmol) from Example 1 was subjected to solid phase synthesis (N-methyl Tyr was inserted in position 36 of the sequence) and purification by following the procedure in Example 3 to yield 28 mg (5%) of white amorphous powder. (ES)+-LCMS m/e calcd for C$_{101}$H$_{156}$N$_{32}$O$_{22}$ 2170.57 found 2170.50.

Example 50

Preparation of Cyclo Lys28-Asp32 Ac-Ile-Nle-Pqa-Arg-His-Tyr-Lys-Asn-Leu-Val-Asp-Arg-Gln-Arg-Tyr-NH$_2$ (SEQ ID NO: 28)

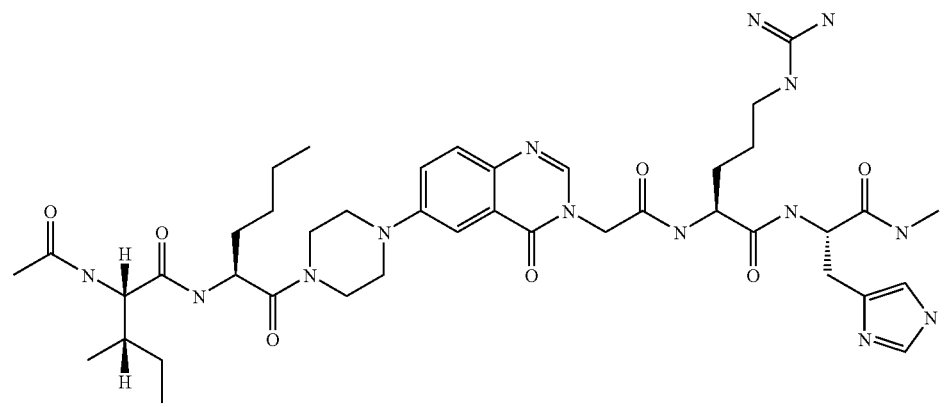

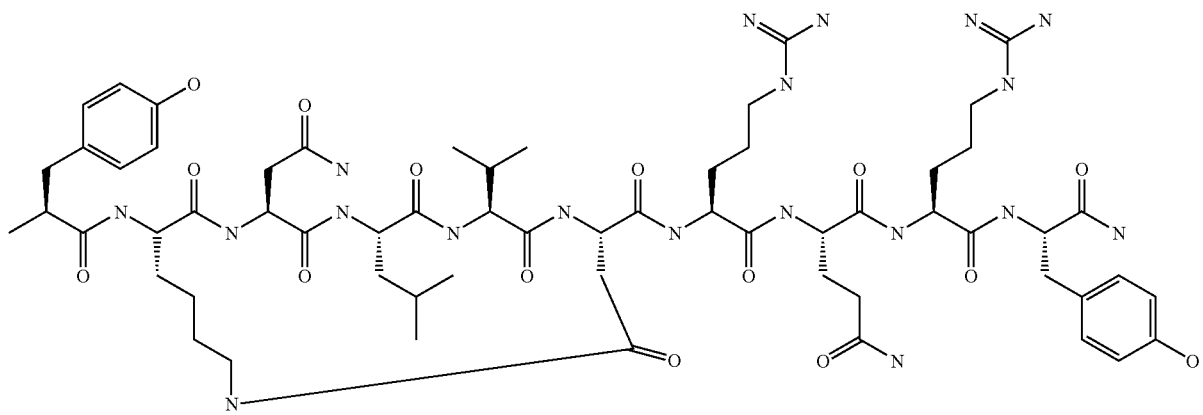

The peptide was prepared through a combination of automated synthesis on an ABI 433 synthesizer using a standard protocol and manual synthesis on a 0.25 mM scale. Fragment Fmoc-Asn(Trt)-Leu-Val-Asp(2Pip)-Arg(Pmc)-Gln(Trt)-Arg(Pmc)-Tyr(OBut)-BHA Resin (SEQ ID NO: 29) was synthesized using the ABI protocol and then extended manually to obtain Fmoc-Ile-Nle-Pqa-Arg(Pmc)-His(Trt)-Tyr(OBut)-Lys-Asn(Trt)-Leu-Val-Asp-Arg(Pmc)-Gln(Trt)-rg(Pmc)-Tyr(OBut)-BHA Resin(SEQ ID NO: 30). After completion of the automated synthesis the peptide resin was transferred to a manual solid phase vessel and washed with methylene chloride and DMF multiple times. Fmoc-Lys(Mtt) 1.2 g (2.0 mM 8 eqv) was added as a solid and 15 mL DMF was added followed by 1.2 mL Dic (7 mM 28 eqv.). The coupling was allowed to proceed until a negative or near negative ninhydrin was obtained. If a negative ninhydrin was not obtained the resin was Acetylated with Ac$_2$O 6 mL, DIEA 1 mL and DMF 18 mL for 30 min and completion checked with ninhydrin. The resin was then washed 3×DMF and 4×CH$_2$Cl$_2$. The Lys (Mtt) and Asp(2Pip) were deprotected 10 times using 2% TFA in CH$_2$Cl$_2$. After deprotection, the peptide resin was washed 2×CH$_2$Cl$_2$; 2×6% TFA/CH$_2$Cl$_2$; 2×6% DIEA/DMF and 2×DMF. The side chain was cyclized with HATU (240 mg 0.625 mM (2.5 eqv.) and DIEA (175 µL 1.0 mM (4 eqv)) and monitored with ninhydrin until negative After completion of the cyclization, the peptide resin was transferred to an ABI vessel for extension to Fmoc-Arg(Pmc)-His(Trt)-Tyr(OBut)-Lys-Asn(Trt)-Leu-Val-Asp-Arg(Pmc)-Gln(Trt)-Arg(Pmc)-Tyr(OBut)-BHA Resin(SEQ ID NO: 30). Fmoc-Pga-OH (160 mg, 313 mM (1.25 eqv)) and HOBt (5 mg, 313 mM (1.25 eqv)) were added as solids and 15 mL DMF was added followed by 1.2 mL Dic (7 mM 28 eqv.). The coupling was allowed to run over night (generally 18 hr.) at room temperature. After washing 4 times with DMF the coupling was monitored with ninhydrin and was generally negative. After standard deprotection and washes, Fmon-Nle-OH (1.2 g, 3.0 mM (12 eqv)) was preactivated with 6.6 mL of 0.45 M HBTT/HOBt in DMF for 3 min and added to the peptide resin. Coupling was allowed to proceed for 3 to 4 hrs, the reaction vessel drained and washed 4 times with DMF. This coupling was monitored with chlorinal (2% Acetaldehyde in DMAc and 2% tetrachloro-1,4-benzoquinone). If the coupling was judged to be incomplete, the resin was recoupled overnight. When the coupling was complete, the resin was deprotected and washed and Fmoc-Ile (1.2 g, 3.0 mM (12 eqv)) was preactivated with 6.6 mL of 0.45 M HBTT/HOBt in DMF for 3 min and added to the peptide resin. Coupling was allowed to proceed for 3 to 4 hrs, the reaction vessel drained and washed 4 times with DMF. This coupling was monitored with ninhydrin and was generally negative. The resin was deprotected and washed and Acetylated with Ac$_2$O 6 mL, DIEA 1 mL and DMF 18 mL for 30 min and completion checked with until a negative or near negative ninhydrin was obtained. If a negative ninhydrin was not obtained the resin was acetylated with Ac$_2$O 6 mL, DIEA 1 mL and DMF 18 mL for 30 min and completion checked with ninhydrin.

After completion of the synthesis, the resin was washed 4 times with CH$_2$Cl$_2$ and dried under a stream of N$_2$. The peptide was deprotected and cleaved from the resin with 1.5 mL triisopropylsilane and 13.5 mL 97% TFA/3% H$_2$O for 180 minutes. The deprotection solution was added to 100 mL cold ET$_2$O, and washed with 1 mL TFA and 30 mL cold ET$_2$O to precipitate the peptide then centrifuged and dried in a desiccator under house vacuum.

The crude peptide was purified and lyophilized by following the procedure described in Example 3 to yield 49 mg (9%) of white amorphous powder. (ES)+-LCMS m/e calcd for $C_{100}H_{151}N_{33}O_{22}$ 2167.53 found 2167.80.

Example 51

Preparation of H-Ile-Lys-Cms-Arg-His-Tyr-Leu-Asn-Leu-Val-Thr-Arg-Gln-Arg-Tyr-NH$_2$ (SEQ ID NO: 5)

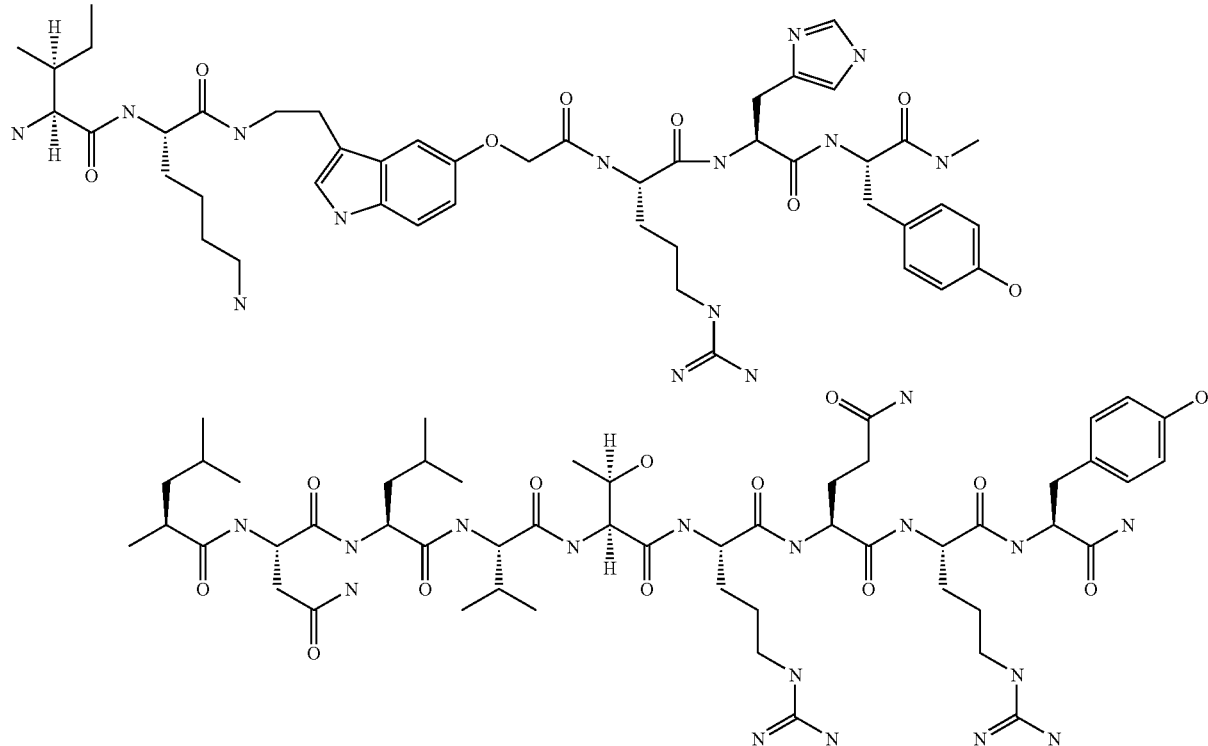

Fmoc-Linker-BHA resin (450 mg, 0.25 mmol) from Example 1 was subjected to solid phase synthesis and purification by following the procedure in Example 3 to yield 44 mg (8%) of white amorphous powder. (ES)+-LCMS m/e calcd for $C_{96}H_{151}N_{31}O_{21}$ 2075.47 found 2074.80.

Example 52

Preparation of H-Ile-Lys-Gly-Cms-Arg-His-Tyr-Leu-Asn-Leu-Val-Thr-Arg-Gln-Arg-Tyr-NH$_2$ (SEQ ID NO: 5)

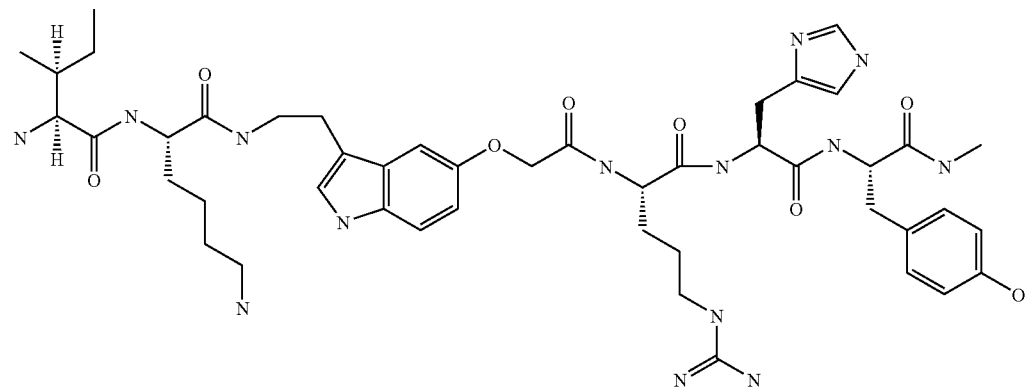

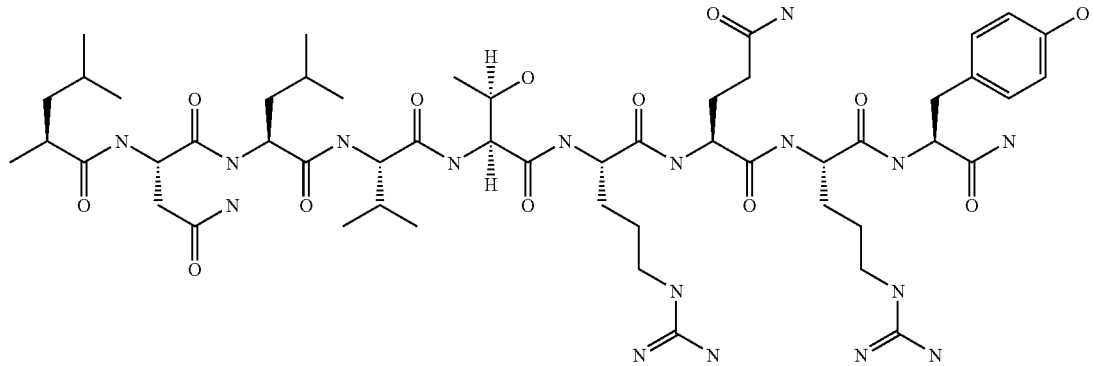

Fmoc-Linker-BHA resin (450 mg, 0.25 mmol) from Example 1 was subjected to solid phase synthesis and purification by following the procedure in Example 3 to yield 129 mg (24%) of white amorphous powder. (ES)+-LCMS m/e calcd for $C_{98}H_{154}N_{32}O_{22}$ 2132.52 found 2133.00.

Example 53

Preparation of Cyclo Lys28-Aspu32 Ac-Ile-Nle-Cms-Arg-His-Tyr-Lys-Asn-Leu-Val-Asp-Arg-Gln-Arg-Tyr-NH$_2$ (SEQ ID NO: 28)

This peptide was prepared through a combination of automated synthesis on an ABI 433 and manual synthesis on a 0.25 mM scale according to the procedure disclosed in Example 50. Fmoc-Cms-OH (151 mg, 313 mM (1.25 eqv)) and HOBt (45 mg, 313 mM (1.25 eqv)) were added as solids and 15 mL DMF was added followed by 1.2 mL Dic (7 mM 28 eqv.). The coupling was allowed to run over night (generally 18 hr.) at room temperature.

The crude peptide was purified and lyophilized to yield 19 mg (9%) of white amorphous powder. (ES)+-LCMS m/e calcd for $C_{98}H_{149}N_{31}O_{22}$ 2113.47 found 2113.80.

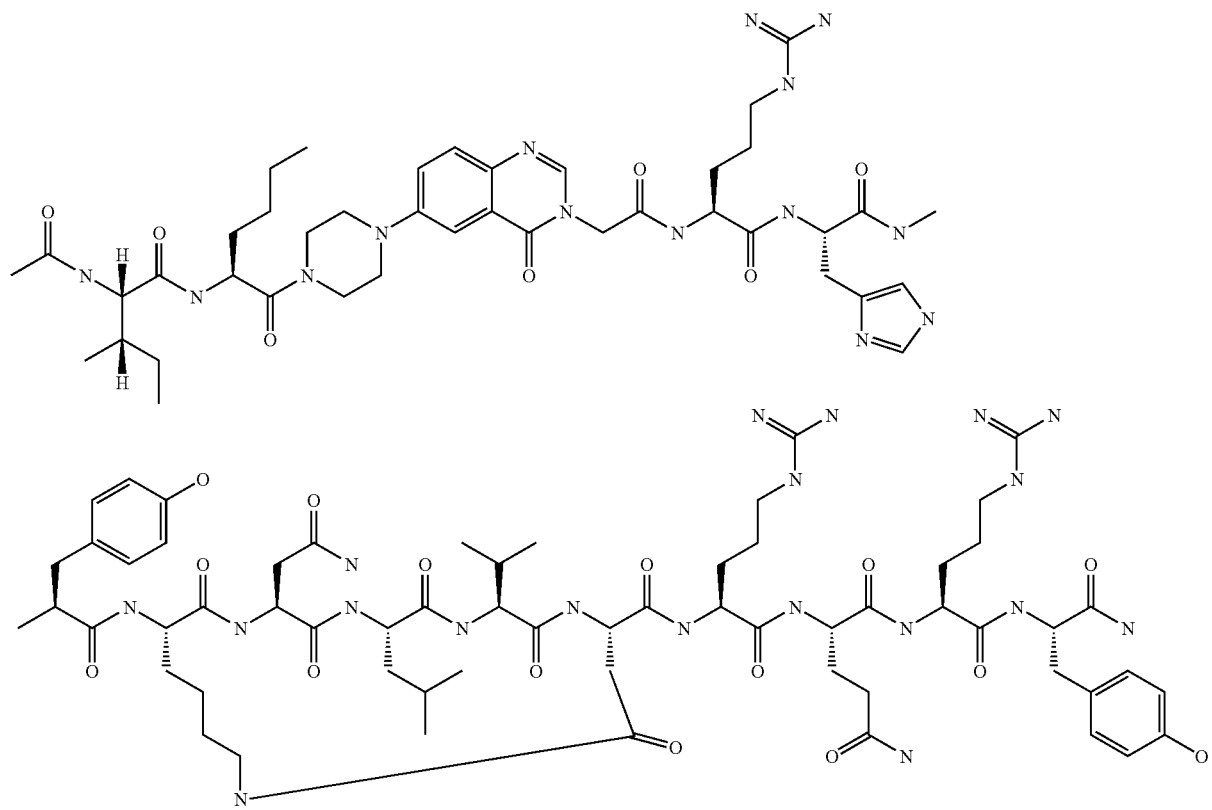

Example 54

Preparation of Ac-Ile-Nle-Pqa-Arg-His-Tic-Leu-Asn-Leu-Val-Thr-Arg-Gln-Arg-Tyr-NH$_2$ (SEQ ID NO: 31)

Fmoc-Linker-BHA resin (450 mg, 0.25 mmol) from Example 1 was subjected to solid phase synthesis (Tic was inserted in position 27 of the sequence) and purification by following the procedure in Example 3 to yield 87 mg (16%) of white amorphous powder. (ES)+-LCMS m/e calcd for $C_{101}H_{154}N_{32}O_{21}$ 2152.56 found 2152.50.

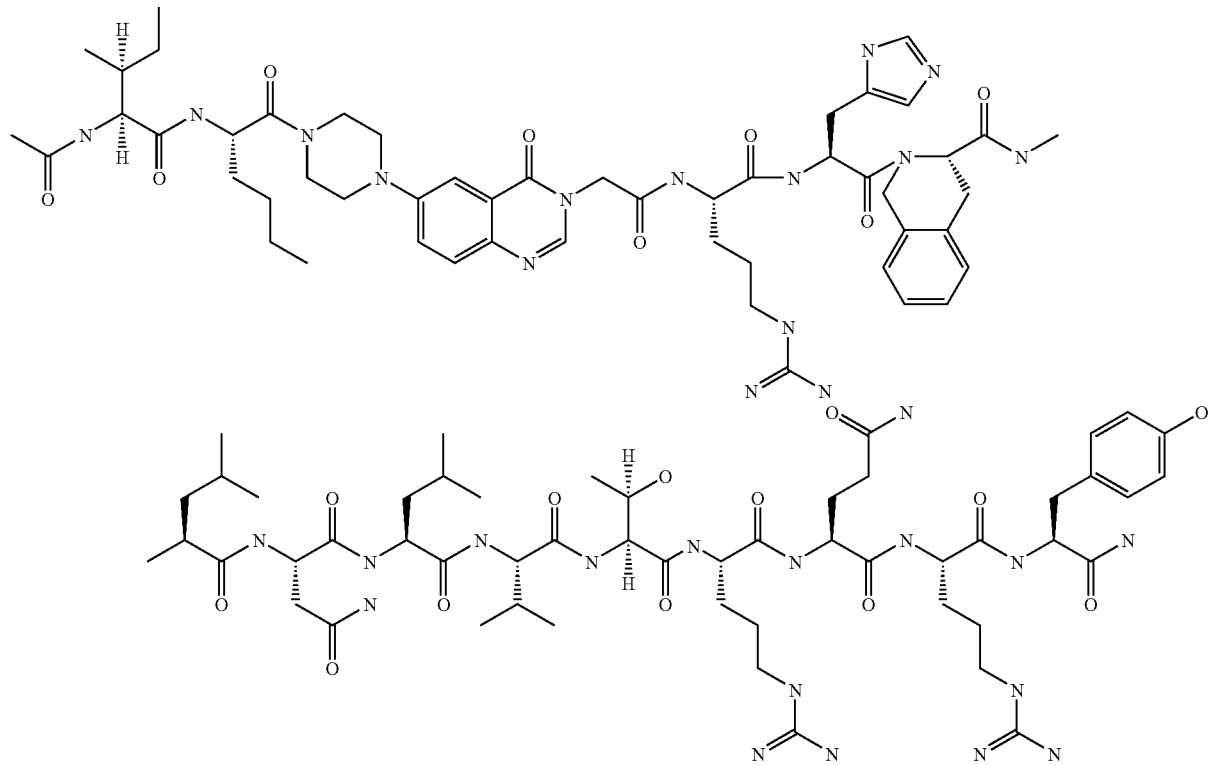

Example 55

Preparation of Ac-Ile-Nle-Pqa-Arg-His-Bip-Leu-Asn-Leu-Val-Thr-Arg-Gln-Arg-Tyr-NH$_2$ (SEQ ID NO: 32)

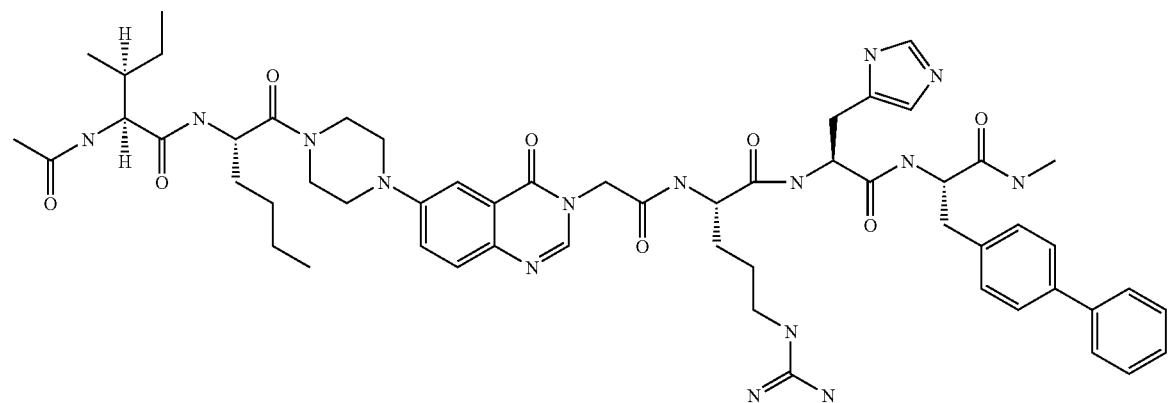

-continued

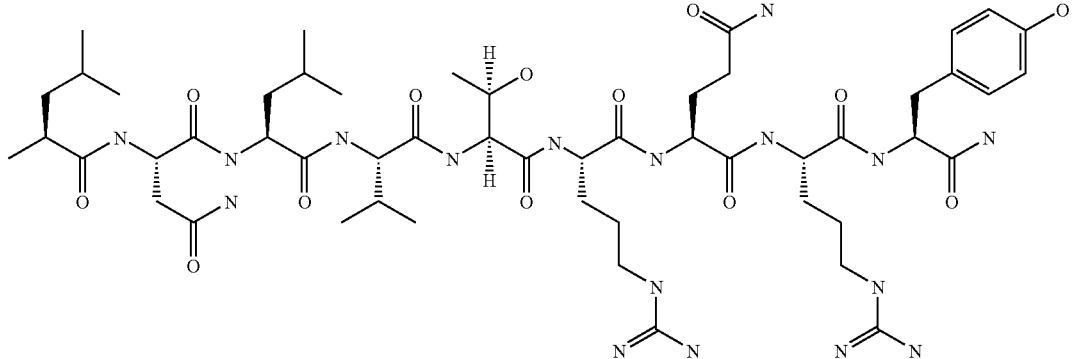

Fmoc-Linker-BHA resin (450 mg, 0.25 mmol) from Example 1 was subjected to solid phase synthesis (Bip was inserted in position 27 of the sequence) and purification by following the procedure in Example 3 to yield 90 mg (16%) of white amorphous powder. (ES)+-LCMS m/e calcd for $C_{106}H_{158}N_{32}O_{21}$ 2216.64 found 2217.00.

Fmoc-Linker-BHA resin (450 mg, 0.25 mmol) from Example 1 was subjected to solid phase synthesis (Dip was inserted in position 27 of the sequence) and purification by following the procedure in Example 3 to yield 84 mg (15%) of white amorphous powder. (ES)+-LCMS m/e calcd for $C_{106}H_{158}N_{32}O_{21}$ 2216.64 found 2217.30.

Example 56

Preparation of Ac-Ile-Nle-Pqa-Arg-His-Dip-Leu-Asn-Leu-Val-Thr-Arg-Gln-Arg-Tyr-NH₂ (SEQ ID NO: 33)

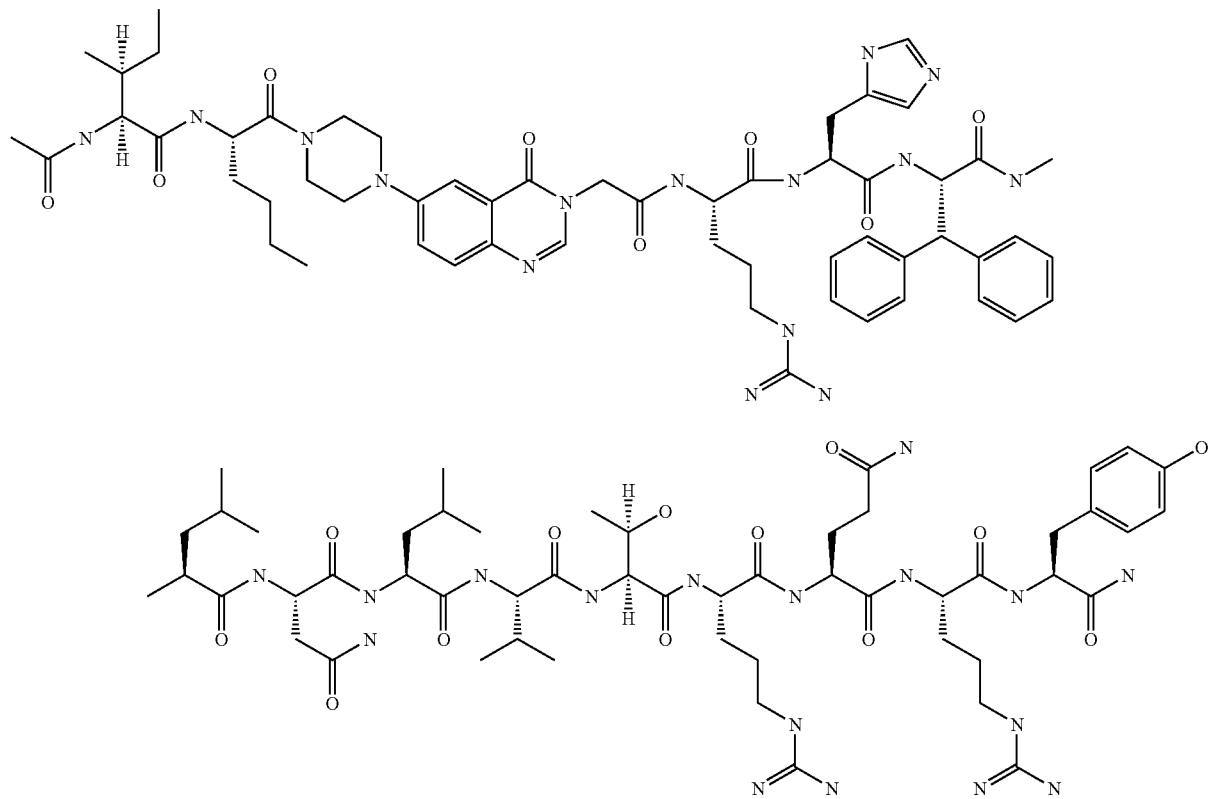

Example 57

Preparation of Ac-Ile-Nle-Pqa-Arg-His-(1)Nal-Leu-Asn-Leu-Val-Thr-Arg-Gln-Arg-Tyr-NH$_2$ (SEQ ID NO: 34)

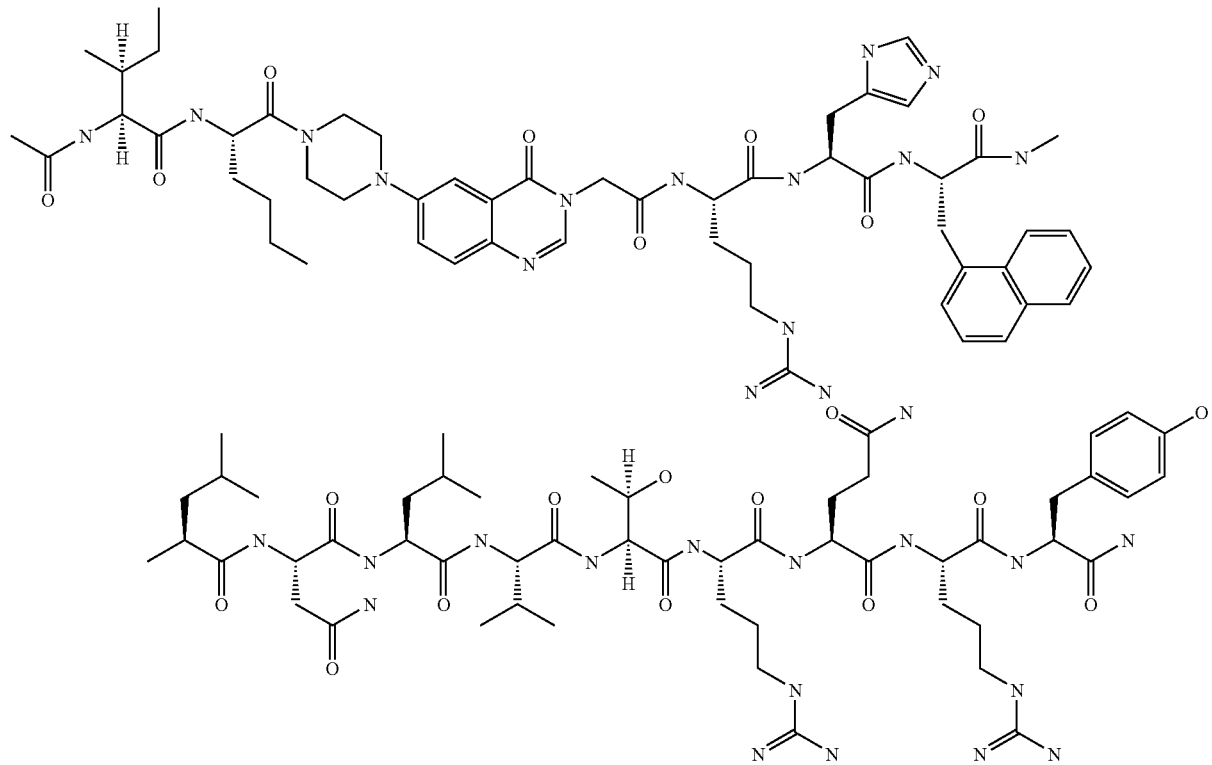

Fmoc-Linker-BHA resin (450 mg, 0.25 mmol) from Example 1 was subjected to solid phase synthesis ((1) Nal was inserted in position 27 of the sequence) and purification by following the procedure in Example 3 to yield 88 mg (16%) of white amorphous powder. (ES)+-LCMS m/e calcd for C$_{104}$H$_{156}$N$_{32}$O$_{21}$ 2190.60 found 2190.61.

Example 58

Preparation of Ac-Ile-Nle-Pqa-Arg-His-(2)Nal-Leu-Asn-Leu-Val-Thr-Arg-Gln-Arg-Tyr-NH$_2$ (SEQ ID NO: 35)

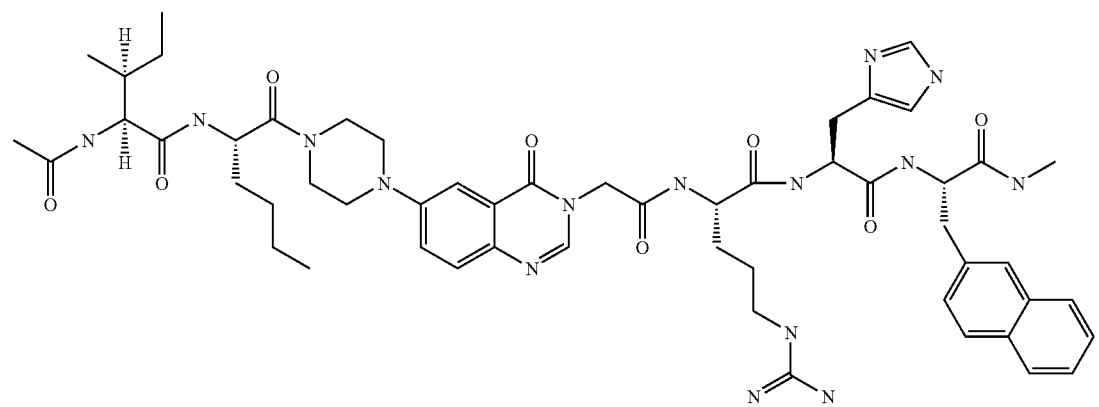

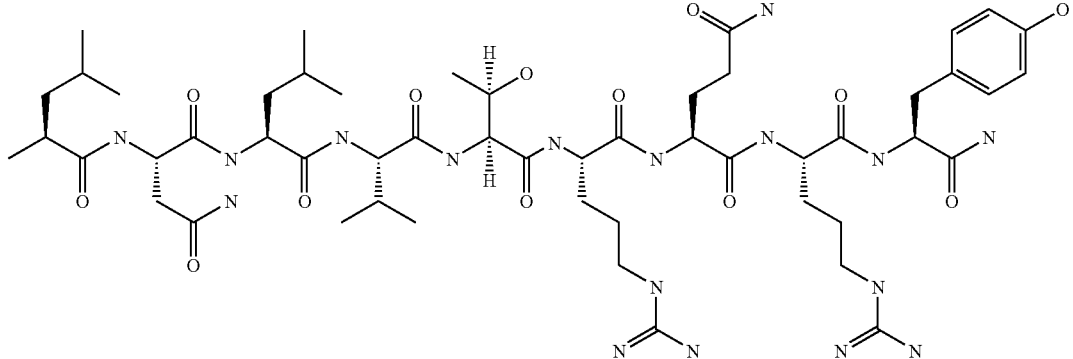

Fmoc-Linker-BHA resin (450 mg, 0.25 mmol) from Example 1 was subjected to solid phase synthesis ((2) Nal was inserted in position 27 of the sequence) and purification by following the procedure in Example 3 to yield 40 mg (7%) of white amorphous powder. (ES)+-LCMS m/e calcd for $C_{104}H_{156}N_{32}O_{21}$ 2190.60 found 2191.20.

Fmoc-Linker-BHA resin (450 mg, 0.25 mmol) from Example 1 was subjected to solid phase synthesis (3,4,5, trifluoro Phe was inserted in position 27 of the sequence) and purification by following the procedure in Example 3 to yield 101.4 mg (18%) of white amorphous powder. (ES)+-LCMS m/e calcd for $C_{100}H_{151}F_3N_{32}O_{21}$ 2194.52 found 2194.20.

Example 59

Preparation of Ac-Ile-Nle-Pqa-Arg-His-(3,4,5trifluo-rPhe)-Leu-Asn-Leu-Val-Thr-Arg-Gln-Arg-Tyr-NH$_2$
(SEQ ID NO: 36)

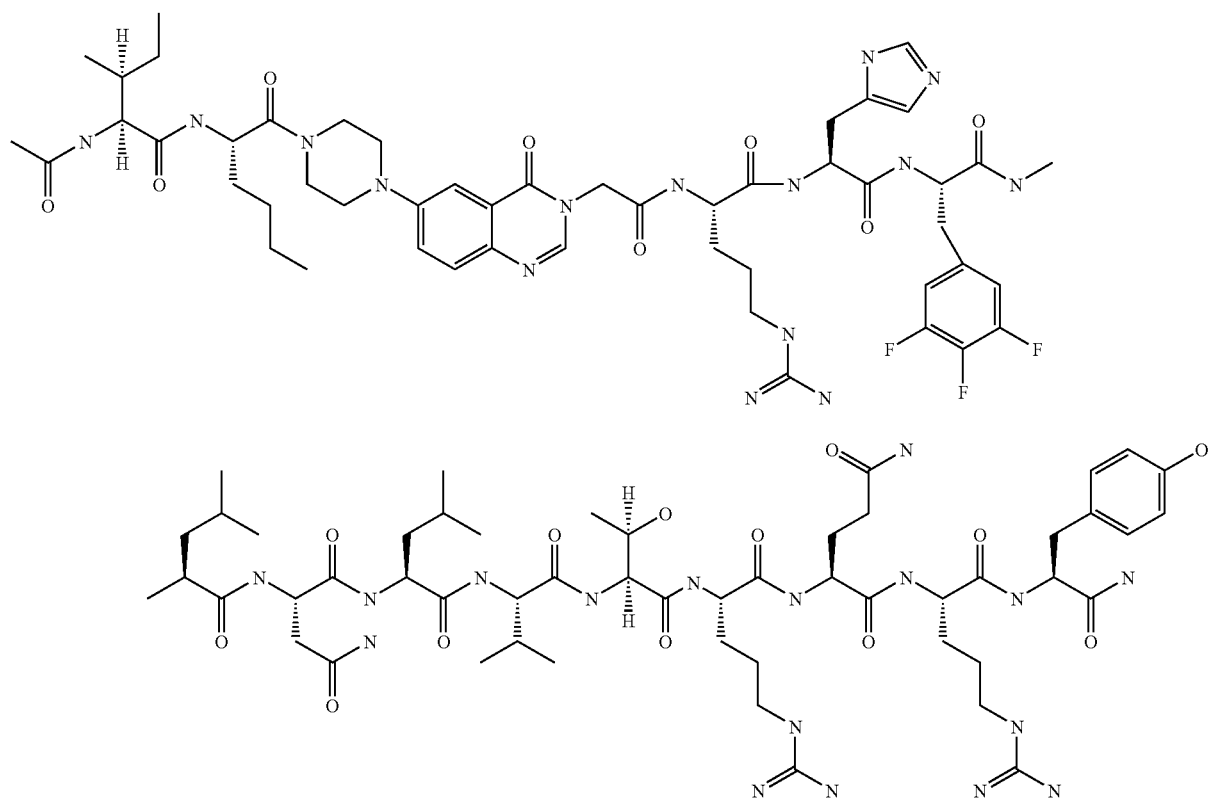

Example 60

Preparation of Ac-Ile-Nle-Pqa-Arg-His-(2,3,4,5,6 Penta fluoroPhe)-Leu-Asn-Leu-Val-Thr-Arg-Gln-Arg-Tyr-NH₂ (SEQ ID NO: 37)

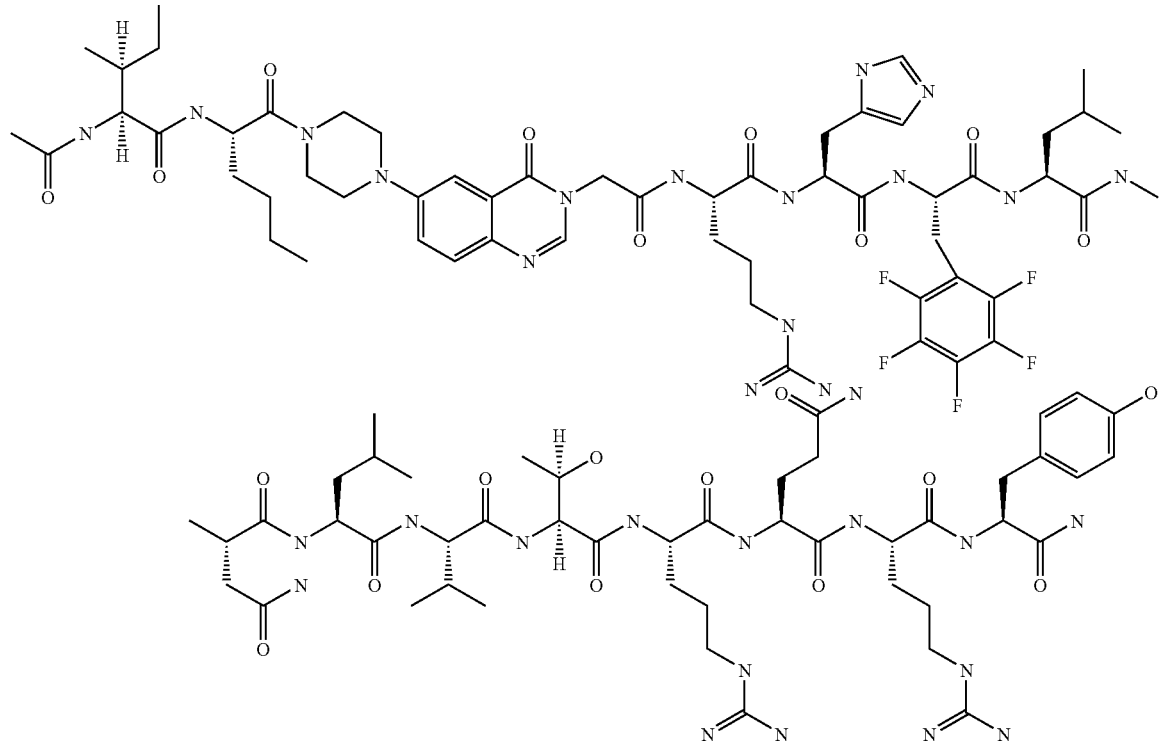

Fmoc-Linker-BHA resin (450 mg, 0.25 mmol) from Example 1 was subjected to solid phase synthesis (2,3,4,5,6, pentafluoro Phe was inserted in position 27 of the sequence) and purification by following the procedure in Example 3 to yield 122.5 mg (22%) of white amorphous powder. (ES)+- LCMS m/e calcd for $C_{100}H_{149}F_5N_{32}O_{21}$ 2230.50 found 2230.50.

Example 61

Preparation of Ac-Ile-Nle-Pqa-Arg-(4-MeOApc)- Tyr-Leu-Asn-Leu-Val-Thr-Arg-Gln-Arg-Tyr-NH₂ (SEQ ID NO: 38)

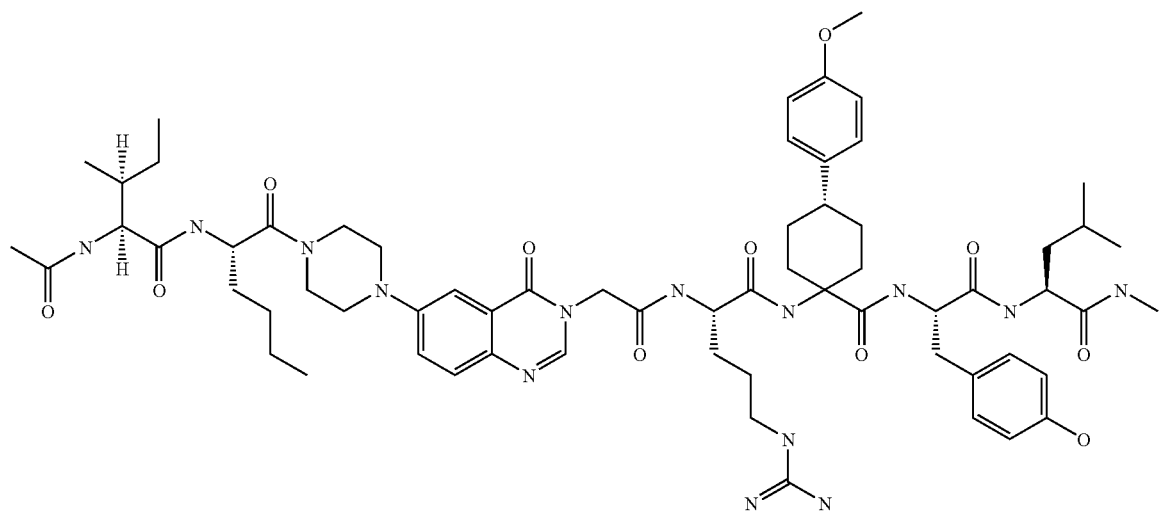

-continued

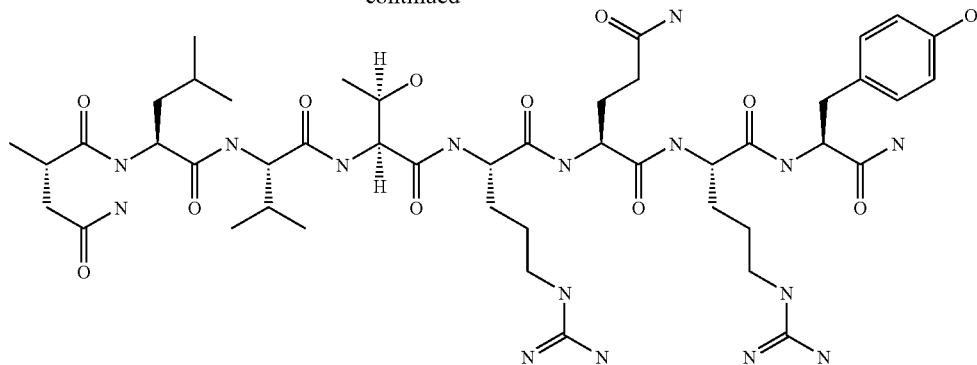

Fmoc-Linker-BHA resin (450 mg, 0.25 mmol) from Example 1 was subjected to solid phase synthesis ((4-MeO-Apc) was inserted in position 26 of the sequence) and purification by following the procedure in Example 3 to yield 43 mg (8%) of white amorphous powder. (ES)+-LCMS m/e calcd for $C_{108}H_{164}N_{30}O_{23}$ 2250.70 found 2250.60.

Fmoc-Linker-BHA resin (450 mg, 0.25 mmol) from Example 1 was subjected to solid phase synthesis ((3-Pal) was inserted in position 26 of the sequence) and purification by following the procedure in Example 3 to yield 112 mg (21%) of white amorphous powder. (ES)+-LCMS m/e calcd for $C_{102}H_{155}N_{31}O_{22}$ 2167.57 found 2167.20.

Example 62

Preparation of Ac-Ile-Nle-Pqa-Arg-(3-Pal)-Tyr-Leu-Asn-Leu-Val-Thr-Arg-Gln-Arg-Tyr-NH$_2$ (SEQ ID NO: 39)

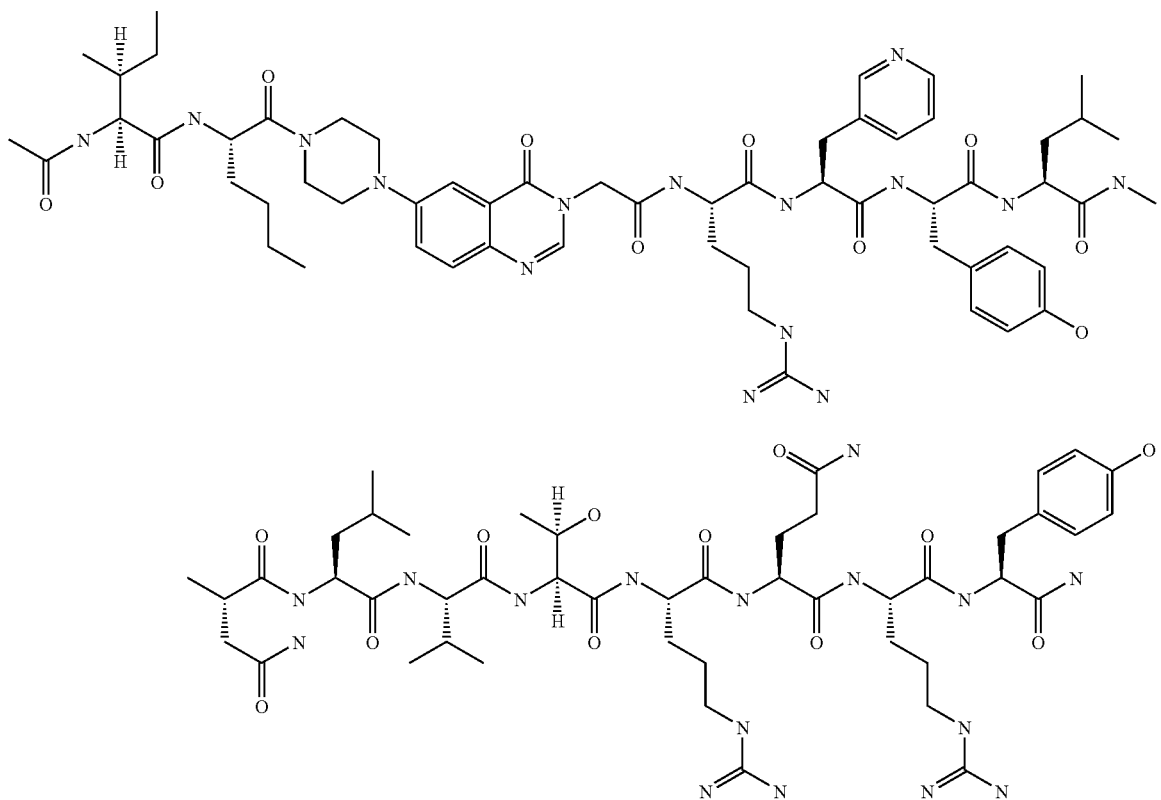

Example 63

Preparation of Ac-Ile-Nle-Pqa-Arg-(4-Pal)-Tyr-Leu-Asn-Leu-Val-Thr-Arg-Gln-Arg-Tyr-NH$_2$ (SEQ ID NO: 40)

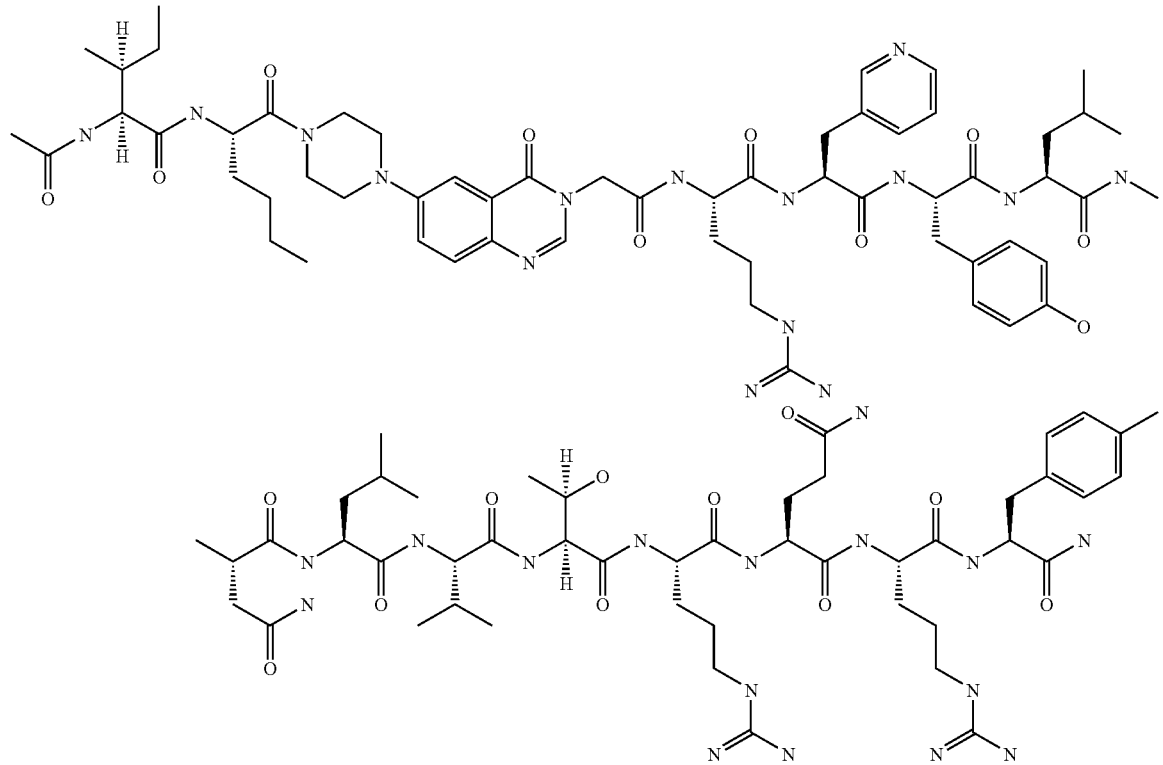

Fmoc-Linker-BHA resin (450 mg, 0.25 mmol) from Example 1 was subjected to solid phase synthesis ((4-Pal) was inserted in position 26 of the sequence) and purification by following the procedure in Example 3 to yield 146 mg (27%) of white amorphous powder. (ES)+-LCMS m/e calcd for C$_{102}$H$_{155}$N$_{31}$O$_{22}$ 2167.57 found 2167.20.

Example 64

Preparation of Ac-Ile-Nle-Pqa-(3,4,5 Trifluoro Phe)-His-Tyr-Leu-Asn-Leu-Val-Thr-Arg-Gln-Arg-Tyr-NH$_2$ (SEQ ID NO: 41)

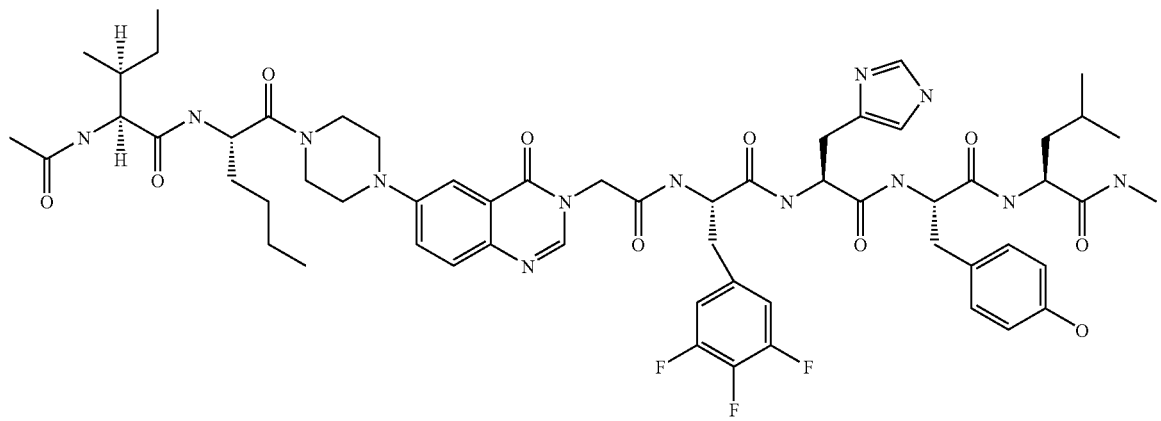

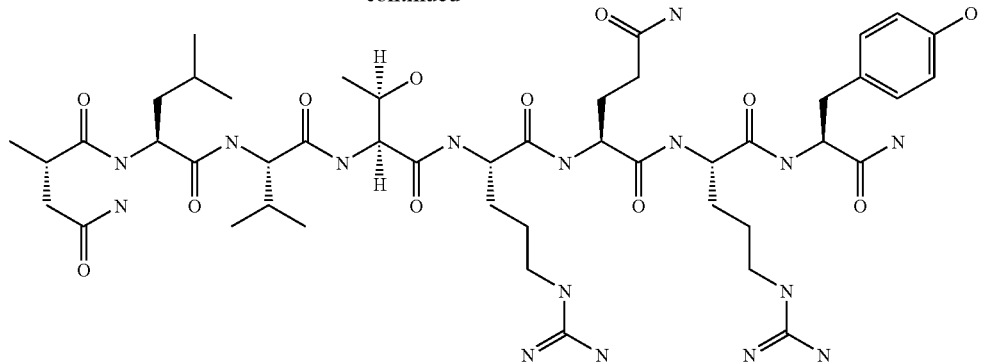

Fmoc-Linker-BHA resin (450 mg, 0.25 mmol) from Example 1 was subjected to solid phase synthesis ((3,4,5 trifluoro Phe) was inserted in position 25 of the sequence) and purification by following the procedure in Example 3 to yield 55 mg (10%) of white amorphous powder. (ES)+-LCMS m/e calcd for $C_{103}H_{148}F_3N_{29}O_{22}$ 2201.50 found 2201.40.

Fmoc-Linker-BHA resin (450 mg, 0.25 mmol) from Example 1 was subjected to solid phase synthesis ((2,3,4,5,6 Pentafluoro Phe) was inserted in position 25 of the sequence) and purification by following the procedure in Example 3 to yield 65 mg(12%) of white amorphous powder. (ES)+-LCMS m/e calcd for $C_{103}H_{146}F_5N_{29}O_{22}$ 2237.49 found 2237.70.

Example 65

Preparation of Ac-Ile-Nle-Pqa-(2,3,4,5,6 Penta fluoro Phe)-His Tyr-Leu-Asn-Leu-Val-Thr-Arg-Gln-Arg-Tyr-NH$_2$ (SEQ ID NO: 42)

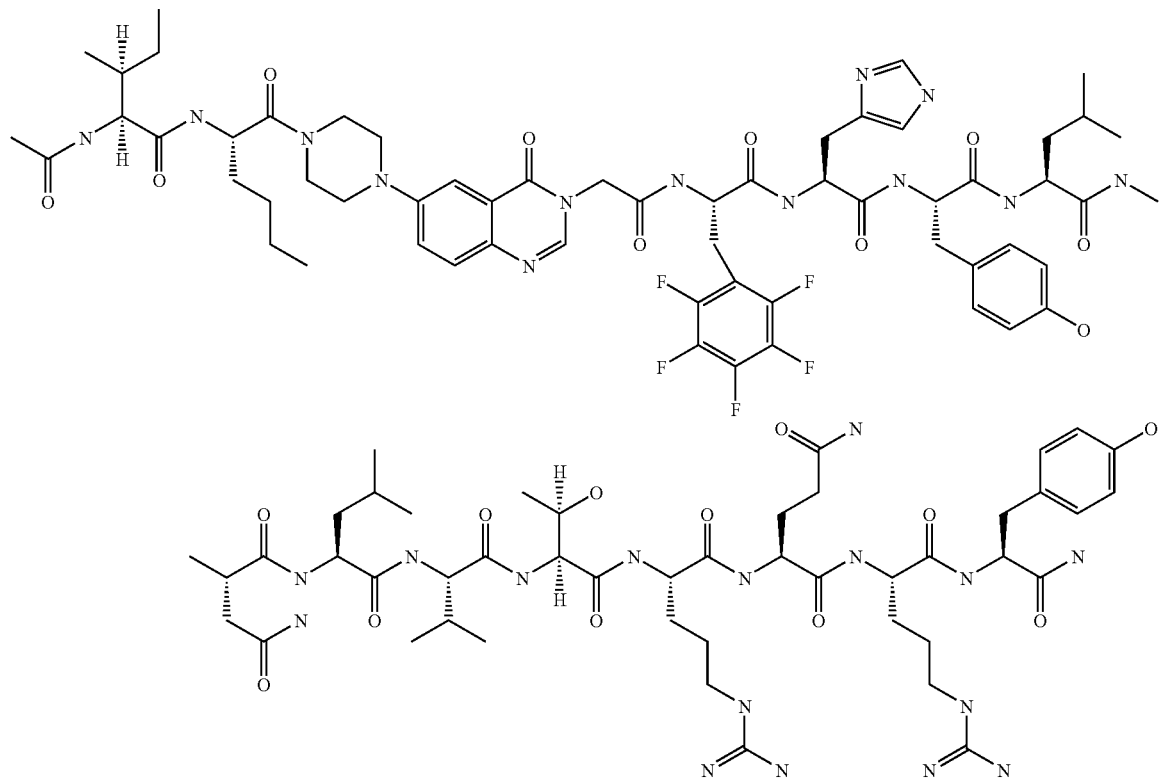

Example 66

Preparation of Ac-Aib-Nle-Pqa-Arg-His-Tyr-Leu-Asn-Leu-Val-Thr-Arg-Gln-Arg-Tyr-NH$_2$ (SEQ ID NO: 5)

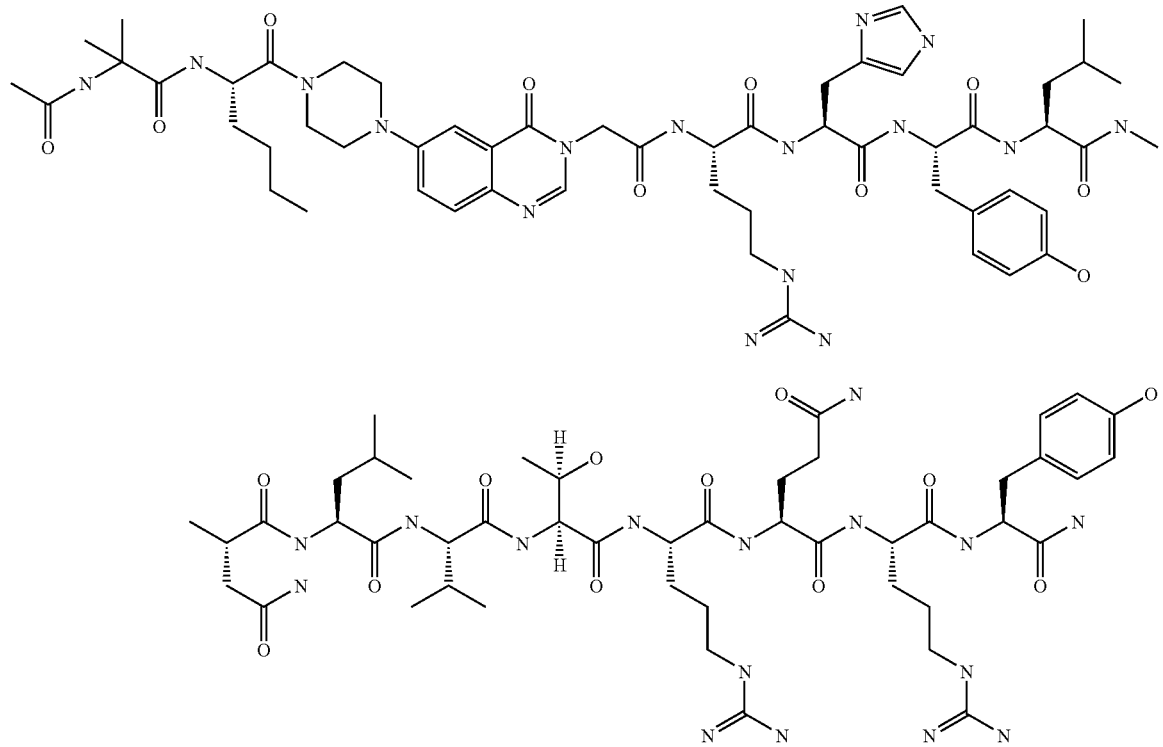

Fmoc-Linker-BHA resin (450 mg, 0.25 mmol) from Example 1 was subjected to solid phase synthesis ((Aib) was inserted in position 3 of the sequence) and purification by following the procedure in Example 3 to yield 32 mg (6%) of white amorphous powder. (ES)+-LCMS m/e calcd for C$_{98}$H$_{150}$N$_{32}$O$_{22}$ 2128.49 found 2128.00.

Example 67

Preparation of Ac-1,1-Aic-Nle-Pqa-Arg-His-Tyr-Leu-Asn-Leu-Val-Thr-Arg-Gln-Arg-Tyr-NH$_2$ (SEQ ID NO: 5)

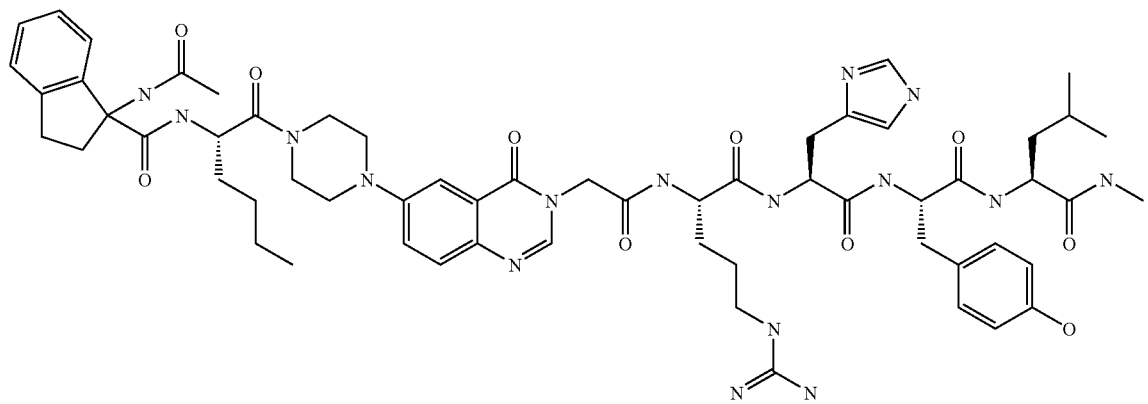

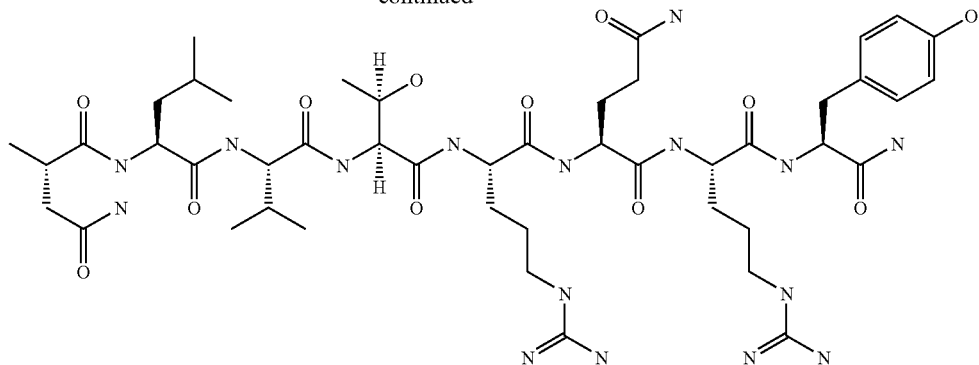

Fmoc-Linker-BHA resin (450 mg, 0.25 mmol) from Example 1 was subjected to solid phase synthesis ((1,1 Aic) was inserted in position 3 of the sequence) and purification by following the procedure in Example 3 to yield a racemic mixture separated as Pk A: 31 mg (6%) of white amorphous powder. (ES)+-LCMS m/e calcd for $C_{104}H_{152}N_{32}O_{22}$ 2202.57 found 2202.60.

Fmoc-Linker-BHA resin (450 mg, 0.25 mmol) from Example 1 was subjected to solid phase synthesis ((1,1 Aic) was inserted in position 3 of the sequence) and purification by following the procedure in Example 3 to yield a racemic mixture separated as Pk. B: 46 mg (8%) of white amorphous powder. (ES)+-LCMS m/e calcd for Pk B. $C_{104}H_{152}N_{32}O_{22}$ 2202.57 found 2202.60.

Example 68

Preparation of Ac-1,1-Aic-Nle-Pqa-Arg-His-Tyr-Leu-Asn-Leu-Val-Thr-Arg-Gln-Arg-Tyr-NH$_2$ (SEQ ID NO: 5)

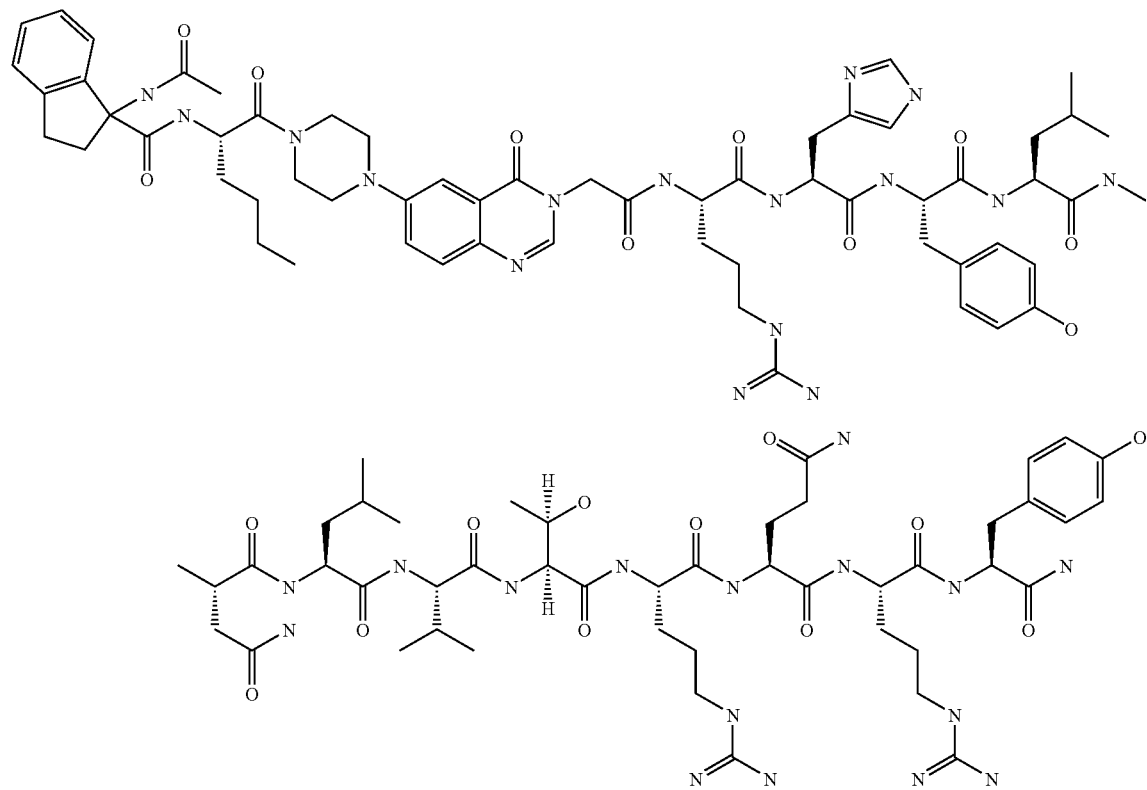

Example 69

Preparation of Ac-2,2-Aic-Nle-Pqa-Arg-His-Tyr-Leu-Asn-Leu-Val-Thr-Arg-Gln-Arg-Tyr-NH$_2$ (SEQ ID NO: 5)

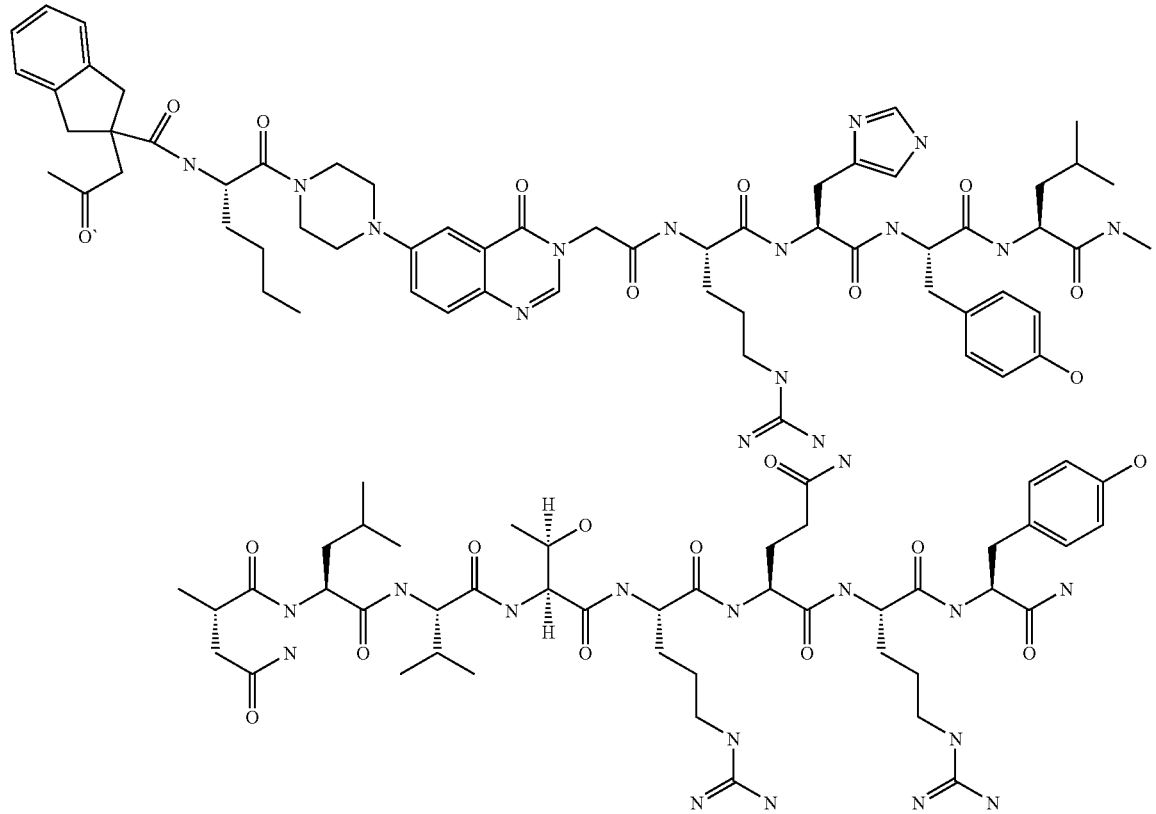

Fmoc-Linker-BHA resin (450 mg, 0.25 mmol) from Example 1 was subjected to solid phase synthesis ((2,2 Aic) was inserted in position 3 of the sequence) and purification by following the procedure in Example 3 to yield 103 mg (19%) of white amorphous powder. (ES)+-LCMS m/e calcd for C$_{104}$H$_{152}$N$_{32}$O$_{22}$ 2202.57 found 2202.30.

Example 70

Preparation of Ac-Ach-Nle-Pqa-Arg-His-Tyr-Leu-Asn-Leu-Val-Thr-Arg-Gln-Arg-Tyr-NH$_2$ (SEQ ID NO: 5)

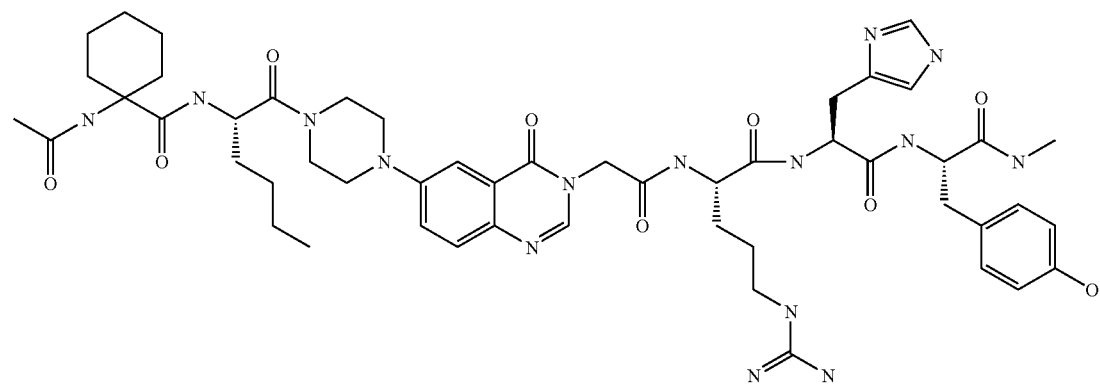

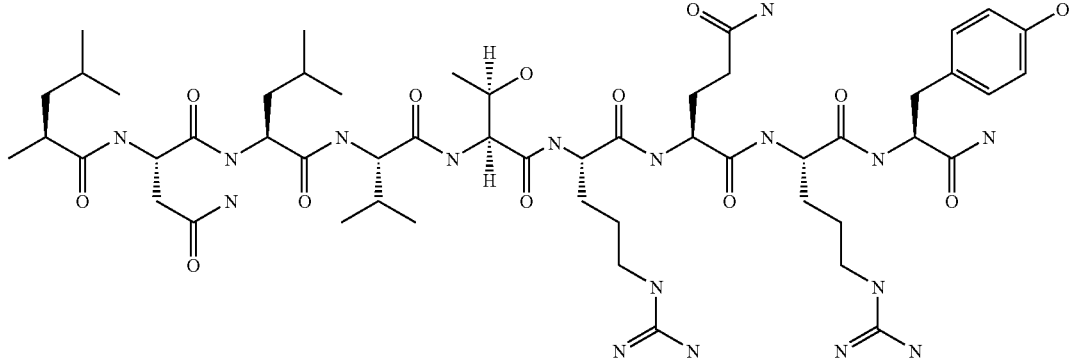

Fmoc-Linker-BHA resin (450 mg, 0.25 mmol) from Example 1 was subjected to solid phase synthesis (Ach was inserted in position 3 of the sequence) and purification by following the procedure in Example 3 to yield 81 mg (15%) of white amorphous powder. (ES)+-LCMS m/e calcd for $C_{101}H_{154}N_{32}O_{22}$ 2168.55 found 2168.10.

Example 71

Preparation of Ac-Acp-Nle-Pqa-Arg-His-Tyr-Leu-Asn-Leu-Val-Thr-Arg-Gln-Arg-Tyr-NH$_2$ (SEQ ID NO: 5)

Fmoc-Linker-BHA resin (450 mg, 0.25 mmol) from Example 1 was subjected to solid phase synthesis (Acp was inserted in position 3 of the sequence) and purification by following the procedure in Example 3 to yield 95 mg (18%) of white amorphous powder. (ES)+-LCMS m/e calcd for $C_{100}H_{152}N_{32}O_{22}$ 2154.53 found 2154.30.

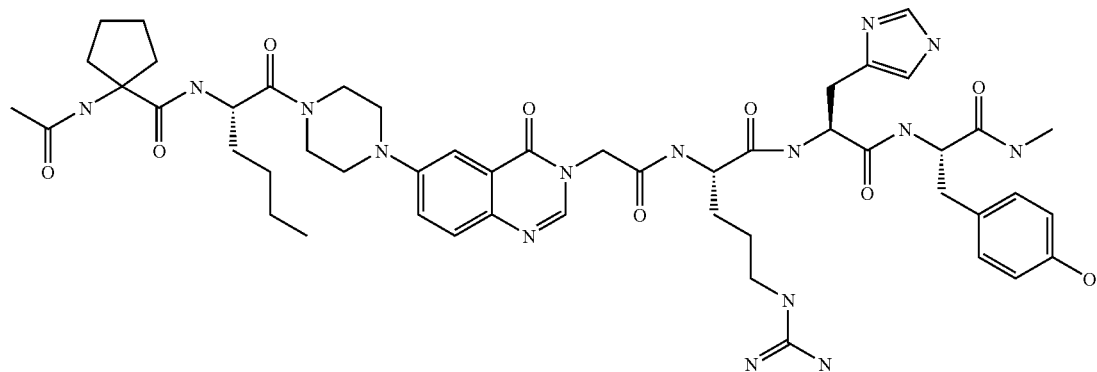

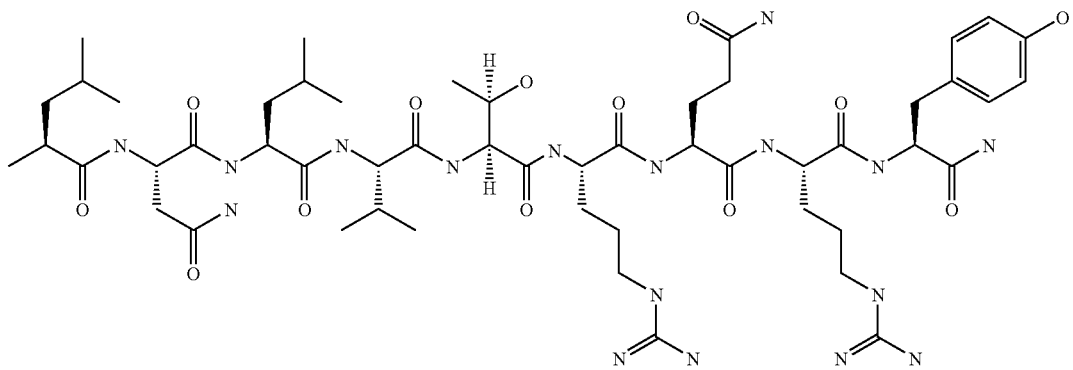

Example 72

Preparation of H-Ile-Nle-Pqa-Arg-His-Tyr-Leu-Asn-Leu-Val-Thr-Arg-Gln-Arg-Tyr-NH$_2$ (SEQ ID NO: 5)

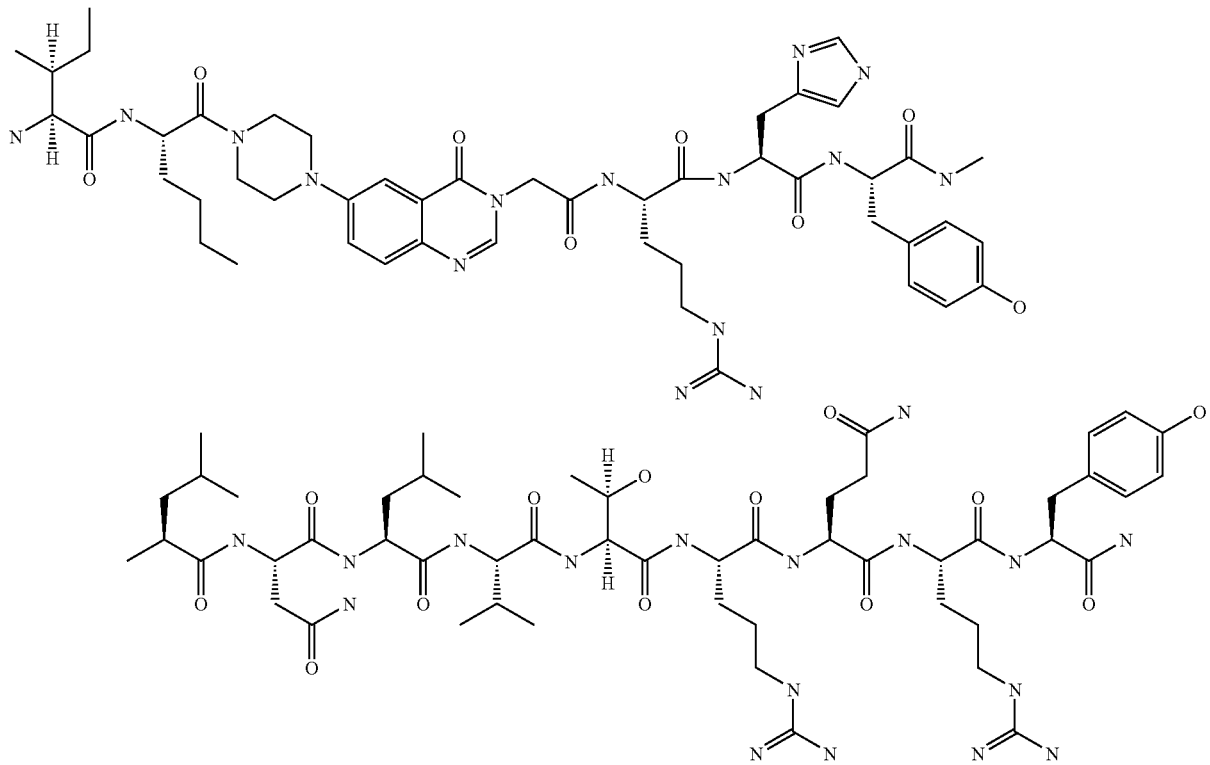

Fmoc-Linker-BHA resin (450 mg, 0.25 mmol) from Example 1 was subjected to solid phase synthesis and purification by following the procedure in Example 3 to yield 80 mg (15%) of white amorphous powder. (ES)+-LCMS m/e calcd for C$_{98}$H$_{152}$N$_{32}$O$_{21}$ 2114.51 found 2113.80.

Example 73

Preparation of PEG (10,000)-Ile-Nle-Pqa-Arg-His-Tyr-Leu-Asn-Leu-Val-Thr-Arg-Gln-Arg-Tyr-NH$_2$ (SEQ ID NO: 5)

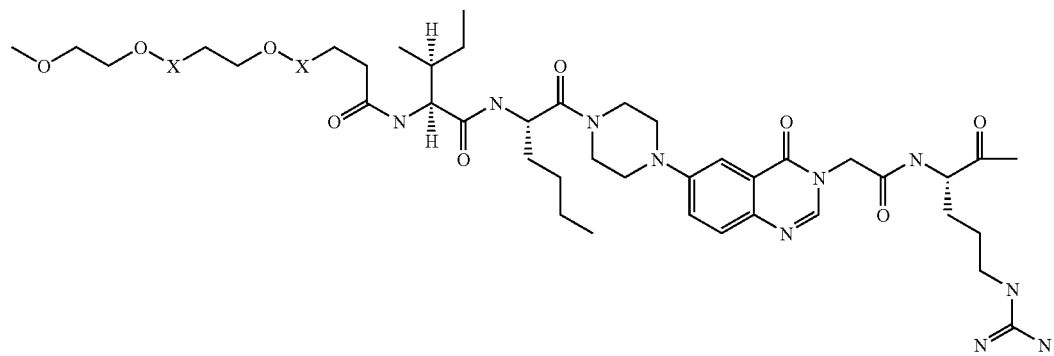

-continued

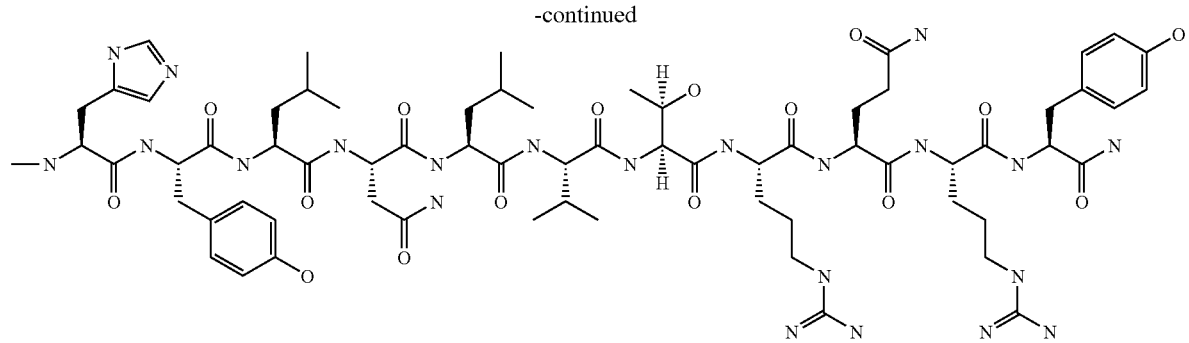

Fifteen mg of peptide from example 72 was weighed out and dissolved in 50 mM Borate, pH 7.4 buffer. 107 mg 10 kDa PEG-SPA (Nektar) was weighed to achieve a 2:1 PEG:peptide molar ratio and added to the dissolved peptide. The reaction mixture was agitated at room temperature for 2 h before it was diluted 10-fold in 20 mM NaOAc, pH 4.5 buffer and purified by cation exchange chromatography on SP-Sepharose FF (Amersham). FIG. 1 is an HPLC chromatogram of 10 kDa PEG-PYY peptide. The reaction yielded 67.8% of 10 kDa PEG-peptide.

Mono-pegylated PYY peptide was eluted using a step NaCl gradient. Typically, the desired mono-pegylated peptide eluted with 125 mM NaCl. The eluted PEG-PYY peptide was concentrated in an Amicon ultrafiltration cell using a 10 kDa MW cutoff membrane. It was then diafiltered 10-fold once with PBS.

Figure 2:
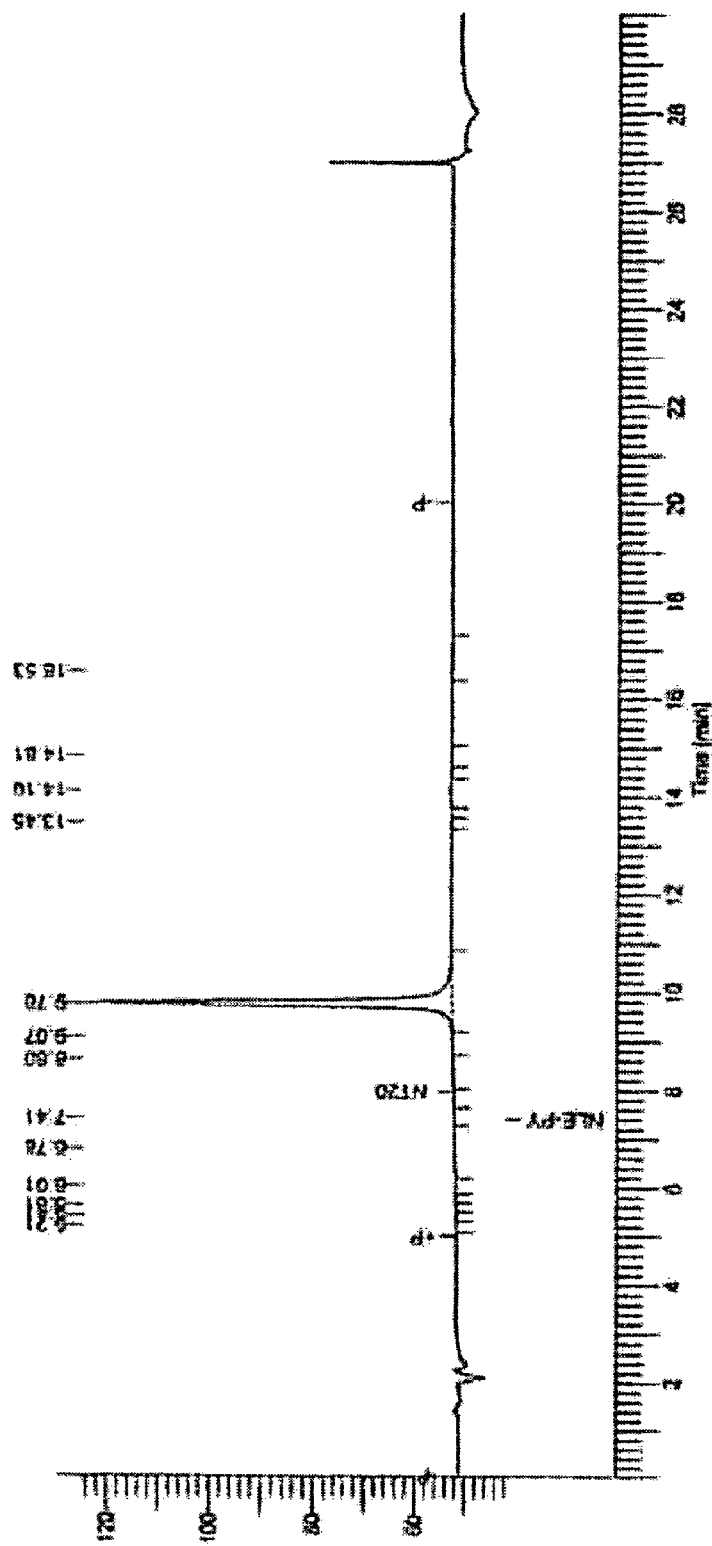
FIG. 2 shows a HPLC chromatogram of a compound of the present invention.
Figure 3:
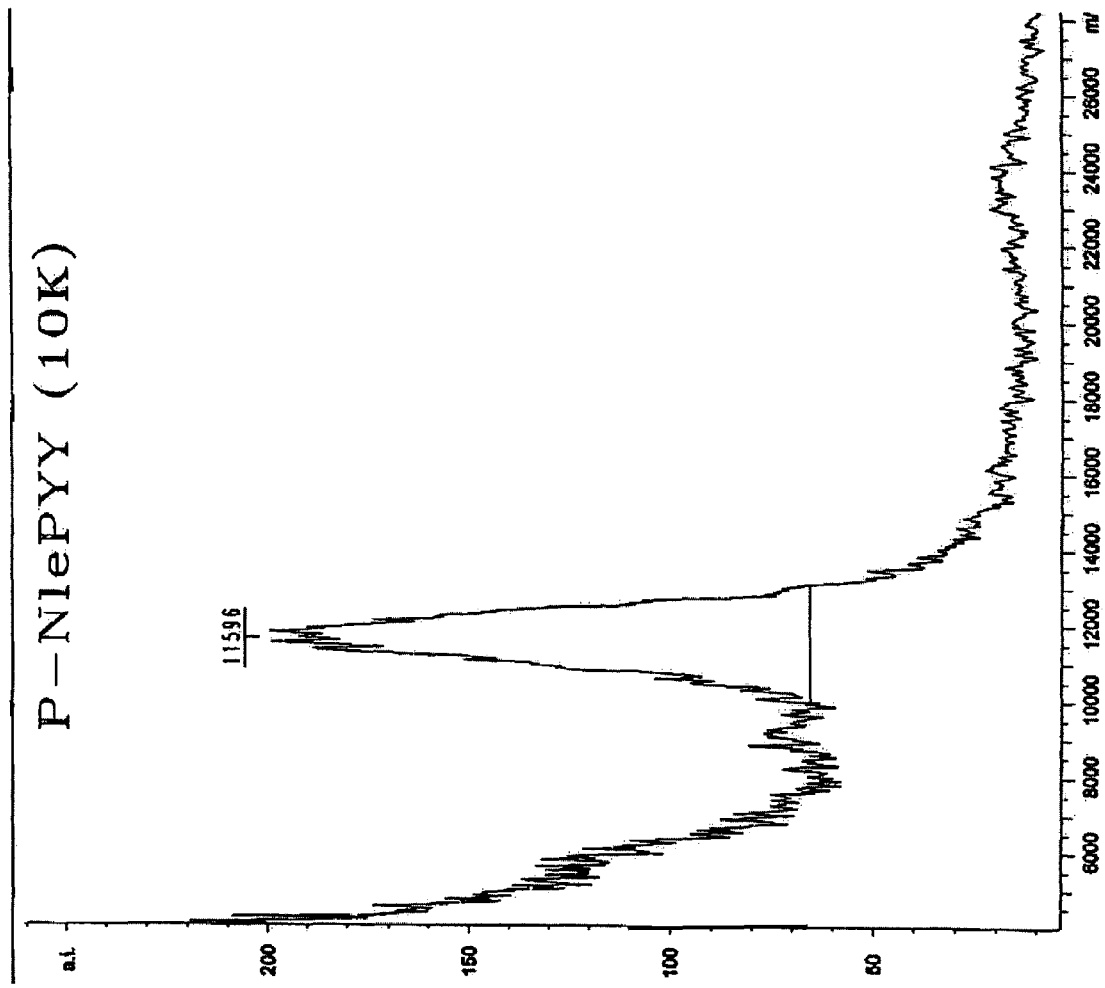
FIG. 3 shows a MALDI-TOF of a compound of the present invention.

Concentrated peptide of example 73 was submitted for analysis, assayed and stored at −20 C. FIG. 2 is an HPLC chromatogram of purified 10 kDa PEG-PYY peptide. Purity of 10 kDa peptide was determined to be 97.6%. And FIG. 3 is a graph representing a MALDI-TOF of 10 kDa PEG-peptide performed to confirm the molecular weight.

Example 74

Preparation of PEG (30,000)-Ile-Nle-Pqa-Arg-His-Tyr-Leu-Asn-Leu-Val-Thr-Arg-Gln-Arg-Tyr-NH$_2$
(SEQ ID NO: 5)

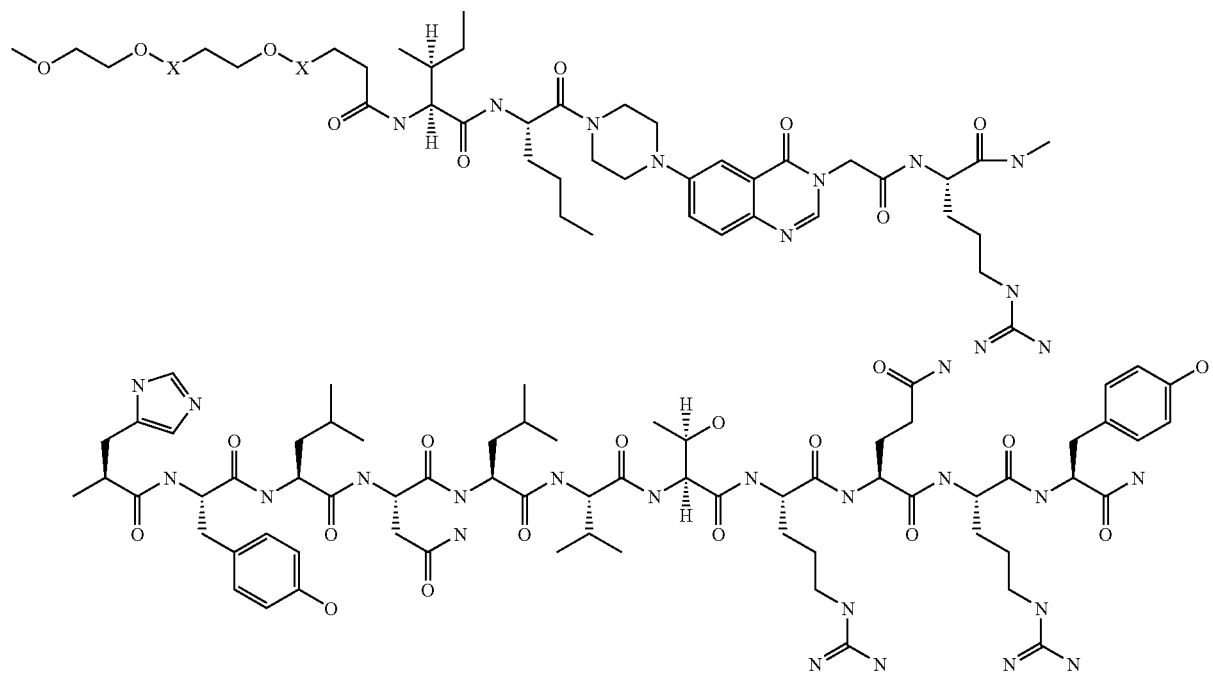

Figure 4:
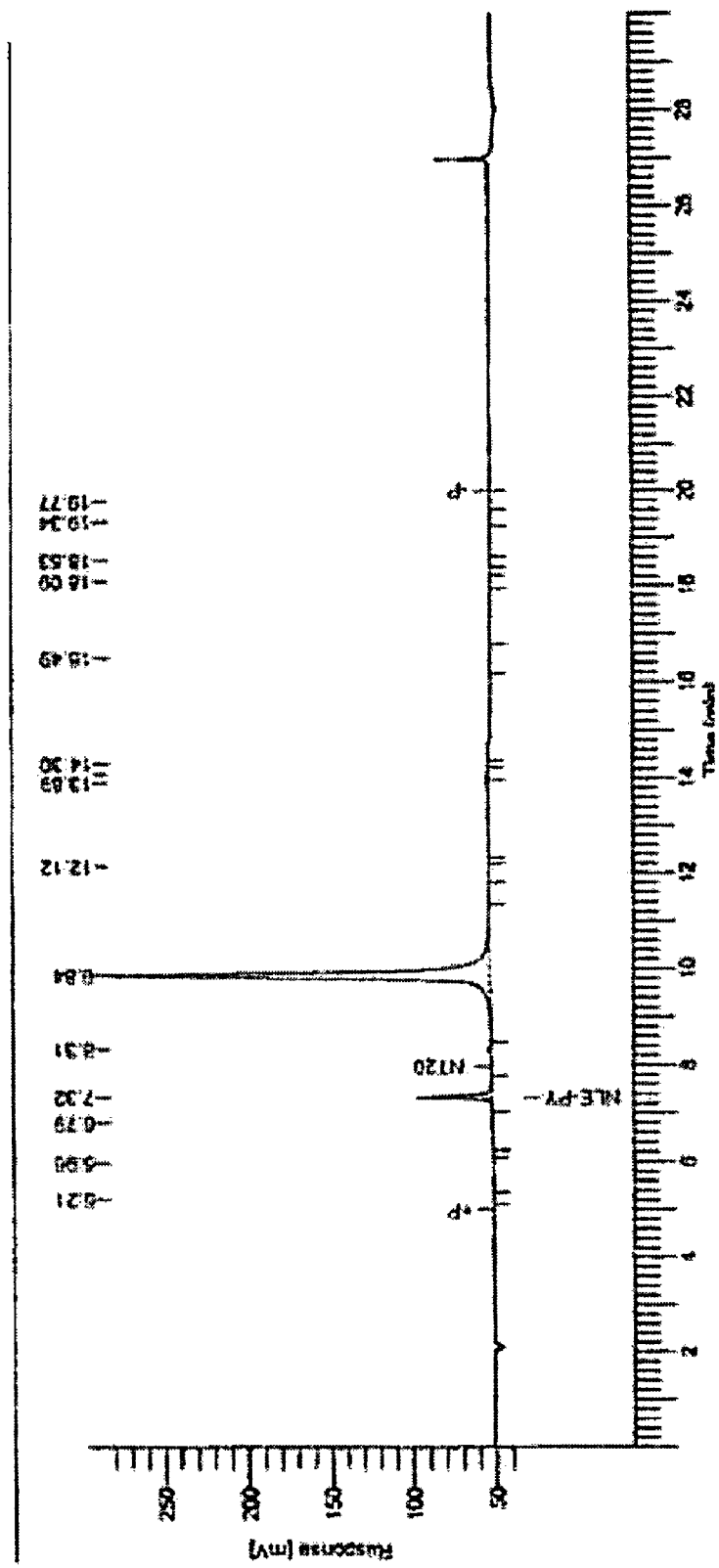
FIG. 4 shows a HPLC chromatogram of another compound of the present invention.

Fifteen mg of peptide from example 72 was weighed out and dissolved in 50 mM Borate, pH 7.4 buffer. Two hundred forty-four mg 30 kDa PEG-SPA was weighed to achieve a 2:1 PEG:peptide molar ratio and added to the dissolved peptide. The reaction mixture was agitated at room temperature for 2 h before it was diluted 10-fold in 20 mM NaOAc, pH 4.5 buffer and purified by cation exchange chromatography on SP-Sepharose FF (Amersham). FIG. 4 is an HPLC chromatogram of 30 kDa PEG-PYY peptide. The reaction yielded 88.3% of 30 kDa PEG-peptide.

Figure 5:
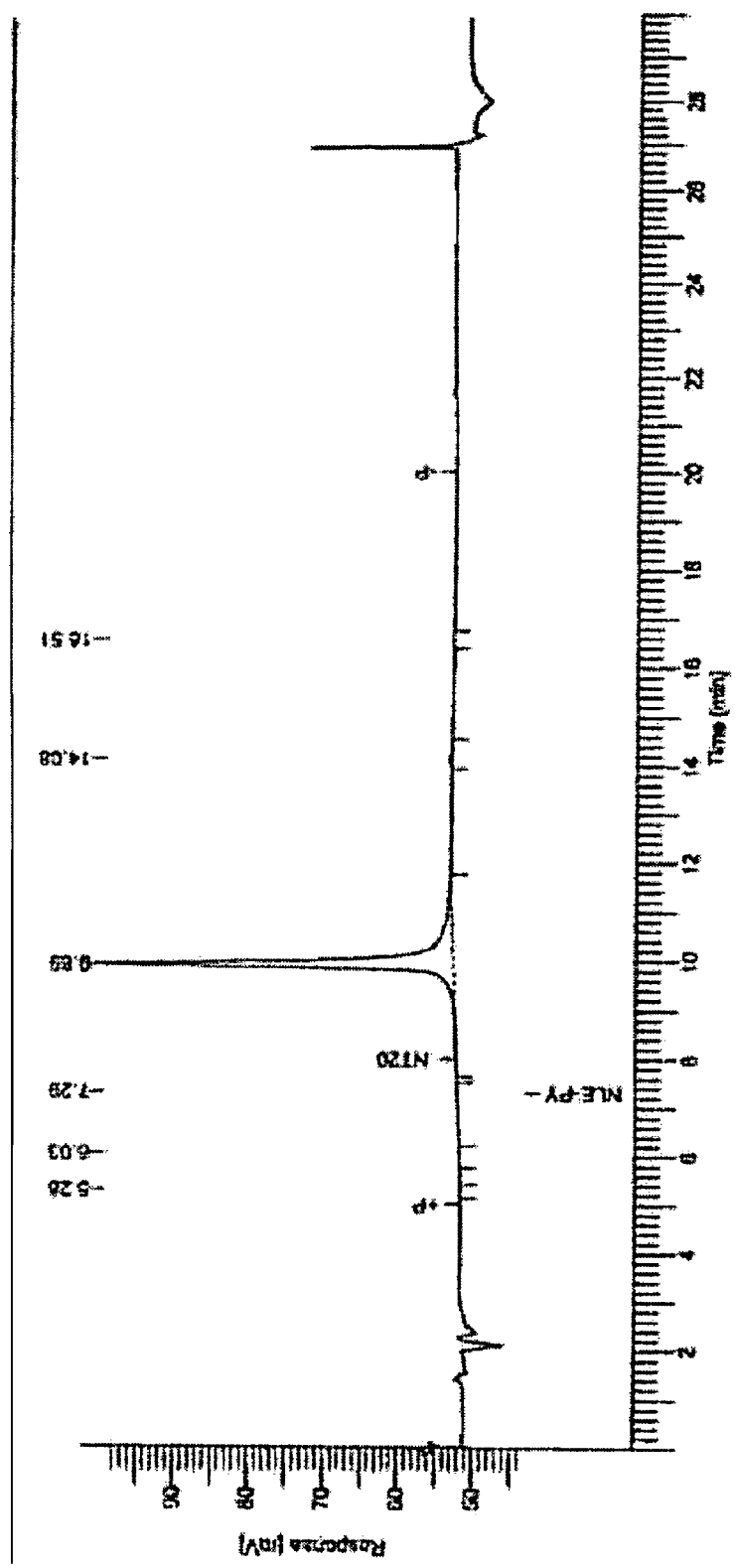
FIG. 5 shows a HPLC chromatogram of a compound of the present invention.
Figure 6:
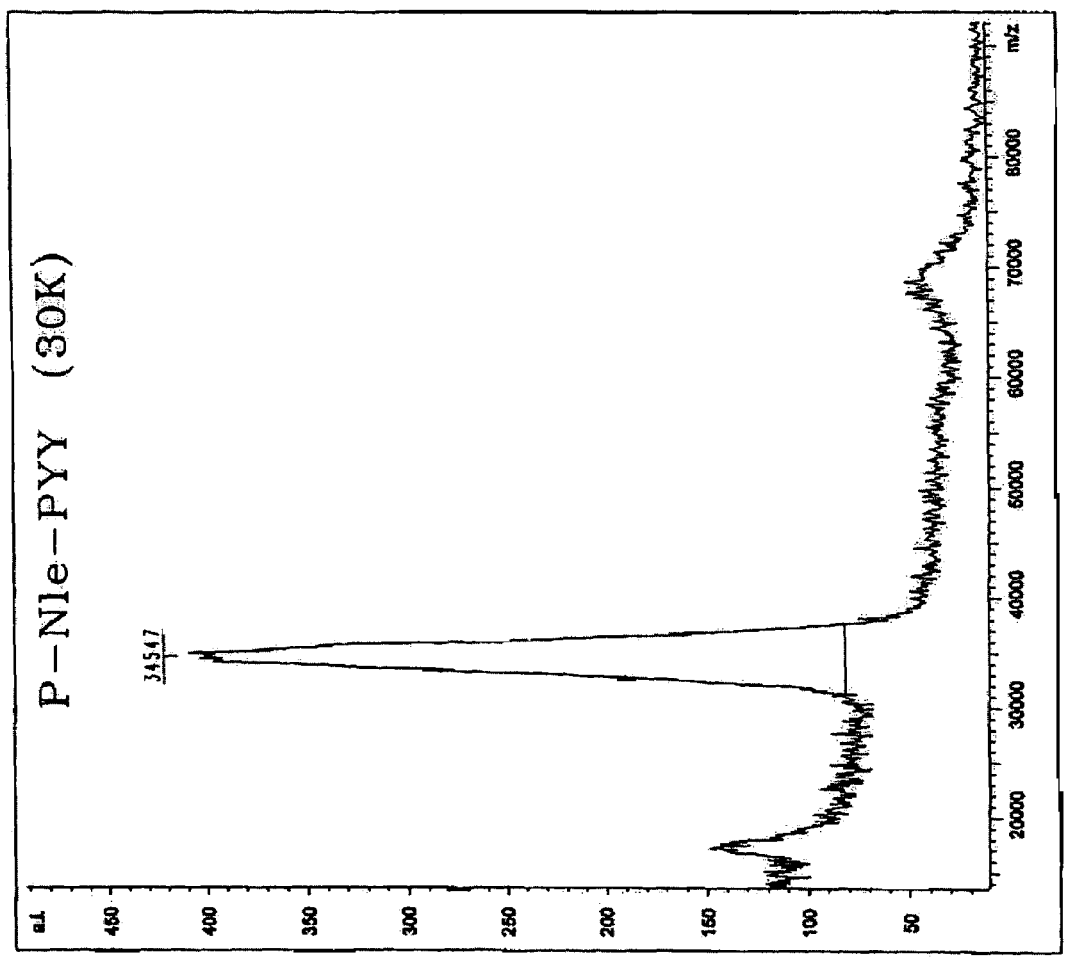
FIG. 6 shows a MALDI-TOF of a compound of the present invention.
Figure 7:
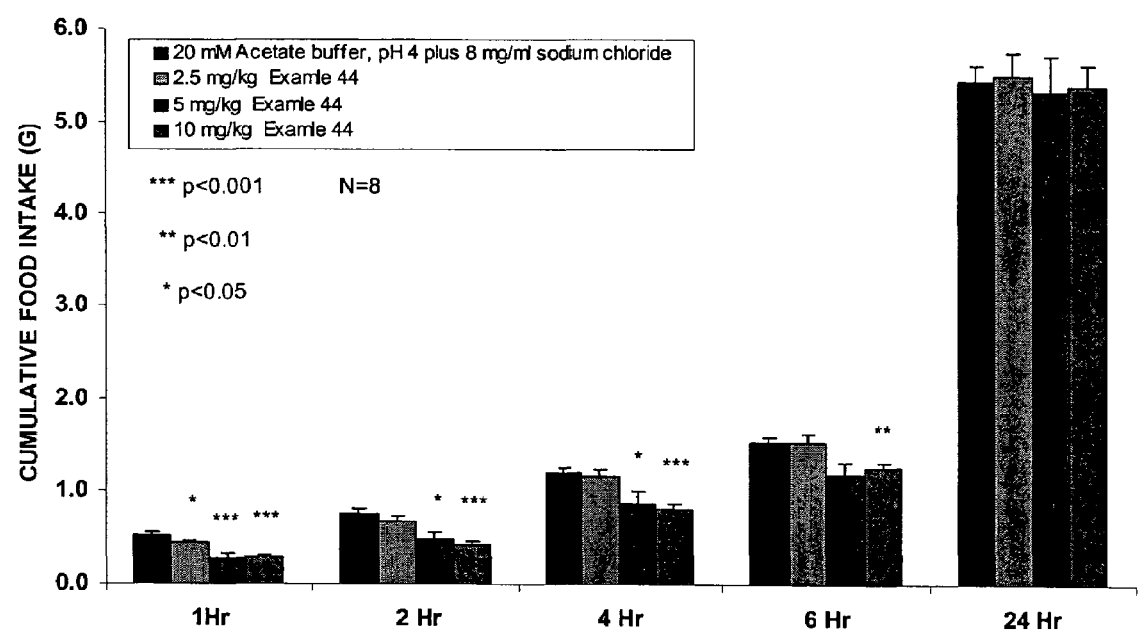
FIG. 7 shows a chart of the effects on food intake after administration of a compound of the present invention.
Figure 8:
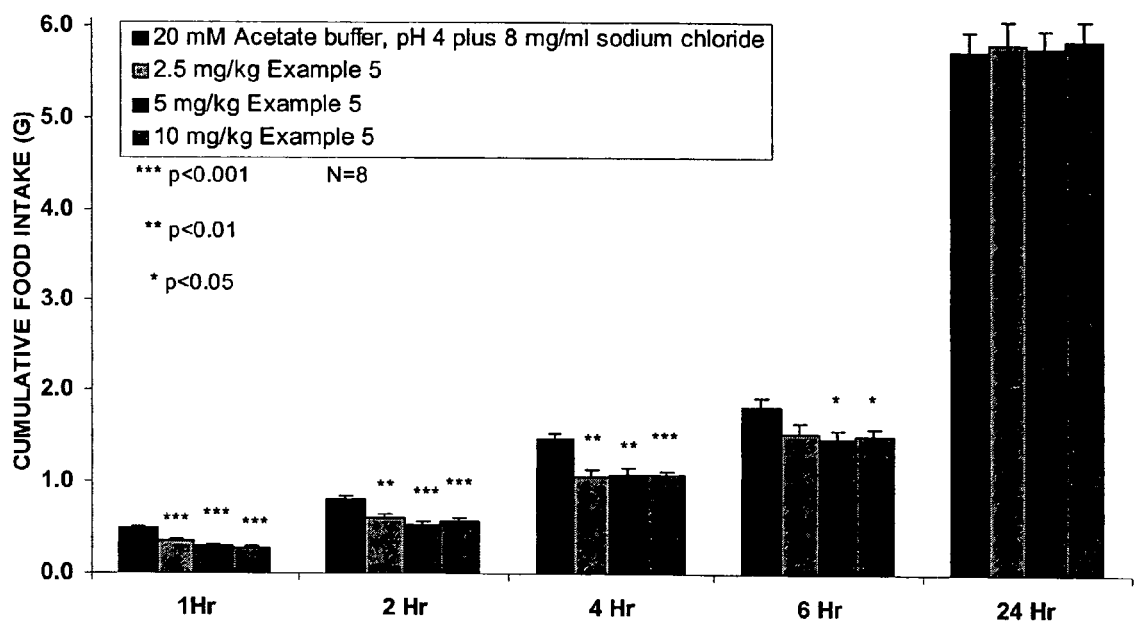
FIG. 8 shows a chart of the effects on food intake after administration of another compound of the present invention.
Figure 9:
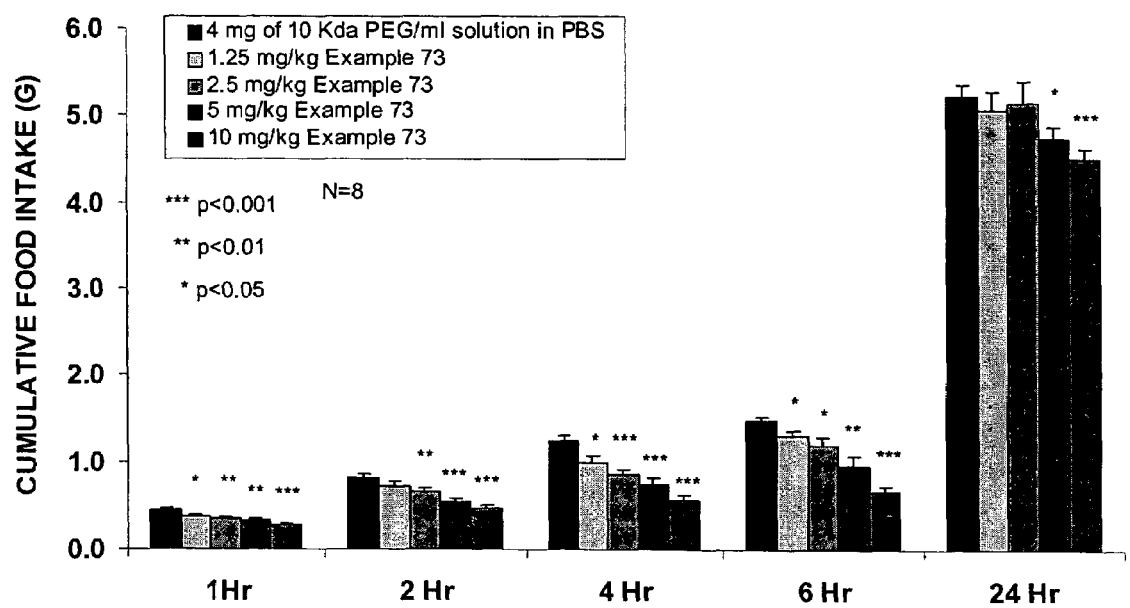
FIG. 9 shows a chart of the effects on food intake after administration of a yet another compound of the present invention.
Figure 10:
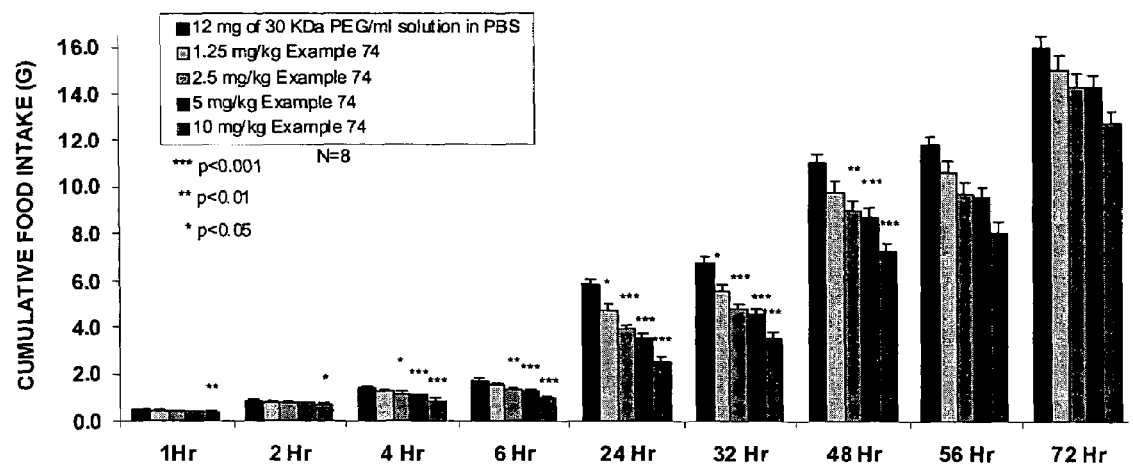
FIG. 10 shows a chart of the effects on food intake after administration of a still another compound of the present invention.

Mono-pegylated PYY peptide was eluted using a step NaCl gradient. Typically, the desired mono-pegylated PYY peptide eluted with 125 mM NaCl. The eluted PEG-PYY peptide was concentrated in an Amicon ultrafiltration cell using a 10 kDa MW cutoff membrane. It was then diafiltered 10-fold once with PBS. Concentrated peptide was submitted for analysis, assayed and stored at −20 C. FIG. 5 is an HPLC chromatogram of purified 30 kDa PEG-PYY peptide. Purity of 30 kDa PEG-peptide was determined to be 98.4%. FIG. 6 represents a MALDI-TOF of 30 kDa PEG-PYY peptides that was performed to confirm the molecular weight.

Example 75

Plasma Stability of Compound from Example 49

Human and mouse plasma stability of the peptide from Example 49 was measured. In this Example, 140 microgram of peptide from example 49 was incubated with 300 microliter of either human or mouse plasma for 0, 40, 90 and 150 minutes at 37.5° C. POSR incubation each sample was diluted by 50 times in 0.1% acetic acid in water. The diluted samples were then analyzed by LC/UV/MS and found to be stable.

Example 76

Plasma Stability of Compound from Example 32

Human and mouse plasma stability of the peptide from Example 32 was measured. In this Example, 51 micrograms of peptide from example 32 was incubated with 300 microliter of either human or mouse plasma for 0, 40, 90 and 150 minutes at 37.5° C. POSR incubation each sample was diluted by 50 times in 0.1% acetic acid in water. The diluted samples were then analyzed by LC/UV/MS and found to be stable.

Example 77 cAMP Agonist Assay

In this example, the following materials were used: 384-well plate; Tropix cAMP-Screen Kit; cAMP ELISA System (Applied Biosystems, cat. #T1505; CS 20000); Forskolin (Calbiochem cat. # 344270); cells: HEK293/hNPY2R; growth medium: Dulbecco's modified eagle medium (D-MEM, Gibco); 10% Fetal bovine serum (FBS, Gibco), heat-inactivated; 1% Penicillin/Streptomycin (Pen 10000 unit/ml: Strep 10000 mg/ml, Gibco); 500 mg/ml G418 (Geneticin, Gibco cat. # 11811-031); and plating medium: DMEM/F12 w/o phenol red (Gibco); 10% FBS (Gibco, cat. # 10082-147), heat-inactivated; 1% Penicillin/Streptomycin (Gibco, cat. # 15140-122); 500 mg/ml G418 (Geneticin, Gibco, cat. # 11811-031).

On the first day, medium was discarded, and the monolayer cells were washed with 10 ml PBS per flask (T225). After decanting with PBS, 5 ml VERSENE (Gibco, cat #1504006) was used to dislodge the cells (5 min @37 C.). The flask was gently tapped and the cell suspension was pooled. Each flask was rinsed with 10 ml plating medium and centrifuged at 1000 rpm for 5 min. The suspension was pooled and counted.

The suspension was resuspended in plating medium at a density of $2.0 \times 10^5$ cells/ml for HEK293/hNPY2R. 50 microliters of cells (HEK293/hNPY2R—10,000 cells/well) were transferred into the 384-well plate using Multi-drop dispenser. The plates were incubated at 37° C. overnight.

On the second day, the cells were checked for 75-85% confluence. The media and reagents were allowed to come to room temperature. Before the dilutions were prepared, the stock solution of stimulating compound in dimethyl sulphoxide (DMSO, Sigma, cat #D2650) was allowed to warm up to 32 C. for 5-10 min. The dilutions were prepared in DMEM/F12 with 0.5 mM 3-Isobutyl-1-methylxanthine (IBMX, Calbiochem, cat #410957) and 0.5 mg/ml BSA. The final DMSO concentration in the stimulation medium was 1.1% with Forskolin concentration of 5 µM.

The cell medium was tapped off with a gentle inversion of the cell plate on a paper towel. 50 µL of stimulation medium was placed per well (each concentration done in four replicates). The plates were incubated at room temperature for 30 min, and the cells were checked under a microscope for toxicity.

After 30 minutes of treatment, the stimulation media was discarded and 50 µl/well of Assay Lysis Buffer (provided in the Tropix kit) was. The plates were incubated for 45 min@ 37° C.

20 µL of the lysate was transferred from stimulation plates into the pre-coated antibody plates (384-well) from the Tropix kit. 10 µL of AP conjugate and 20 µL of anti-cAMP antibody was added. The plates were incubated at room temperature while shaking for 1 hour. The plates were then washed 5 times with Wash Buffer, 70 µL per well for each wash. The plates were tapped to dry. 30 µL/well of CSPD/Saphire-II RTU substrate/enhancer solution was added and incubated for 45 min @ RT (shake). Signal for 1 sec/well in a Luminometer. (VICTOR-V) was measured.

Example 78

In Vivo Reduction of Food Intake Assay

In this Example, compounds of Examples 5, 44, 73 and 74 were administered to four sets of mice in four separate experiments to measure effect on food intake. C57BL/6J male mice or DIO (diet-induced obese) male mice were used in the experiments, with eight mice per experimental group. The mice were maintained on a regular light cycle (6 AM—ON; 6 PM—OFF). The mice were fasted for 24 hours prior to testing with ad lib access to water. During the test, mice were housed one per cage.

The compounds of Examples 5 and 44 were administered intraperitoneally; and the compounds of Examples 73 and 74 were administered subcutaneously. Food intake was measured 1, 2, 4, 6, and 24 hours after dosing and the results presented in FIGS. 7 to 10. Food intake was measured for longer time intervals for the compounds of Examples 73 and 74, and shown in FIGS. 9 and 10. In each Figure, cumulative and time interval food consumptions were measured in individual mice. Mean food consumption and percent change from vehicle were calculated for each time interval. Data was analyzed by using two-tailed Student t-test. FIGS. 7 to 10 show that the compounds of the present invention are effective in reducing food intake when compared to controls.

Example 79

CaFlux Assay

Hek-293 cells were stably transfected with the G protein chimera Gaqi9 and the hygromycin-B resistance gene were further transfected with the human NPY2 receptor and G418 antibiotic selection. Following selection in both hygromycin-B and G418, individual clones were assayed for their response to PYY. The transfected cells were cultured in DMEM medium supplemented with 10% fetal bovine serum, 50 µg/ml hygromycin-B 2 mM glutamine, 100 U/ml penicillin, 100 µg/ml streptomycin and 250 µg/ml G418. Cells are harvested with trypsin-EDTA and counted using ViaCount reagent. The cell suspension volume is adjusted to $4.8 \times 10^5$ cells/ml with complete growth media. Aliquots of 25 µL are dispensed into 384 well Poly-D Lysine coated black/clear microplates (Falcon) and the microplates were placed in a 37° C. $CO_2$ incubator overnight.

Loading Buffer (Calcium-3 Assay Kit, Molecular Devices) was prepared by dissolving the contents of one vial (Express Kit) into 1000 ml Hank's Balanced Salt Solution containing 20 mM HEPES and 5 mM probenecid. Aliquots of 25 µL of diluted dye was dispensed into the cell plates and the plates are then incubated for 1 hour at 37° C.

During the incubation, test compounds were prepared at 3.5× the desired concentration in HBSS (20 mM HEPES)/ 0.05% BSA/1% DMSO and transferred to a 384 well plate for use on FLIPR.

After incubation, both the cell and compound plates were brought to the FLIPR and 20 µL of the diluted compounds were transferred to the cell plates by the FLIPR. During the assay, fluorescence readings were taken simultaneously from all 384 wells of the cell plate every 1.5 seconds. Five readings were taken to establish a stable baseline, and then 20 µL of sample was rapidly (30 µL/sec) and simultaneously added to each well of the cell plate. The fluorescence was continuously monitored before, during and after sample addition for a total elapsed time of 100 seconds. Responses (increase in peak fluorescence) in each well following addition was determined. The initial fluorescence reading from each well, prior to ligand stimulation, was used as a zero baseline value for the data from that well. The responses are expressed as % of maximal response of the positive control.

The compounds of the present invention exhibited selective Neuropeptide-2 receptor activity in vitro, as demonstrated in the cAMP assay (Example 77) and CaFlux Assay (FLIPR) (Example 78). Summary of the in vitro results, IC50 and EC50 for Examples 3 to 74, are illustrated in Table 1 below:

TABLE 1

| Example | Sequence | Y2R EC50(nM) FLIPR | Y2R IC50(nM) cAMP | Y1R EC50(nM) FLIPR | Y4R EC50(nM) FLIPR |
|---|---|---|---|---|---|
| 3 | YPIKPEAPGEDASPEELNRYYASLRHYLNLVTRQRY (1-36) | 0.76 | 0.042 | 62 | 123 |
| 4 | IKPEAPGEDASPEELNRYYASLRHYLNLVTRQRY (3-36) | 2.93 | 0.032 | 557 | >5000 |
| 5 | IK-Pqa-RHYLNLVTRQRY (SEQ IN NO: 5) | 3.2 | 0.032 | 373 | >5000 |
| 6 | Ac-IK-Pqa-RHYLNLVTRQRY (SEQ IN NO: 5) | 0.58 | 0.026 | 184 | >5000 |
| 7 | IK-Pqa-RHYLNLVTRARY (SEQ IN NO: 6) | 176 | 29 | >5000 | >5000 |
| 8 | IK-Pqa-RHYLNLVARQRY (SEQ IN NO: 7) | 18.6 | 5.27 | >5000 | >5000 |
| 9 | IK-Pqa-RHYLNLATRQRY(SEQ IN NO: 8) | 9.65 | 0.21 | >5000 | >5000 |
| 10 | IK-Pqa-RHYLNAVTRQRY (SEQ IN NO: 9) | 4.85 | 0.25 | >5000 | >5000 |
| 11 | IK-Pqa-RHYLALVTRQRY (SEQ IN NO: 10) | 38.3 | 3.11 | >5000 | >5000 |
| 12 | IK-Pqa-RHYANLVTRQRY (SEQ IN NO: 11) | 6.25 | 0.24 | >5000 | >5000 |
| 13 | IK-Pqa-RHALNLVTRQRY (SEQ IN NO: 12) | 10.8 | 1.39 | >5000 | >5000 |
| 14 | IK-Pqa-RAYLNLVTRQRY (SEQ IN NO: 13) | 12.2 | 0.062 | >5000 | >5000 |
| 15 | IK-Pqa-AHYLNLVTRQRY (SEQ IN NO: 14) | 25 | 0.639 | 3400 | >5000 |
| 16 | IA-Pqa-RHYLNLVTRQRY (SEQ IN NO: 5) | 1.68 | 0.079 | 1000 | >5000 |
| 17 | Ac-IA-Pqa-RHYLNLVTRQRY (SEQ IN NO: 5) | 2.47 | 0.247 | >5000 | 3017 |
| 18 | AK-Pqa-RHYLNLVTRQRY (SEQ IN NO: 5) | 0.62 | 0.172 | >5000 | >5000 |
| 19 | IK-Pqa-RHYLNLVTRQR(D)Y | 3.5 | 1.09 | 3300 | >5000 |
| 20 | IK-Pqa-RHYLNLVTRQ(D)RY | 110 | 25 | >5000 | >5000 |
| 21 | IK-Pqa-RHYLNLVT(D)RQRY | 324 | 65 | >5000 | >5000 |
| 22 | IK-Pqa-RHYLNL(D)VTRQRY | 322 | 21 | >5000 | >5000 |
| 23 | IK-Pqa-RHYLN(D)LVTRQRY | 66 | 22 | >5000 | >5000 |
| 24 | IK-Pqa-RHYL(D)NLVTRQRY | 48 | 0.92 | 3800 | >5000 |
| 25 | IK-Pqa-RHY(D)LNLVTRQRY | 5.26 | 0.37 | 3800 | >5000 |
| 26 | IK-Pqa-RH(D)YLNLVTRQRY | 2.98 | 0.26 | 654 | >5000 |
| 27 | IK-Pqa-R(D)HYLNLVTRQRY | 12.3 | 3.18 | 431 | >5000 |
| 28 | IK-Pqa-(D)RHYLNLVTRQRY | 5.2 | 0.201 | 1100 | >5000 |
| 29 | I(D)K-Pqa-RHYLNLVTRQRY (SEQ IN NO: 5) | 0.43 | 0.078 | >5000 | >5000 |
| 30 | (D)IK-Pqa-RHYLNLVTRQRY (SEQ IN NO: 5) | 0.22 | 0.099 | >5000 | >5000 |
| 31 | IK-Pqa-RHYLNLVTRQR(N-methyl)Y (SEQ IN NO: 15) | 11.8 | 2.6 | >5000 | >5000 |
| 32 | IK-Pqa-RHYLNLVTRQ(N-methyl)RY (SEQ IN NO: 16) | 18.9 | 0.417 | >5000 | >5000 |
| 33 | IK-Pqa-RHYLNLVT(N-methyl)RQRY (SEQ IN NO: 17) | 30.6 | 13.5 | >5000 | >5000 |
| 34 | IK-Pqa-RHYLNLV(N-methyl)TRQRY (SEQ IN NO: 18) | 78.6 | 89 | >5000 | >5000 |
| 35 | IK-Pqa-RHYLNL(N-methyl)VTRQRY (SEQ IN NO: 19) | 44.4 | 42 | >5000 | >5000 |
| 36 | IK-Pqa-RHYLN(N-methyl)LVTRQRY (SEQ IN NO: 20) | 103 | 12 | >5000 | >5000 |
| 37 | IK-Pqa-RHY(N-methyl)LNLVTRQRY (SEQ IN NO: 21) | 782 | 168 | >5000 | >5000 |
| 38 | IK-Pqa-RH(N-methyl)YLNLVTRQRY (SEQ IN NO: 22) | 1.2 | 11.7 | >5000 | >5000 |
| 39 | IK-Pqa-R(N-methyl)HYLNLVTRQR (SEQ IN NO: 23)Y | 41.9 | 1.488 | 3800 | >5000 |
| 40 | IK-Pqa-(N-methyl)RHYLNLVTRQRY (SEQ IN NO: 24) | 4.4 | 0.218 | 1600 | >5000 |
| 41 | I(N-methyl)K-Pqa-RHYLNLVTRQRY (SEQ IN NO: 5) | 0.614 | 0.19 | 834 | >5000 |
| 42 | (N-methyl)IK-Pqa-RHYLNLVTRQRY (SEQ IN NO: 5) | 0.799 | 0.12 | 327 | >5000 |
| 43 | INle-Pqa-RHYLNLVTRQRY (SEQ IN NO: 5) | 0.89 | 0.096 | 430 | >5000 |
| 44 | Ac-INle-Pqa-RHYLNLVTRQRY (SEQ IN NO: 5) | 6.1 | 0.338 | 760 | >5000 |
| 45 | Ac-INle-Pqa-FHYLNLVTRQRY (SEQ IN NO: 25) | 19.3 | 2.74 | >5000 | >5000 |
| 46 | IK-Pqa-RHWLNLVTRQRY (SEQ IN NO: 26) | 6.1 | 0.103 | 252 | >5000 |
| 47 | IK-Pqa-AHWLNLVTRQRY (SEQ IN NO: 27) | 17.05 | 0.547 | 1100 | >5000 |
| 48 | Ac-INle-Pqa-RHYLNLVTRQR(D)Y | 107 | 2.2 | 2020 | >5000 |

TABLE 1-continued

| Example | Sequence | Y2R EC50(nM) FLIPR | Y2R IC50(nM) cAMP | Y1R EC50(nM) FLIPR | Y4R EC50(nM) FLIPR |
|---|---|---|---|---|---|
| 49 | Ac-INle-Pqa-RHYLNLVTRQR(N-methyl)Y (SEQ IN NO: 15) | 113 | 3.6 | 4200 | >5000 |
| 50 | Ac-INle-Pqa-RHYLys(28)NLVAsp(32)RQRY (cyclo Lys-Asp) (SEQ IN NO: 28) | 92.4 | 33.48 | >5000 | >5000 |
| 51 | IK-Cms-RHYLNLVTRQRY (SEQ IN NO: 5) | 4.91 | 0.1 | >5000 | >5000 |
| 52 | IKG-Cms-RHYLNLVTRQRY (SEQ IN NO: 5) | 4.16 | 0.085 | >5000 | >5000 |
| 53 | Ac-INle-Cms-RHYLys(28)NLVAsp(32)RQRY (cyclo Lys-Asp) (SEQ IN NO: 28) | 146 | 32.25 | >5000 | >5000 |
| 54 | Ac-INle-Pqa-RHTicLNLVTRQRY (SEQ IN NO: 31) | 163 | 45 | >5000 | >5000 |
| 55 | Ac-INle-Pqa-RHBipLNLVTRQRY (SEQ IN NO: 32) | 24.7 | 3.72 | 561 | >5000 |
| 56 | Ac-INle-Pqa-RHDipLNLVTRQRY (SEQ IN NO: 33) | 33.5 | 1.21 | 1516 | >5000 |
| 57 | Ac-INle-Pqa-RH(1)NaILNLVTRQRY (SEQ IN NO: 34) | 13 | 1.36 | 701 | >5000 |
| 58 | Ac-INle-Pqa-RH(2)NaILNLVTRQRY (SEQ IN NO: 35) | 12.3 | 2.68 | 870 | >5000 |
| 59 | Ac-INle-Pqa-RH(3,4,5 Trifluoro Phe)LNLVTRQRY (SEQ IN NO: 36) | 13.8 | 1.34 | 1089 | >5000 |
| 60 | Ac-INle-Pqa-RH(2,3,4,5,6 Pentafluoro Phe)LNLVTRQRY (SEQ IN NO: 37) | 14.2 | 2.13 | 832 | >5000 |
| 61 | Ac-INle-Pqa-R(4-MeOApc)YLNLVTRQRY (SEQ IN NO: 38) | 11.9 | 7.8 | >5000 | >5000 |
| 62 | Ac-INle-Pqa-R(3-PaI)YLNLVTRQRY (SEQ IN NO: 39) | 5.6 | 1.78 | 2022 | >5000 |
| 63 | Ac-INle-Pqa-R(4-PaI)YLNLVTRQRY (SEQ IN NO: 40) | 4.97 | 0.099 | >5000 | >5000 |
| 64 | Ac-INle-Pqa-(3,4,5 Trifluro Phe)HYLNLVTRQRY (SEQ IN NO: 41) | 46 | 1.74 | >5000 | >5000 |
| 65 | Ac-INle-Pqa-(2,3,4,5,6 Pentafluro Phe)HYLNLVTRQRY (SEQ IN NO: 42) | 134 | 9.37 | >5000 | >5000 |
| 66 | Ac-Aib-Nle-Pqa-RHYLNLVTRQRY (SEQ IN NO: 5) | 8.9 | 0.38 | 3329 | >5000 |
| 67 | Ac1-1-Aic-Nle-Pqa-RHYLNLVTRQRY (SEQ IN NO: 5) | 8.8 | 0.64 | 1654 | >5000 |
| 68 | Ac1-1-Aic-Nle-Pqa-RHYLNLVTRQRY (SEQ IN NO: 5) | 6 | 1 | 2646 | >5000 |
| 69 | Ac-2-2Aic-Nle-Pqa-RHYLNLVTRQRY (SEQ IN NO: 5) | 8.2 | 0.45 | >5000 | >5000 |
| 70 | Ac-Ach-Nle-Pqa-RHYLNLVTRQRY (SEQ IN NO: 5) | 7.1 | 0.57 | >5000 | >5000 |
| 71 | Ac-Acp-Nle-Pqa-RHYLNLVTRQRY (SEQ IN NO: 5) | 8.7 | 0.303 | >5000 | >5000 |
| 72 | H-INle-Pqa-RHYLNLVTRQRY (SEQ IN NO: 5) | 0.89 | 0.096 | 450 | >5000 |
| 73 | (PEG-10,000) INle-Pqa-RHYLNLVTRQRY (SEQ IN NO: 5) | 7.4 | 45 | | |
| 74 | (PEG-30,000) INle-Pqa-RHYLNLVTRQRY (SEQ IN NO: 5) | 15.4 | 79 | | |

It is to be understood that the invention is not limited to the particular embodiments of the invention described above, as variations of the particular embodiments may be made and still fall within the scope of the appended claims.

What is claimed is:

1. A neuropeptide-2 receptor agonist of the formula (I):

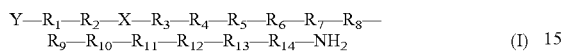  (I)

wherein:

X is selected from the group consisting of N-piperazin-1-yl-4(3H)-quinozolinone-3-acetic acid (Pqa), N-(5-O-carboxymethyl )-serotonin (Cms), 4-(2-aminoethyl)-6-dibenzofuranpropanoic acid, 4-(1-piperidin-4-yl)-butanoic acid and 4-(2-aminoethyl) -1-carboxymethyl piperazine, Y is H, a substituted or unsubstituted alkyl, a substituted or unsubstituted lower alkyl, a substituted or unsubstituted aryl, a substituted or unsubstituted alkoxy or a poly (ethylene) glycol moiety, $R_1$ is Ile, Ala, (D) Ile, N-methyl Ile, Aib, 1-1 Aic, 2-2 Aic, Ach or Acp, $R_2$ is Lys, Ala, (D) Lys, NMelys, Nle or (Lys-Gly), $R_3$ is Arg, Ala, (D)Arg, N-methylArg, Phe, 3,4,5- Trifluo-roPhe or 2,3,4,5,6-pentafluoro Phe, $R_4$ is His, Ala, (D)His, N-methyl His, 4-MeOApc, 3-Pal or 4-Pal, $R_5$ is Tyr, Ala, (D) Tyr, N- methyl Tyr, Trp, Tic, Bip, Dip, (1)Nal, (2)Nal, 3,4,5-TrifluroPhe or 2,3,4,5,6- Pentafluoro Phe, $R_6$ is Leu, Ala, (D)Leu or N-methyl Leu, $R_7$ is Asn, Ala or (D)Asn, $R_8$ is Leu, Ala, (D)Leu or N-methyl Leu, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, and $R_{14}$ is Tyr, (D) Tyr or N- methyl Tyr, or a pharmaceutically acceptable salt thereof.

2. The neuropeptide-2 receptor agonist according to claim 1, wherein X is Pqa.

3. The neuropeptide-2 receptor agonist according to claim 1, wherein X is cms.

4. The neuropeptide-2 receptor agonist according to claim 1, wherein Y is a ($C_1$-$C_6$) alkyl moiety.

5. A pharmaceutical composition, comprising a neuropeptide-2 agonist of the formula (I):

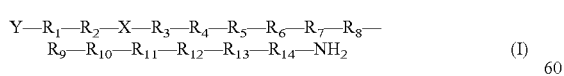  (I)

wherein:

X is selected from the group consisting of N-piperazin-1-yl-4(3H)-quinozolinone-3-acetic acid (Pqa), N-(5-O-carboxymethyl)-serotonin (Cms), 4-(2-aminoethyl)-6-dibenzofuranpropanoic acid, 4-( 1-piperidin-4-yl)-butanoic acid and 4-(2-aminoethyl)-1-carboxymethyl piperazine, Y is H, a substituted or unsubstituted alkyl, a substituted or unsubstituted lower alkyl, a substituted or unsubstituted aryl, a substituted or unsubstituted alkoxy or a poly (ethylene) glycol moiety, $R_1$ is Ile, Ala, (D) Ile, N-methyl Ile, Aib, 1-1Aic, 2-2 Aic, Ach or Acp, $R_2$ is Lys, Ala, (D) Lys, NMelys, Nle or (Lys-Gly), $R_3$ is Arg, Ala, (D)Arg, N-methylArg, Phe, 3,4,5- Trifluo-roPhe or 2,3,4,5,6-Pentafluoro Phe, $R_4$ is His, Ala, (D)His, N-methyl His. 4-MeOApc, 3-Pal or 4-Pal, $R_5$ is Tyr, Ala, (D) Tyr, N- methyl Tyr, Trp, Tic, Bip, Dip, (1)Nal, (2)Nal, 3,4,5-TrifluroPhe or 2,3,4,5,6- Pentafluoro Phe, $R_6$ is Leu, Ala, (D)Leu or N-methyl Leu, $R_7$ is Asn, Ala or (D)Asn, $R_8$ is Leu, Ala, (D)Leu or N-methyl Leu, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, and $R_{14}$ is Tyr, (D) Tyr or N- methyl Tyr, or a pharmaceutically acceptable salt thereof, and a pharmaceutically acceptable carrier.

6. The pharmaceutical composition according to claim 5, wherein X is Pqa.

7. The pharmaceutical composition according to claim 5, wherein X is Cms.

8. The pharmaceutical composition according to claim 5, wherein Y is a ($C_1$-$C_6$) alkyl moiety.

9. A method of treating obesity in a patient in need thereof, comprising administering to said patient a therapeutically effective amount of a neuropeptide-2 receptor agonist of the formula (I):

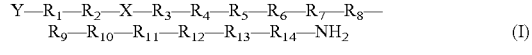  (I)

wherein:

X is selected from the group consisting of N-piperazin-1-yl-4(3H)-quinozolinone-3-acetic acid (Pqa), N-(5-O-carboxymethyl)-serotonin (Cms), 4-(2-aminoethyl )-6-dibenzofuranpropanoic acid, 4-(1-piperidin-4-yl)-butanoic acid and 4-(2-aminoethyl)-1 -carboxymethyl piperazine, Y is H, a substituted or unsubstituted alkyl, a substituted or unsubstituted lower alkyl, a substituted or unsubstituted aryl, a substituted or unsubstituted alkoxy or a poly (ethylene) glycol moiety, $R_1$ is Ile, Ala, (D) Ile, N-methyl Ile, Aib, 1-1 Aic, 2-2 Aic, Ach or Acp, $R_2$ is Lys, Ala, (D) Lys, NMelys, Nle or (Lys-Gly), $R_3$ is Arg, Ala, (D)Arg, N-methylArg, Phe, 3,4,5-Trifluo-roPhe or 2,3,4,5,6-Pentafluoro Phe, $R_4$ is His, Ala, (D)His, N-methyl His, 4-MeOApc, 3-Pal or 4-Pal, $R_5$ is Tyr, Ala, (D) Tyr N- methyl Tyr, Trp, Tic, Bip, Dip, (1)Nal, (2)Nal, 3,4,5-TrifluroPhe or 2,3,4,5,6- Pentafluoro Phe, $R_6$ is Leu, Ala, (D)Leu or N-methyl Leu, $R_7$ is Asn, Ala or (D)Asn, $R_8$ is Leu, Ala, (D)Leu or N-methyl Leu, $R_9$ is Val, Ala, (D) Val or N-methyl Val, $R_{10}$ is Thr, Ala or N-methyl Thr, $R_{11}$ is Arg, (D) Arg or N-methyl Arg, $R_{12}$ is Gln or Ala, $R_{13}$ is Arg, (D)Arg or N-methyl Arg, and $R_{14}$ is Tyr, (D) Tyr or N- methyl Tyr, or a pharmaceutically acceptable salt thereof.

10. The method according to claim 9,wherein said neuropeptide-2 receptor agonist is administered to said patient once every three days.

11. The method according to claim 9, wherein said neuropeptide-2 receptor agonist is administered to said patient once a week.

12. The method according to claim 9, wherein said neuropeptide-2 receptor agonist is administered to said patient orally, intranasally, intravenously, subcutaneously, parenterally, transdermally, intraperitoneally or rectally.

13. The method according to claim 9, wherein said neuropeptide-2 receptor agonist is administered intranasally.

14. The method according to claim 9, wherein said neuropeptide-2 receptor agonist is administered subcutaneously.

15. The method according to claim 9, wherein said neuropeptide-2 receptor agonist is administered at a dosage of from about 2.5 to about 10 mglkg.

16. The method according to claim 9, wherein said neuropeptide-2 receptor agonist is administered at a dosage of from about 2.5 to about 5 mg/kg.

17. The method according to claim 9, wherein said neuropeptide-2 receptor agonist is administered at a dosage of from about 5 to about 10 mg/kg.

* * * * *

SEQUENCE LISTING

```
<160> NUMBER OF SEQ ID NOS: 42

<210> SEQ ID NO 1
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 1

Arg His Tyr Leu Asn Leu Val Thr Arg Gln Arg Tyr
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated
```

```
<400> SEQUENCE: 2

Arg His Tyr Leu Asn Leu Val Thr Arg Gln Arg Tyr
 1               5                  10

<210> SEQ ID NO 3
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 3

Tyr Pro Ile Lys Pro Glu Ala Pro Gly Glu Asp Ala Ser Pro Glu Glu
 1               5                  10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 4
<211> LENGTH: 34
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 4

Ile Lys Pro Glu Ala Pro Gly Glu Asp Ala Ser Pro Glu Glu Leu Asn
 1               5                  10                  15

Arg Tyr Tyr Ala Ser Leu Arg His Tyr Leu Asn Leu Val Thr Arg Gln
            20                  25                  30

Arg Tyr

<210> SEQ ID NO 5
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 5

Arg His Tyr Leu Asn Leu Val Thr Arg Gln Arg Tyr
 1               5                  10

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 6

Arg His Tyr Leu Asn Leu Val Thr Arg Ala Arg Tyr
 1               5                  10
```

```
<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 7

Arg His Tyr Leu Asn Leu Val Ala Arg Gln Arg Tyr
 1               5                  10

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 8

Arg His Tyr Leu Asn Leu Ala Thr Arg Gln Arg Tyr
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 9

Arg His Tyr Leu Asn Ala Val Thr Arg Gln Arg Tyr
 1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 10

Arg His Tyr Leu Ala Leu Val Thr Arg Gln Arg Tyr
 1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 11

Arg His Tyr Ala Asn Leu Val Thr Arg Gln Arg Tyr
```

```
<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 12

Arg His Ala Leu Asn Leu Val Thr Arg Gln Arg Tyr
 1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 13

Arg Ala Tyr Leu Asn Leu Val Thr Arg Gln Arg Tyr
 1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 14

Ala His Tyr Leu Asn Leu Val Thr Arg Gln Arg Tyr
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (12)
<223> OTHER INFORMATION: (NMe)Tyr
<220> FEATURE:
<223> OTHER INFORMATION: C-term amidated

<400> SEQUENCE: 15

Arg His Tyr Leu Asn Leu Val Thr Arg Gln Arg Tyr
 1               5                  10

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<221> NAME/KEY: MOD_RES
<222> LOCATION: (11)
<223> OTHER INFORMATION: (NMe)Arg
<220> FEATURE:
<223> OTHER INFORMATION: C-term amidated

<400> SEQUENCE: 16

Arg His Tyr Leu Asn Leu Val Thr Arg Gln Arg Tyr
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (9)
<223> OTHER INFORMATION: (NMe)Arg
<220> FEATURE:
<223> OTHER INFORMATION: C-term amidated

<400> SEQUENCE: 17

Arg His Tyr Leu Asn Leu Val Thr Arg Gln Arg Tyr
  1               5                  10

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (8)
<223> OTHER INFORMATION: (NMe)Thr
<220> FEATURE:
<223> OTHER INFORMATION: C-term amidated

<400> SEQUENCE: 18

Arg His Tyr Leu Asn Leu Val Thr Arg Gln Arg Tyr
  1               5                  10

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)
<223> OTHER INFORMATION: (NMe)Val
<220> FEATURE:
<223> OTHER INFORMATION: C-term amidated

<400> SEQUENCE: 19

Arg His Tyr Leu Asn Leu Val Thr Arg Gln Arg Tyr
  1               5                  10

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (6)
<223> OTHER INFORMATION: (NMe)Leu
<220> FEATURE:
<223> OTHER INFORMATION: C-term amidated

<400> SEQUENCE: 20

Arg His Tyr Leu Asn Leu Val Thr Arg Gln Arg Tyr
  1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)
<223> OTHER INFORMATION: (NMe)Leu
<220> FEATURE:
<223> OTHER INFORMATION: C-term amidated

<400> SEQUENCE: 21

Arg His Tyr Leu Asn Leu Val Thr Arg Gln Arg Tyr
  1               5                  10

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (NMe)Tyr
<220> FEATURE:
<223> OTHER INFORMATION: C-term amidated

<400> SEQUENCE: 22

Arg His Tyr Leu Asn Leu Val Thr Arg Gln Arg Tyr
  1               5                  10

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: (NMe)His
<220> FEATURE:
<223> OTHER INFORMATION: C-term amidated

<400> SEQUENCE: 23

Arg His Tyr Leu Asn Leu Val Thr Arg Gln Arg Tyr
  1               5                  10

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
```

```
        peptide
<220> FEATURE:
<221> NAME/KEY: MOD_RES
<222> LOCATION: (1)
<223> OTHER INFORMATION: (NMe)Arg
<220> FEATURE:
<223> OTHER INFORMATION: C-term amidated

<400> SEQUENCE: 24

Arg His Tyr Leu Asn Leu Val Thr Arg Gln Arg Tyr
 1               5                  10

<210> SEQ ID NO 25
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 25

Phe His Tyr Leu Asn Leu Val Thr Arg Gln Arg Tyr
 1               5                  10

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 26

Arg His Trp Leu Asn Leu Val Thr Arg Gln Arg Tyr
 1               5                  10

<210> SEQ ID NO 27
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: C-term amidated

<400> SEQUENCE: 27

Ala His Trp Leu Asn Leu Val Thr Arg Gln Arg Tyr
 1               5                  10

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Cyclo bridge between residues 4 and 8
<220> FEATURE:
<223> OTHER INFORMATION: C-term amidated

<400> SEQUENCE: 28

Arg His Tyr Lys Asn Leu Val Asp Arg Gln Arg Tyr
 1               5                  10
```

```
<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Asn(Trt)
<220> FEATURE:
<221> NAME/KEY: MOD_RES
<222> LOCATION: (4)
<223> OTHER INFORMATION: Asp(2Pip)
<220> FEATURE:
<221> NAME/KEY: MOD_RES
<222> LOCATION: (5)
<223> OTHER INFORMATION: Arg(Pmc)
<220> FEATURE:
<221> NAME/KEY: MOD_RES
<222> LOCATION: (6)
<223> OTHER INFORMATION: Gln(Trt)
<220> FEATURE:
<221> NAME/KEY: MOD_RES
<222> LOCATION: (7)
<223> OTHER INFORMATION: Arg(Pmc)
<220> FEATURE:
<221> NAME/KEY: MOD_RES
<222> LOCATION: (8)
<223> OTHER INFORMATION: Tyr(OBut)

<400> SEQUENCE: 29

Asn Leu Val Asp Arg Gln Arg Tyr
 1               5

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Arg(Pmc)
<220> FEATURE:
<221> NAME/KEY: MOD_RES
<222> LOCATION: (2)
<223> OTHER INFORMATION: His(Trt)
<220> FEATURE:
<221> NAME/KEY: MOD_RES
<222> LOCATION: (3)
<223> OTHER INFORMATION: Tyr(OBut)
<220> FEATURE:
<221> NAME/KEY: MOD_RES
<222> LOCATION: (5)
<223> OTHER INFORMATION: Asn(Trt)
<220> FEATURE:
<221> NAME/KEY: MOD_RES
<222> LOCATION: (9)
<223> OTHER INFORMATION: Arg(Pmc)
<220> FEATURE:
<221> NAME/KEY: MOD_RES
<222> LOCATION: (10)
<223> OTHER INFORMATION: Gln(Trt)
<220> FEATURE:
<221> NAME/KEY: MOD_RES
<222> LOCATION: (11)
<223> OTHER INFORMATION: Arg(Pmc)
<220> FEATURE:
<221> NAME/KEY: MOD_RES
<222> LOCATION: (12)
<223> OTHER INFORMATION: Tyr(OBut)
```

```
<400> SEQUENCE: 30

Arg His Tyr Lys Asn Leu Val Asp Arg Gln Arg Tyr
 1               5                  10

<210> SEQ ID NO 31
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Tic
<220> FEATURE:
<223> OTHER INFORMATION: C-term amidated

<400> SEQUENCE: 31

Arg His Xaa Leu Asn Leu Val Thr Arg Gln Arg Tyr
 1               5                  10

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Bip
<220> FEATURE:
<223> OTHER INFORMATION: C-term amidated

<400> SEQUENCE: 32

Arg His Xaa Leu Asn Leu Val Thr Arg Gln Arg Tyr
 1               5                  10

<210> SEQ ID NO 33
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: Dip
<220> FEATURE:
<223> OTHER INFORMATION: C-term amidated

<400> SEQUENCE: 33

Arg His Xaa Leu Asn Leu Val Thr Arg Gln Arg Tyr
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (1)Nal
<220> FEATURE:
<223> OTHER INFORMATION: C-term amidated
```

```
<400> SEQUENCE: 34

Arg His Xaa Leu Asn Leu Val Thr Arg Gln Arg Tyr
 1               5                  10

<210> SEQ ID NO 35
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (2)Nal
<220> FEATURE:
<223> OTHER INFORMATION: C-term amidated

<400> SEQUENCE: 35

Arg His Xaa Leu Asn Leu Val Thr Arg Gln Arg Tyr
 1               5                  10

<210> SEQ ID NO 36
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (3,4,5 Trifluoro Phe)
<220> FEATURE:
<223> OTHER INFORMATION: C-term amidated

<400> SEQUENCE: 36

Arg His Xaa Leu Asn Leu Val Thr Arg Gln Arg Tyr
 1               5                  10

<210> SEQ ID NO 37
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: (2,3,4,5,6 Pentafluoro Phe)
<220> FEATURE:
<223> OTHER INFORMATION: C-term amidated

<400> SEQUENCE: 37

Arg His Xaa Leu Asn Leu Val Thr Arg Gln Arg Tyr
 1               5                  10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: (4-MeOApc)
<220> FEATURE:
```

<223> OTHER INFORMATION: C-term amidated

<400> SEQUENCE: 38

Arg Xaa Tyr Leu Asn Leu Val Thr Arg Gln Arg Tyr
 1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: (3-Pal)
<220> FEATURE:
<223> OTHER INFORMATION: C-term amidated

<400> SEQUENCE: 39

Arg Xaa Tyr Leu Asn Leu Val Thr Arg Gln Arg Tyr
 1               5                   10

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: (4-Pal)
<220> FEATURE:
<223> OTHER INFORMATION: C-term amidated

<400> SEQUENCE: 40

Arg Xaa Tyr Leu Asn Leu Val Thr Arg Gln Arg Tyr
 1               5                   10

<210> SEQ ID NO 41
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: (3,4,5 Trifluoro Phe)
<220> FEATURE:
<223> OTHER INFORMATION: C-term amidated

<400> SEQUENCE: 41

Xaa His Tyr Leu Asn Leu Val Thr Arg Gln Arg Tyr
 1               5                   10

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: (2,3,4,5,6 Pentafluoro Phe)

```
-continued

<220> FEATURE:
<223> OTHER INFORMATION: C-term amidated

<400> SEQUENCE: 42

Xaa His Tyr Leu Asn Leu Val Thr Arg Gln Arg Tyr
 1               5                  10
```